US007652044B2

(12) United States Patent
Dong et al.

(10) Patent No.: US 7,652,044 B2
(45) Date of Patent: Jan. 26, 2010

(54) P-38 INHIBITORS

(75) Inventors: Qing Dong, San Diego, CA (US); Fabrice Pierre, La Jolla, CA (US); Jianqiang Wang, Woburn, MA (US)

(73) Assignee: Novartis A.G., Basel (CH)

( * ) Notice: Subject to any disclaimer, the term of this patent is extended or adjusted under 35 U.S.C. 154(b) by 663 days.

(21) Appl. No.: 10/860,768

(22) Filed: Jun. 2, 2004

(65) Prior Publication Data

US 2004/0254236 A1    Dec. 16, 2004

Related U.S. Application Data

(60) Provisional application No. 60/475,662, filed on Jun. 3, 2003, provisional application No. 60/531,541, filed on Dec. 19, 2003.

(51) Int. Cl.
*A61K 31/421* (2006.01)
*A61K 31/426* (2006.01)

(52) U.S. Cl. .................. 514/361; 514/370; 514/377; 514/383

(58) Field of Classification Search .................. 514/361, 514/370, 377, 383; 548/130, 133, 194, 233, 548/264.8
See application file for complete search history.

(56) References Cited

U.S. PATENT DOCUMENTS

| | | | |
|---|---|---|---|
| 3,710,795 A | 1/1973 | Higuchi et al. | |
| RE28,819 E | 5/1976 | Thompson | |
| 4,044,126 A | 8/1977 | Cook et al. | |
| 4,200,750 A | 4/1980 | Warner et al. | |
| 4,328,245 A | 5/1982 | Yu et al. | |
| 4,358,603 A | 11/1982 | Yu | |
| 4,364,923 A | 12/1982 | Cook et al. | |
| 4,409,239 A | 10/1983 | Yu | |
| 4,410,545 A | 10/1983 | Yu et al. | |
| 4,414,209 A | 11/1983 | Cook et al. | |
| 4,522,811 A | 6/1985 | Eppstein et al. | |
| 5,033,252 A | 7/1991 | Carter | |
| 5,052,558 A | 10/1991 | Carter | |
| 5,323,907 A | 6/1994 | Kalvelage | |
| 5,658,903 A | 8/1997 | Adams et al. | |
| 5,932,576 A | 8/1999 | Anantanarayan et al. | |
| 5,945,418 A | 8/1999 | Bemis et al. | |
| 5,952,381 A * | 9/1999 | Chen et al. ............ | 514/565 |
| 5,977,103 A | 11/1999 | Adams et al. | |
| 6,087,496 A | 7/2000 | Anantanarayan et al. | |
| 6,130,235 A | 10/2000 | Mavunkel et al. | |
| 6,147,080 A | 11/2000 | Bemis et al. | |
| 6,251,914 B1 | 6/2001 | Adams et al. | |
| 6,277,989 B1 | 8/2001 | Chakravarty et al. | |
| 6,720,346 B2 * | 4/2004 | Chu et al. ............ | 514/370 |

FOREIGN PATENT DOCUMENTS

| | | |
|---|---|---|
| EP | 0 713 876 A1 | 5/1996 |
| EP | 0 639 574 B1 | 6/1998 |
| WO | WO 99/21845 | 5/1999 |
| WO | WO 00/12074 | 3/2000 |
| WO | WO 00/12497 | 3/2000 |
| WO | WO 00/25780 | 5/2000 |
| WO | WO 00/56738 | 9/2000 |
| WO | WO 00/62778 | 10/2000 |
| WO | WO 01/27089 | 4/2001 |
| WO | WO 01/34605 | 5/2001 |
| WO | WO 01/56567 | 8/2001 |
| WO | WO 02/24200 | 3/2002 |
| WO | WO 02/40486 | 5/2002 |
| WO | WO 02/057261 | 7/2002 |
| WO | WO 03/002544 | 1/2003 |
| WO | WO 03/004467 | 1/2003 |
| WO | WO 03/032970 | 4/2003 |
| WO | WO 03/032971 | 4/2003 |
| WO | WO 03/032972 | 4/2003 |
| WO | WO 03/032980 | 4/2003 |
| WO | WO 03/032986 | 4/2003 |
| WO | WO 03/032987 | 4/2003 |
| WO | WO 03/033457 | 4/2003 |
| WO | WO 03/033482 | 4/2003 |
| WO | WO 03/033483 | 4/2003 |
| WO | WO 2004/010995 | 2/2004 |

OTHER PUBLICATIONS

Henry et al., "p38 Mitogen-activated Protein Kinase as a Target for Drug Discovery," Drugs Fut., 24:1345-1354 (1999).
Salituro et al., "Inhibitors of p38 MAP Kinase: Therapeutic Intervention in Cytokine-Mediated Diseases," Curr. Med. Chem., 6:807-823 (1999).
Rankin et al., "The Terapeutic Effects of an Engineered Human Anti-tumour Necrosis Factor Alpha Antibody (CDP571) in Rheumatoid Arthritis," Br. J. Rheumatol., 34:334-342 (1995).
Moreland et al., "Etanercept Therapy in Rheumatoid Arthritis," Ann. Intern. Med., 130:478-486 (1999).
Han J, Richter B, Li Z, Kravchenko V, Ulevitch RJ. "Molecular cloning of human p38 MAP kinase," Biochim Biophys Acta. 1995;1265(2-3):224-7.
Jiang Y, Chen C, Li Z, Guo W, Gegner JA, Lin S, Han J. "Characterization of the structure and function of a new mitogen-activated protein kinase (p38beta)," J. Biol. Chem. Jul. 26, 1996;271(30):17920-6.
Li, Z.; Jiang, Y.; Ulevitch, R. J.; Han, J. "The primary structure of p38-gamma: a new member of p38 group of MAP kinases." Biochem. Biophys. Res. Commun. 228: 334-340, 1996.

(Continued)

*Primary Examiner*—Taofiq A Solola
(74) *Attorney, Agent, or Firm*—Sophie Binet Cross

(57) ABSTRACT

Provided are 5-membered heterocycle-based p38 kinase, including p38α and p38β kinase, inhibitors. Pharmaceutical compositions containing the compounds are also provided. Methods of use of the compounds and compositions are also provided, including methods of treatment, prevention, or amelioration of one or more symptoms of p38 kinase mediated diseases and disorders, including, but not limited to, inflammatory diseases and disorders.

46 Claims, No Drawings

OTHER PUBLICATIONS

Wang, et al., "Molecular Cloning and Characterization of a Novel p38 Mitogen-activated Protein Kinase," J. Biol. Chem. Sep. 19, 1997;272(38):23668-74.

Nogrady (1985) "Medicinal Chemistry A Biochemical Approach," Oxford University Press, New York, pp. 388-392.

Ceccarelli, S. et al, "Imidazo(1, 2-a)quinoxalin-4-amines: A Novel Class of Nonxanthine AI Adenosine Receptor Antagonists," European Journal of Medicinal Chemistry vol. 33, (1998), at pp. 943-955.

Murali Dhar, et al., "A Survey of Cyclic Replacements for the Central Diamide Moiety of Inhiboros of Inosine Monophosphate Dehydrogenase," Bioorg. Med. Chem. Letters 12: 3125-3128 (2002).

Zhao et al., "A new facile synthesis of 2-aminothiazole-5-carboxylates," Tetrahedron Lett., 42: 2101-2102 (2001).

Gabriele et al., "Stereoselective Synthesis of (E)-3-(Methoxycarbonyl)methylene-1,3-dihydroindol-2-ones by Palladium-Catalyzed Oxidative Carbonylation of 2-Ethynylanilines," Eur. J. Org. Chem, 4607 (2001).

Lancelot et al., "Pyrrolo[1,2-d]triazines-1,2,4. II. Etude des pyrrolo[1,2-d]triazinones-1 et -4," J. Heterocyclic Chem. 17, 631 (1980).

Frenzen et al., "Thermisch induzierte formale [3+2]-Cycloadditionen von 3,3- Dimethoxycyclopropen and Triazine, eine neue Synthese von Pyrrolo[1,2-d][1,2,4]triazinen," Chemische Berichte 126(10), 2317 (1993).

Sakai et al., "Synthesis of Mesomeric Betaines Containing a Pyrrolo- or Imidazotriaziniumolate System and Their Cycloaddition with Acetylenic Dipolarophiles Leading to Triazocinone Derivatives," Tetrahedron 55(48), 13703 (1999).

Komatsu et al., "Ring Englargement of Diaziridinone with 2-Substituted Pyrrole Leading to Bicyclic Triazine and Its Transformation to Nofvel Mesomeric Betaine," Journal of Organic Chem. 58(24), 6620 (1993).

Robba et al., "Etude D' une Nouvelle Synthese du Cycle Pyrrolo [1,2-d]-as-trazinique," Tetrahedron Letters 35, 3239 (1973).

Gebel et al., "Photoisomerization of 2-(Hept-6-enyl)cyclopent-12-enones to Tricyclo[7.3.0.0$^{1,7}$]dodecan-12-ones," Journal of Chemical Research, Synopses 1, 2 (1997).

Monge Vega et al., "1-Hidrazino-pirrolo [1,2-d] [1.2.4] triazinas y Derivados. Preparacion y Estudio Preliminar de Sus Propiedades Antihipertensoras," Boletin de la Sociedad Quimica del Peru 53(3), 150 (1987).

Cress et al., "Pyrrolo[1,2-d]-as-triazine. A new Heteroaromatic System," Journal of the Chemical Society, Chemical Communications 2, 35 (1973).

Jaureguiberry et al., "Synthese de pyrrolo-[1.2-d] triazines," Comptes Rendus des Seances de l'Academie des Sciences, Series C: Sciences Chimiques 274(20), 1703 (1972).

Ansel Introduction to Pharmaceutical Dosage Forms, Fourth Edition 1985, 126.

Lisnock et al., "Molecular Basis for p38 Protein Kinase Inhibotor Specificity," Biochemistry, 37:16573-16581 (1998).

Chen et al., "Kenetic Mechanism of the p38-α MAP Kinase: Phosphoryl Transfer to Synthetic Peptides," Biochemistry, 39:2079-2087 (2000).

Fox et al., "A single amino acid substitution makes ERK2 susceptible to pyridinyl imidazole inhibitors of p38 MAP kinase," Protein Sci., 7:2249-2255 (1998).

Calarusso et al., "Phenethyl Amides as Novel Noncovalent Inhibitors of Hepatitis C Virus NS3/4A Protease: Discovery, Initial SAR, and Molecular Modeling," J. Med. Chem., 46:345-348 (2003).

Raingeaud et al., "MKK3- and MKK6-Regulated Gene Expression is Mediated by the p38 Mitogen-Activated Protein Kinase Signal Transduction Pathway," Mol. Cell. Biol. 1247-1255 (1996).

Boehm et al., "New Inhibitors of p38 Kinase," Exp. Opin. Ther. Patents 10(1):25-37 (2000).

Chemical Abstracts Abstr. No. 1973:546496, Document No. 79:146496 (1973).

Chemical Abstracts Abstr. No. 1972:461962, Document No. 77:61962 (1972).

* cited by examiner

P-38 INHIBITORS

RELATED APPLICATIONS

Priority is claimed herein under 35 U.S.C. §119(e) to U.S. provisional patent application Ser. Nos. 60/475,662, filed Jun. 3, 2003, and 60/531,541, filed Dec. 19, 2003, entitled "P-38 INHIBITORS." The disclosures of the above-referenced provisional applications are incorporated herein by reference in their entirety.

FIELD

Provided herein are aminoaryl substituted 5-membered heterocyclic compounds which have cytokine inhibitory activity. Also provided are the uses of aminoaryl substituted 5-membered heterocyclic compounds for treating conditions associated with p38α and β kinases and for treating p38 kinase-associated conditions.

BACKGROUND

A large number of cytokines participate in the inflammatory response, including IL-1, IL6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others (Henry et al., *Drugs Fut.*, 24:1345-1354 (1999); Salituro et al., *Curr. Med. Chem.*, 6:807-823 (1999)). Evidence in human patients indicates that protein antagonists of cytokines are effective in treating chronic inflammatory diseases, such as, for example, monoclonal antibody to TNF-α (Remicade) (Rankin et al., *Br. J. Rheumatol.*, 34:334-342 (1995)), and soluble TNF-α receptor-Fc fusion protein (Etanercept) (Moreland et al., 25 *Ann. Intern. Med.*, 130:478-486 (1999)).

The biosynthesis of TNF-α occurs in many cell types in response to an external stimulus, such as, for example, a mitogen, an infectious organism, or trauma. Important mediators of TNF-α production are the mitogen-activated protein (MAP) kinases, and in particular, p38 kinases. These kinases are activated in response to various stress stimuli, including but not limited to proinflammatory cytokines, endotoxin, ultraviolet light, and osmotic shock. Activation of p38 requires dual phosphorylation by upstream MAP kinase kinases (MKK3 and MKK6) on threonine and tyrosine within a Thr-Gly-Tyr motif characteristic of p38 isozymes.

There are four known isoforms of p38, i.e., p38 α, p38β, p38γ, and p38δ. The α and β isoforms are expressed in inflammatory cells and are key modulators of TNF-α production. Inhibiting the p38α and β enzymes in cells results in reduced levels of TNF-α expression. Also, administering inhibitors of p38α and β in animal models of inflammatory disease has proven that such inhibitors are effective in treating those diseases. Accordingly, the p38 enzymes serve an important role in inflammatory processes mediated by IL-1 and TNF-α. Compounds that reportedly inhibit p38 kinase and cytokines such as IL-1 and TNF-α for use in treating inflammatory diseases are disclosed in U.S. Pat. Nos. 6,277,989 and 6,130,235 to Scios, Inc; U.S. Pat. Nos. 6,147,080 and 5,945, 418 to Vertex Pharmaceuticals Inc; U.S. Pat. Nos. 6,251,914, 5,977,103 and 5,658,903 to Smith-Kline Beecham Corp.; U.S. Pat. Nos. 5,932,576 and 6,087,496 to G.D. Searle & Co.; WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

Pyrrolotriazine compounds useful as tyrosine kinase inhibitors are disclosed in U.S. patent application Ser. No. 09/573,829 filed May 18, 2000, assigned to Bristol-Myers Squibb. In addition, pyrrolotriazine kinase inhibitors are disclosed in WO 02/40486, assigned to Bristol-Myers Squibb. Recent applications: WO 03/032970, WO 03/033482, WO03/ 032971, WO 03/032986, WO 03/032980, WO 03/032987, WO 03/033483, WO 03/033457 and WO 03/032972 are incorporated into this application. A series of aminoaryl substituted 5- and 6-membered ring heterocycles useful as inhibitors of EIPH are disclosed in WO 00/25780. Each of the patent applications, patents, and publications referred to herein is incorporated herein by reference.

SUMMARY

Compounds for use in compositions and methods for modulating the activity of cytokines are provided. In one embodiment, the compounds are used in compositions and methods for modulating p38 kinase, including, but not limited to p38α and p38β kinase activity. In certain embodiments, the compounds are heterocyclic compounds that are substituted with a cycloalkylamide moiety. In certain embodiments, the compounds provided herein are substituted aminothiazoles.

Provided herein are compounds of formula I:

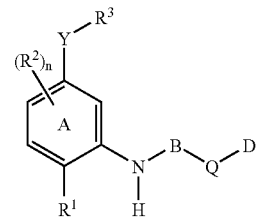

or pharmaceutically acceptable derivatives thereof, wherein:

$R^1$ is hydrogen, methyl, halo, hydroxyl, lower alkyl, lower cycloalkyl, lower alkynyl, trifluoromethyl, methoxy, trifluoromethoxy, cyano, —$NH_2$, —$NR^4R^5$ or —$OR^4$;

$R^2$ is attached to any available carbon atom of the phenyl ring A and at each occurrence is independently selected from alkyl, substituted alkyl, lower cycloalkyl, halo, trifluoromethyl, trifluoromethoxy, —$OR^4$, —CN, —$NR^4R^5$; —S(=O) alkyl, —S(=O)aryl, —$NHSO_2$-arylene-$R^4$, —$NHSO_2$alkyl, —$CO_2R^4$, —$CONH_2$, —$SO_3H$, —S(O)alkyl, —S(O)aryl, —$SO_2NHR^4$, and —NHC(=O)$NHR^4$;

n is 0, 1 or 2;

$R^3$ is selected from hydrogen, alkyl, —$OR^4$, substituted alkyl, cycloalkyl, —$CR^4$cycloalkyl, heteroaryl, substituted heteroaryl, heterocycle and substituted heterocycle;

Y is a single bond, —C(=O)NH—, —NH(C=O)—, —NH(C=O)NH—, —$SO_2NH$—, —$NHSO_2$—, —C(=O)—;

Z is $NR^4$, S or O;

B is a 5-membered heterocyclic ring system optionally substituted with up to two $R^{13}$;

Q is independently selected from a single bond, —O—, —S—, —$NR^4$—, —S(O)—, —$SO_2$—, —C(O)—, —CO (O)—, —C(O)NH—($C_{0-4}$alkyl)- or —$CH_2$—;

D is a monocyclic or bicyclic ring system optionally containing up to four heteroatoms selected from N, O, and S, and wherein a $CH_2$ adjacent to any of the said N, O or S heteroatoms is optionally substituted with oxo (=O) or D is $C_{1-6}$alkyl, and wherein D is optionally substituted by one to four $(CR^9R^{10})_w E$ groups;

w is an integer having a value from 0-4;

$R^{10}$ is selected from H, $C_1$-$C_4$ alkylhydroxy, $C_1$-$C_4$alkylaryl and $C_1$-$C_4$alkylheteroaryl, wherein said aryl or heteroaryl group is unsubstituted or substituted with 1-3 groups independently selected from halo, $NO_2$, $C_1$-$C_4$alkyl, $C_3$-$C_{10}$cycloalkyl, $C_2$-$C_6$alkenyl, $C_2$-$C_6$alkynyl, haloalkyl, haloalkoxy, OH, $C_1$-$C_4$alkoxy, $C_1$-$C_4$alkylcarbonyl, CN, $NH_2$, $NR^6R^7$, $SR^6$, $S(O)R^6$, $SO_2R^6$, $SO_3R^6$, $SO_2NR^6$, $CO_2H$, $CO_2R^6$, and $CONR^6R^7$;

E is selected from H, halogen, $NO_2$, $C_1$-$C_4$alkyl, $C_3$-$C_{10}$cycloalkyl, $C_2$-$C_6$alkenyl, $C_2$-$C_6$ alkynyl, haloalkyl, haloalkoxy, OH, $OR^6$, CN, CHO, $CO_2R^6$, $CONR^6R^7$, $OCOR_6$, $OC(=O)OR^6$, $OC(=O)NR^6R^7$, $OCH_2CO_2R^6$, $C(=O)R^6$, $NH_2$, $NHR^6$, $NR^6R^7$, $NR^7C(=O)R^6$, $NR^7C(=O)OR^6$, $NR^7C(=O)C(=O)OR^6$, $NR^7C(=O)C(=O)NR^6R^7$, $NR^7C(=O)C(=O)(C_1-C_6alkyl)$, $NR^7C(=NCN)OR^6$, $NR^7C(=O)NR^6R^7$, $NR^7C(=NCN)NR^6R^7$, $NR^7C(=NR^6)NR^7R^8$ $NR^6SO_2NR^6R^7$, $NR^7SO_2R^6$, $SR^6$, $S(=O)R^6$, $SO_2R^6$, $SO_3R^7$, $SO_2NR^6R^7$, NHOH, NHOR$^6$, $NR^6NR^7R^8$, $N(COR^6)OH$, $N(CO_2R^6)OH$, $CONR^7(CR^9R^{10})_rR^6$, $CO(CR^9R^{10})_pO(CHR^9)_qCO_2R^6$, $CO(CR^9CR^{10})_rR^6$, $CO(CR^9R^{10})_p$ $O(CR^9R^{10})_pO(CHR^9)_qCO^2R_6$, $CO(CR^9CR^{10})_pOR^6$, $CO(CR^9R^{10})_pO(CR^9R^{10})_qR^6$, $CO(CR^6CR^{10})_rNR^6R^7$, $OC(O)O(CR^9R^{10})_mNR^6R^7$, $O(CO)_n$ $(CR^9R^{10})_rR^6$, $O(CR^9R^{10})_mNR^6R^7_mNR^7C(O)(CR^9R^{10})_rOR^6$, $NR^7C(=NC)(CR^9R^{10})_rR^6$, $NR^7CO(CR^9R^{10})_rNR^6R^7$, $NR^7(CR^9R^{10})_mOR^6$, $NR^7(CR^9R^{10})_rCO_2R^6$, $NR^7(CR^9R^{10})_mNR^6R^7$, $NR^7$, $NR^3(CR^9R^{10})_n$ $SO_2(CR^9R^{10})_rCO_2R^6$, $NR^7(CR^9R^{10})_mNR^6R^7$, $NR^7$ $(CR^9R^{10})_nSO_2(CR^9R^{10})_qR^6$, $CONR^7(CR^9R^{10})_nSO_2$ $(CR^9R^{10})_qR^6$, $SO_2NR^7(CR^9R^{10})_qR^6$, $SO_2NR^6$ $(CR^9R^{10})_mOR^6$, $C_2$-$C_6$alkenyl, $C_3$-$C_{10}$cycloalkyl, $C_3$-$C_{10}$cycloalkylmethyl, aryl, heterocyclic optionally substituted with one or two alkyl groups, heteroaryl optionally substituted with one or two alkyl groups and alkylaryl, wherein said aryl groups are unsubstituted or substituted with 1 or 2 substituents each independently selected from $R^{12}$;

m is an integer having a value from 2-6;

p is an integer having a value from 1-3;

q is an integer having a value from 0-3;

r is an integer having a value from 0-6;

$R^{12}$ at each occurrence is independently selected from halo, $NO_2$, $C_1$-$C_4$alkyl, $C_3$-$C_{10}$cycloalkyl, $C_2$-$C_6$alkenyl, $C_2$-$C_6$alkynyl, haloalkyl, haloalkoxy, OH, oxo, $C_1$-$C_4$alkoxy, $OR^6$, $O(CR^9R^{10})CO_2R^6$, $O(CR^9R^{10})_mNR^6R^7$, $O(CR^9R^{10})_pCN$, $O(CR^9R^{10})_rC(=O)NR^6R^7$, $C_1$-$C_4$alkylcarbonyl, CN, $NH_2$, $NHR^6$, $NR^6R^7$, $NR^7$ $(CR^9R^{10})CO_2R^6$, $NR^7OR^6$, $NR^7(CR^9R^{10})_mOR^6$, $NR^7CH$ $((CR^9R^{10})_pOR^6)_2$, $NR^7C((CR^9R^{10})_pOR^6)_3$, $NR^7C(=O)R^6$, $NR^7(CR^9R^{10})_mNR^6R^7$, $NR^7(CR^9R^{10})_qR^6$, $SR^7$, $S(O)R^7$, $SO_2R^7$, $SO_2NR^6$, $SO_3R^7$, $CO_2H$, $CO_2R^6$, and $CONR^6R^7$;

$R^4$ is hydrogen, lower alkyl and lower cycloalkyl;

$R^5$ is hydrogen, lower alkyl and lower cycloalkyl;

$R^6$, $R^7$ and $R^8$ are independently selected as follows:

i) $R^6$, $R^7$ and $R^8$ are independently selected from H, $C_1$-$C_6$alkyl, $C_3$-$C_{10}$cycloalkyl, $C_2$-$C_6$alkenyl, $C_2$-$C_6$alkynyl, $C_1$-$C_6$alkylcarbonyl, $C_3$-$C_7$cycloalkyl $(C_0$-$C_5$alkyl)carbonyl, $C_1$-$C_6$alkoxycarbonyl, aryl($C_0$-$C_5$alkyl)carbonyl, aryl($C_1$-$C_5$alkoxy)carbonyl, heterocyclic($C_0$-$C_5$alkyl)carbonyl, heterocyclic($C_1$-$C_5$alkoxy)carbonyl, $C_1$-$C_6$alkylsulfonyl, arylsulfonyl, heteroarylsulfonyl, $C_0$-$C_4$alkylaryl, $C_0$-$C_4$alkylheterocyclic, wherein said cycloalkyl, aryl, or heterocyclic groups are unsubstituted or substituted with 1 or 2 substituents each independently selected from the group consisting of $C_1$-$C_4$alkyl, hydroxyl, $C_1$-$C_4$alkoxy, F, Cl, Br, haloalkyl, $NO_2$ and CN; or, ii) $R^6$ and $R^7$, or $R^6$ and $R^8$, or $R^7$ and $R^8$, when both substituents are on the same nitrogen atom (as in ($-NR^6R^7$) or ($-N^7R^8$)), can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, 1-piperazinyl, 1-imidazolyl, 3-azabicyclo(3,2,2)nonan-3yl, and 1-tetrazolyl, the said heterocycle being optionally substituted with 1-3 groups each independently selected from oxo, $C_0$-$C_4$alkylOH, $C_0$-$C_4$alkylOC$_1$-$C_4$alkyl, $C_0$-$C_4$alkylCONH$_2$, $C_0$-$C_4$alkylCO$_2$C$_0$-$C_4$alkyl, $C_1$-$C_4$alkyl, $C_1$-$C_4$alkoxy, $C_3$-$C_7$cycloalkyl, $C_0$-$C_6$alkylcarbonyl, $C_3$-$C_7$cycloalkylcarbonyl, $C_1$-$C_6$alkoxycarbonyl, $C_3$-$C_7$cycloalkoxycarbonyl, —NHCOalkyl, aryl, heteroaryl, arylalkoxycarbonyl, heteroarylalkoxycarbonyl, $C_1$-$C_6$alkylsulfonyl, arylsulfonyl and heteroarylsulfonyl;

$R^9$ is hydrogen or $C_1$-$C_4$alkyl; and $R^{13}$ is hydrogen, alkyl, haloalkyl, aminocarbonyl, hydroxycarbonyl, alkoxycarbonyl, cycloalkylalkylaminocarbonyl, substituted alkyl, aryl, substituted aryl, heteroaryl, heterocyclyl, alkylthio, alkylaminocarbonyl or lower cycloalkyl; where the substituents on alkyl group are selected from one to four substituents selected from halo, hydroxy, alkoxy, oxo (=O), alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and substituted or unsubstituted heterocycles, such as indolyl, imidazolyl, furyl, thienyl, thiazolyl, pyrrolidyl, pyridyl, pyrimidyl and the like and the substituents on aryl group are selected from one to four substituents selected from alkyl, substituted alkyl, haloalkyl, halo, trifluoromethoxy, trifluoromethyl, hydroxy, hydroxyalkyl, aminoalkyl, alkoxy, alkanoyl, alkanoyloxy, amino, arylamino, aralkylamino, dialkylamino, alkanoylamino, thiol, alkylthio, ureido, nitro, cyano, cyanoalkyl, heterocyclyl, carboxy, carboxyalkyl, carbamyl, alkoxycarbonyl, aminocarbonyl, alkylthiono, arylthiono, arylsulfonylamine, sulfonic acid, alkysulfonyl, sulfonamido, aryloxy and $CONR^aR^b$, where $R^a$ and $R^b$ are selected from hydrogen, alkyl, alkenyl, alkynyl, cycloalkyl, alkoxycarbonylaminoalkyl and alkylamino; or $R^a$ and $R^b$ together with the nitrogen on which they are substituted, form a 3-6 membered heterocyclic or heteroaryl ring. The substituent may be further substituted by hydroxy, alkyl, alkoxy, aryl, substituted aryl, substituted alkyl or aralkyl.

The groups A, Y, $R^1$, $R^2$, $R^3$, B, Q and D are selected such that the resulting compound has effect on cytokine activity.

Also of interest are any pharmaceutically-acceptable derivatives, including salts, esters, enol ethers, enol esters, solvates, hydrates and prodrugs of the compounds described herein. Pharmaceutically-acceptable salts, include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-parachlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc, aluminum, and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates.

Pharmaceutical compositions formulated for administration by an appropriate route and means containing effective concentrations of one or more of the compounds provided herein, or pharmaceutically acceptable derivatives thereof, that deliver amounts effective for the treatment, prevention, or amelioration of one or more symptoms of diseases or disorders that are modulated or otherwise affected by cytokine activity, in one embodiment, p38 kinase activity, or in which cytokine activity, in one embodiment, p38 kinase activity is implicated, are also provided. The effective amounts and concentrations are effective for ameliorating any of the symptoms of any of the diseases or disorders.

Methods for treatment, prevention, or amelioration of one or more symptoms of diseases or disorders mediated by or in which cytokine activity, in one embodiment, p38 kinase activity, is implicated, are provided. Such methods include methods of treatment, prevention and amelioration of one or more symptoms of inflammatory diseases, autoimmune diseases, destructive bone disorders, proliferative disorders, angiogenic disorders, infectious diseases, neurodegenerative diseases, and viral diseases, using one or more of the compounds provided herein, or pharmaceutically acceptable derivatives thereof.

Methods of modulating the activity of cytokines, in one embodiment, the activity of p38 kinases, using the compounds and compositions provided herein are also provided.

Methods of reducing the expression of inducible pro-inflammatory proteins, including, but not limited to prostaglandin endoperoxide synthase-2 (PGHS-2), also referred to as cyclooxygenase-2 (COX-2), in a subject in need thereof by administration of one or more compounds or compositions provided herein are also provided.

In practicing the methods, effective amounts of the compounds or compositions containing therapeutically effective concentrations of the compounds, which are formulated for systemic delivery, including parenteral, oral, or intravenous delivery, or for local or topical application, for the treatment of cytokine, in one embodiment, p38 kinase, mediated diseases or disorders, or diseases or disorders in which cytokine activity, in one embodiment, p38 kinase activity, is implicated, including, but not limited to, inflammatory diseases, autoimmune diseases, destructive bone disorders, proliferative disorders, angiogenic disorders, infectious diseases, neurodegenerative diseases, and viral diseases, are administered to an individual exhibiting the symptoms of these diseases or disorders. The amounts are effective to ameliorate or eliminate one or more symptoms of the diseases or disorders.

Articles of manufacture containing packaging material, a compound or composition, or pharmaceutically acceptable derivative thereof, provided herein, which is effective for modulating the activity cytokines, in one embodiment, p38 kinases, or for treatment, prevention or amelioration of one or more symptoms of cytokine, in one embodiment, p38 kinase, mediated diseases or disorders, or diseases or disorders in which cytokine activity, in one embodiment, p38 kinase activity, is implicated, within the packaging material, and a label that indicates that the compound or composition, or pharmaceutically acceptable derivative thereof, is used for modulating the activity of cytokine, in one embodiment, the activity of p38 kinases, or for treatment, prevention or amelioration of one or more symptoms of cytokine, in one embodiment, p38 kinase, mediated diseases or disorders, or diseases or disorders in which cytokine activity, in one embodiment, p38 kinase activity, is implicated, are provided.

DETAILED DESCRIPTION OF EMBODIMENTS

A. Definitions

Unless defined otherwise, all technical and scientific terms used herein have the same meaning as is commonly understood by one of ordinary skill in the art. All patents, applications, published applications and other publications are incorporated by reference in their entirety. In the event that there are a plurality of definitions for a term herein, those in this section prevail unless stated otherwise.

As used herein, p38α refers to the enzyme disclosed in Han J, Richter B, Li Z, Kravchenko V, Ulevitch R J. Molecular cloning of human p38 MAP kinase. Biochim Biophys Acta. 1995;1265(2-3):224-7. As used herein, p38β refers to the enzyme disclosed in Jiang Y, Chen C, Li Z, Guo W, Gegner J A, Lin S, Han J. Characterization of the structure and function of a new mitogen-activated protein kinase (p38beta).J. Biol. Chem. 1996 Jul. 26;271(30):17920-6. As used herein, p38γ refers to the enzyme disclosed in Li, Z.; Jiang, Y.; Ulevitch, R. J.; Han, J.: The primary structure of p38-gamma: a new member of p38 group of MAP kinases. *Biochem. Biophys. Res. Commun.* 228: 334-340, 1996. As used herein, p38δ refers to the enzyme disclosed in *Molecular Cloning and Characterization of a Novel p38 Mitogen-activated Protein Kinase*, Xuhong Sunny Wang, Katrina Diener, Carl L. Manthey, Shen-wu Wang, Bradley Rosenzweig, Jeffrey Bray, John Delaney, Craig N. Cole, Po-Ying Chan-Hui, Nathan Mantlo, Henri S. Lichenstein, Mark Zukowski and Zhengbin Yao.

The term "p38-associated condition", as used herein means any disease or condition in which p38 is known to play a role. This includes, conditions which are known to be caused by IL-1, TNF, IL-6 or IL-8 overproduction. Such conditions include, but are not limited to, inflammatory diseases, autoimmune diseases, destructive bone disorders, proliferative disorders, infectious diseases, viral disease, and neurodegenerative diseases.

As used herein, pharmaceutically acceptable derivatives of a compound include salts, esters, enol ethers, enol esters, acetals, ketals, orthoesters, hemiacetals, hemiketals, acids, bases, solvates, hydrates or prodrugs thereof. Such derivatives may be readily prepared by those of skill in this art using known methods for such derivatization. The compounds produced may be administered to animals or humans without substantial toxic effects and either are pharmaceutically active or are prodrugs. Pharmaceutically acceptable salts include, but are not limited to, amine salts, such as but not limited to N,N'-dibenzylethylenediamine, chloroprocaine, choline, ammonia, diethanolamine and other hydroxyalkylamines, ethylenediamine, N-methylglucamine, procaine, N-benzylphenethylamine, 1-para-chlorobenzyl-2-pyrrolidin-1'-ylmethylbenzimidazole, diethylamine and other alkylamines, piperazine and tris(hydroxymethyl)aminomethane; alkali metal salts, such as but not limited to lithium, potassium and sodium; alkali earth metal salts, such as but not limited to barium, calcium and magnesium; transition metal salts, such as but not limited to zinc; and other metal salts, such as but not limited to sodium hydrogen phosphate and disodium phosphate; and also including, but not limited to, salts of mineral acids, such as but not limited to hydrochlorides and sulfates; and salts of organic acids, such as but not limited to acetates, lactates, malates, tartrates, citrates, ascorbates, succinates, butyrates, valerates and fumarates. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids. Pharmaceutically acceptable enol ethers include, but are not limited to, derivatives of formula C═C(OR) where R is hydrogen, alkyl, alkenyl, alkynyl, aryl, heteroaryl, aralkyl, heteroaralkyl, cycloalkyl ar heterocyclyl. Pharmaceutically acceptable enol esters include, but are not limited to, derivatives of formula C═C(OC(O)R) where R is hydrogen, alkyl, alkenyl, alkynyl, aryl, heteroaryl, aralkyl, heteroaralkyl, cycloalkyl ar heterocyclyl. Pharmaceutically acceptable solvates and hydrates are complexes of a compound with one or more solvent or water molecules, or 1 to about 100, or 1 to about 10, or one to about 2, 3 or 4, solvent or water molecules.

As used herein, the terms "treating" or "treatment" encompass either or both responsive and prophylaxis measures, e.g., designed to inhibit or delay the onset of the disease or disorder, achieve a full or partial reduction of the symptoms or disease state, and/or to alleviate, ameliorate, lessen, or cure the disease or disorder and/or its symptoms. Treatment also encompasses any pharmaceutical use of the compositions herein, such as use for treating a P-38 kinase mediated diseases or disorders.

As used herein, amelioration of the symptoms of a particular disorder by administration of a particular compound or pharmaceutical composition refers to any lessening, whether permanent or temporary, lasting or transient that can be attributed to or associated with administration of the composition.

As used herein inhibition of p-38α/βkinase means either p38α and/or p38β kinase are inhibited. Thus, reference to an $IC_{50}$ value for inhibiting p-38α/β kinase means that the compound has such effectiveness for inhibiting at least one of, or both of, p38α and p38β kinases.

As used herein, the $IC_{50}$ refers to an amount, concentration or dosage of a particular test compound that achieves a 50% inhibition of a maximal response, such as modulation of p-38 kinase activity, in an assay that measures such response.

As used herein, $EC_{50}$ refers to a dosage, concentration or amount of a particular test compound that elicits a dose-dependent response at 50% of maximal expression of a particular response that is induced, provoked or potentiated by the particular test compound.

As used herein, a prodrug is a compound that, upon in vivo administration, is metabolized by one or more steps or processes or otherwise converted to the biologically, pharmaceutically or therapeutically active form of the compound. To produce a prodrug, the pharmaceutically active compound is modified such that the active compound will be regenerated by metabolic processes. The prodrug may be designed to alter the metabolic stability or the transport characteristics of a drug, to mask side effects or toxicity, to improve the flavor of a drug or to alter other characteristics or properties of a drug. By virtue of knowledge of pharmacodynamic processes and drug metabolism in vivo, those of skill in this art, once a pharmaceutically active compound is known, can design prodrugs of the compound (see, e.g., Nogrady (1985) *Medicinal Chemistry A Biochemical Approach*, Oxford University Press, New York, pages 388-392).

It is to be understood that the compounds provided herein may contain chiral centers. Such chiral centers may be of either the (R) or (S) configuration, or may be a mixture thereof. Thus, the compounds provided herein may be enantiomerically pure, or be stereoisomeric or diastereomeric mixtures.

As used herein, substantially pure means sufficiently homogeneous to appear free of readily detectable impurities as determined by standard methods of analysis, such as thin layer chromatography (TLC), gel electrophoresis, high performance liquid chromatography (HPLC) and mass spectrometry (MS), used by those of skill in the art to assess such purity, or sufficiently pure such that further purification would not detectably alter the physical and chemical properties, such as enzymatic and biological activities, of the substance. Methods for purification of the compounds to produce substantially chemically pure compounds are known to those of skill in the art. A substantially chemically pure compound may, however, be a mixture of stereoisomers. In such instances, further purification might increase the specific activity of the compound. The instant disclosure is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "alkyl" refers to straight or branched chain unsubstituted hydrocarbon groups of 1 to 20 carbon atoms, in one embodiment, 1 to 7 carbon atoms. The expression "lower alkyl" refers to unsubstituted alkyl groups of 1 to 4 carbon atoms. When a subscript is used with reference to an alkyl or other group, the subscript refers to the number of carbon atoms that the group may contain. The term "$C_{0-4}$alkyl" includes a bond and alkyl groups of 1 to 4 carbon atoms.

The term "substituted alkyl" refers to an alkyl group substituted by one to four substituents selected from halo, hydroxy, alkoxy, oxo (═O), alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino and substituted or unsubstituted heterocycles, such as indolyl, imidazolyl, furyl, thienyl, thiazolyl, pyrrolidyl, pyridyl, pyrimidyl and the like. Where the substituent on the alkyl is further substituted, it will be with alkyl, alkoxy, aryl, or aralkyl.

When the term alkyl is used in connection with another group, as in heterocycloalkyl or cycloalkylalkyl, this means the identified group is bonded directly through an alkyl group which may be branched or straight chain. In the case of substituents, as in "substituted cycloalkylalkyl," the alkyl portion of the group may, besides being branched or straight chain, be substituted as recited above for substituted alkyl groups and/or the connected group may be substituted as recited herein for that group.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups. When the aryl is substituted, each ring of the aryl may be substituted.

The term "substituted aryl" refers to an aryl group substituted by one to four substituents selected from alkyl, substituted alkyl, haloalkyl, halo, trifluoromethoxy, trifluoromethyl, hydroxy, hydroxyalkyl, aminoalkyl, alkoxy, alkanoyl, alkanoyloxy, amino, arylamino, aralkylamino, dialkylamino, alkanoylamino, thiol, alkylthio, ureido, nitro, cyano, cyanoalkyl, carboxy, carboxyalkyl, carbamyl, alkoxycarbonyl, aminocarbonyl, alkylthiono, arylthiono, arylsulfonylamine, sulfonic acid, alkysulfonyl, sulfonamido, aryloxy and $CONR^aR^b$, where $R^a$ and $R^b$ are selected from hydrogen, alkyl, alenyl, alynyl, cycloalkyl and alkylamino; or $R^a$ and $R^b$ together with the nitrogen on which they are substituted for a 3-6 membered heterocyclic or heteroaryl ring. The substituent may be further substituted by hydroxy, alkyl, alkoxy, aryl, substituted aryl, substituted alkyl or aralkyl.

The term "aralkyl" refers to an aryl group bonded directly through an alkyl group, such as benzyl, wherein the alkyl group may be branched or straight chain. In the case of a "substituted aralkyl," the alkyl portion of the group may, besides being branched or straight chain, be substituted as recited above for substituted alkyl groups and/or the aryl portion may be substituted as recited for substituted aryl:

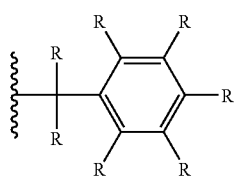

Thus, the term "optionally substituted benzyl" refers to the group wherein each R group may be hydrogen or may also be selected from alkyl, halogen, cyano, nitro, amino, hydroxy, allcoxy, alkylthio, phenyl, benzyl, phenyloxy, and benzyloxy, and other groups recited above. At least two of these "R" groups should be hydrogen and in one embodiment, at least five of the "R" groups are hydrogen. In certain embodiments, the benzyl group is

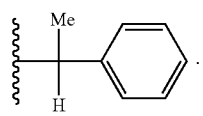

The term "heteroaryl" refers to an aromatic group for example, which is a 4 to 7 membered monocyclic, 7 to 11 membered bicyclic, or 10 to 15 membered tricyclic ring system, which has at least one heteroatom and at least one carbon atom containing ring. Each ring of the heteroaryl group containing a heteroatom can contain one or two oxygen or sulfur atoms and/or from one to four nitrogen atoms, provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfuir atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring.

A "substituted heteroaryl" has one to four substituents on any one or more of the rings pomprising the heterary1 group. The substituents may be selected from those 30 recited below for heterocycle groups.

Exemplary monocyclic heteroaryl groups include pyrrolyl, pyrazolyl, pyrazolinyl, imidazolyl, oxazolyl, isoxazolyl, thiazolyl, i e.,

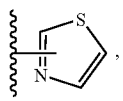

thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzopuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "alkenyl" refers to straight or branched chain hydrocarbon groups of 2 to 20 carbon atoms, in certain embodiments, 2 to 15 carbon atoms, and in other embodiments, 2 to 8 carbon atoms, having one to four double bonds.

The term "substituted alkenyl" refers to an alkenyl group substituted by one to two substituents selected from halo, hydroxy, alkoxy, alkanoyl, alkanoyloxy, amino, alkylamino, diallcylamino, alkanoylamino, thiol, alkylthio, alkylthiono, alkylsulfonyl, sulfonamido, nitro, cyano, carboxy, carbamyl, substituted carbamyl, guanidino, and substituted and unsubstituted heterocycles, including indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, in certain embodiments, 2 to 15 carbon atoms, and in other embodiments, 2 to 8 carbon atoms, having one to four triple bonds.

The term "substituted alkynyl" refers to an alkynyl group substituted by a substituent selected from halo, hydroxy, alkoxy, alkanoyl, alkanoyloxy, amino, alkylamino, dialkylamino, alkanoylamino, thiol, alkylthio, alkylthiono, allcylsulfonyl, sulfonamido, nitro, cyano, carboxy, carbamyl, substituted carbamyl, guanidino and substituted or unsubstituted heterocyclo, e.g. imidazolyl, furyl, thienyl, thiazolyl, pyrrolidyl, pyridyl, pyrimidyl and the like.

The term "cycloalkyl" refers to a saturated or partially unsaturated nonaromatic cyclic hydrocarbon ring system, in certain embodiments, containing 1 to 3 rings and 3 to 7 carbons per ring which may be further fused with an unsaturated $C_3$-$C_7$ carbocylic ring. Exemplary groups include cyclopropyl, cyclobutyl, cyclopentyl, cyclohexyl, cycloheptyl, cycloctyl, cyclodecyl, cyclododecyl, and adamantyl. A "substituted cycloalkyl" is substituted with one or more alkyl or substituted alkyl groups as described above, or one or more groups described above as alkyl substituents. The expression "lower cycloalkyl" refers to an unsubstituted saturated or unsaturated nonaromatic cyclic hydrocarbon ring system containing 3 to 5 carbon atoms.

The terms "heterocycle", "heterocyclic" and "heterocyclo" each refer to a fully saturated or unsaturated, aromatic or nonaromatic cyclic group, for example, which is a 4 to 7 membered mono cyclic, 7 to 11 membered bicyclic, or 10 to 15 membered tricyclic ring system, which has at least one heteroatom in at least one carbon atom—containing ring. Thus, the term "heterocycle" includes heteroaryl groups as described above. Each ring of the heterocyclic group containing a heteroatom may have 1, 2 or 3 heteroatoms independently selected from nitrogen, oxygen or sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo(2,3-c)pyridinyl, furo(3,1-b)pyridinyl) or furo(2,3-b)pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofiuyl, dihydrobenzothienyl, dihydrobenzothiopyranyl, dihydrobenzothiopyranyl sulfone, dihydrobenzopyranyl, indolinyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Also included are smaller heterocycles, such as epoxides and aziridines.

A "substituted heterocycle" will be substituted with one or more alkyl or aralkyl groups as described above, and/or one or more groups described above as alkyl substituents.

Unless otherwise indicated, when reference is made to a specifically-named heterocyclo or heteroaryl, the reference is intended to include those systems having the maximum number of non-cumulative double bonds or less than that maximum number of double bonds. Thus, for example, the term "isoquinoline" refers to isoquinoline and tetrahydroisoquinoline. The term "diazepine" refers to a heterocyclo ring having at least one seven atom ring with two nitrogen atoms in the seven membered ring, including a fully saturated or unsaturated diazepine.

The term "heteroatoms" shall include oxygen, sulfur and nitrogen.

The term "haloalkyl" means an alkyl having one or more halo substituents

The term "perfluoromethyl" means a methyl group substituted by one, two, or three fluoro atoms, i.e., $CH_2F$, $CHF_2$ and $CF_3$. The term "perfluoroalkyl" means an alkyl group having from one to five fluoro atoms, such as pentafluoroethyl.

The term "haloalkoxy" means an alkoxy group having one or more halo substituents. For example, "haloalkoxy" includes —$OCF_3$.

The term "carbocyclic" means a saturated or unsaturated unsaturated monocyclic or bicyclic ring in which all atoms of all rings are carbon. Thus, the term includes cycloalkyl and aryl rings. The carbocyclic ring may be substituted in which case the substituents are selected from those recited above for cycloalkyl and aryl groups.

When the term "unsaturated" is used herein to refer to a ring or group, the ring or group may be fully unsaturated or partially unsaturated.

Definitions for the various other groups that are recited above in connection with substituted alkyl, substituted alkenyl, substituted alkynyl, substituted aryl, substituted heterocycle, substituted cycloalkyl, and so forth, are as follows: alkoxy is —OR, alkanoyl is —C(=O)$R^a$, aryloxy is —OAr, alkanoyloxy is —OC(=O)$R^a$, amino is —$NH_2$, alkylamino is NH$R^a$, arylamino is —NHAr, aralkylamino is NH—$R^b$—Ar, disubstituted amine or dialkylamino is N$R^c R^d$, alkanoylamino is —NH—C(=O)$R^a$, aroylamino is —NH—C(=O)Ar, aralkanoylamino is NH—C(=O)$R^b$—Ar, thiol is —SH, alkylthio is —S$R^a$, arylthio is —SAr, aralkylthio is —S—$R^b$—Ar, alkylthiono is —S(=O)$R^a$, arylthiono is —S(=O)Ar, aralkylthiono is —S(=O)$R^b$—Ar, alkylsulfonyl is —SO$_{(q)}R^a$, arylsulfonyl is —SO$_{(q)}$Ar, arylsulfonylamine is —NHSO$_{(q)}$Ar, alkylsulfonylamine is NHSO$_2R^a$, aralkylsulfonyl is —SO$_{(q)}R^b$Ar, sulfonamido is —SO$_2NH_2$, nitro is —$NO_2$, carboxy is —$CO_2H$, carbamyl is —$CONH_2$, substituted carbamyl is —C(=O)NH$R^c$ or —C(=O)N$R^c R^d$, alkoxycarbonyl is —C(=O)O$R^a$, carboxyalkyl is —$R^b$—$CO_2H$, sulfonic acid is —$SO_3H$, arylsulfonylamine is —NHSO$_{(q)}$Ar, guanidino is

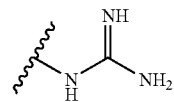

and ureido is

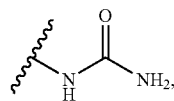

wherein $R^a$ is alkyl as defined above, $R^b$ is alkylene as defined above, $R^c$ and $R^d$ are selected from alkyl, aryl, and aralkyl, Ar is an aryl as defined above, and q is 2 or 3.

Throughout the specification, groups and substituents thereof may be chosen by one skilled in the field to provide stable moieties and compounds.

As used herein, the abbreviations for any protective groups, amino acids and other compounds, are, unless indicated otherwise, in accord with their common usage, recognized abbreviations, or the IUPAC-IUB Commission on Biochemical Nomenclature (see, (1972) *Biochem.* 11:942-944). Ceratin of the abbreviations used herein are listed below:

Ph=phenyl
Bz=benzyl
t-Bu=tertiary butyl
Me=methyl
Et=ethyl
Pr=propyl
Iso-P or iPr=isopropyl
MeOH=methanol
EtOH=ethanol
EtOAc=ethyl acetate
Boc=tert-butyloxycarbonyl
CBZ=carbobenzyloxy or carbobenzoxy or benzyloxycarbonyl
DCM or $CH_2Cl_2$=dichloromethane
DCE=1,2-dichloroethane
DMF=dimethyl formamide
DMSO=dimethyl sulfoxide
TFA=trifluoroacetic acid
THF=tetrahydrofuran
HATU=O-(7-Azabenzotriazol-1-yl)-N,N,N',N'-tetramethyluronim hexafluorophosphate
KOH=potassium hydroxide
$K_2CO_3$=potassium carbonate
$POCL_3$=phosphorous oxychloride
KOtBu=potassium t-butoxide
EDC or EDCI=1-(3-Dimethylaminopropyl)-3-ethylcarbodiimide hydrochloride
DIPEA=diisopropylethylamine
HOBt=1-hydroxybenzotriazole hydrate
m-CPBA=m-chloroperbenzoic acid
NaH=sodium hydride
NaOH=sodium hydroxide
$Na_2SO_4$=sodium sulfate
$Na_2S_2O_3$=sodium thiosulfate
Pd=palladium
Pd/C=palladium on carbon
min=minute(s)
L=liter
mL=milliliter
μL=microliter
g=gram(s)
mg=milligram(s)
mol=moles
mmol=millimole(s)
meq=milliequivalent
RT or rt=room temperature
$t_r$=HPLC retention time (minutes)
sat or sat'd=saturated B. Kinase Inhibitors In one embodiment, compounds for use in compositions and methods for modulating p38 kinase activity are provided. In one embodiment, compounds for use in compositions and methods for modulating kinases p38α and β, are provided.

In certain embodiments, the compounds are represented by formula (I):

or pharmaceutically acceptable derivatives thereof, wherein
$R^1$ is hydrogen, lower alkyl, lower cycloalkyl, alkenyl or alkynyl;
$R^2$ is attached to any available carbon atom of the phenyl ring A and at each occurrence is alkyl or cycloalkyl;
n is 0, 1 or 2;
$R^3$ is selected from hydrogen, alkyl, substituted alkyl, cycloalkyl, heterocyclyl and heteroaryl;
Y is a single bond, —C(=O)NH— or —$SO_2$NH—;
B is a 5-membered heterocyclic ring system optionally substituted with up to two $R^{13}$;
Q is independently selected from a single bond, —C(O)—, —CO(O)—, —C(O)NH—($C_{0-4}$alkyl)- or —$CH_2$—;
D is a monocyclic or bicyclic ring system optionally containing up to four heteroatoms selected from N, O, and S or D is $C_{1-6}$alkyl, and wherein D is optionally substituted by one to four $(CR^9R^{10})_w$E groups;
w is an integer having a value from 0-4;
$R^{10}$ is selected from H or $C_1$-$C_4$ alkylhydroxy, $C_1$-$C_4$alkylaryl or $C_1$-$C_4$alkylheteroaryl, wherein said aryl or heteroaryl group may be substituted with 0-3 groups independently selected from H, halogen, $NO_2$, $C_1$-$C_4$alkyl, $C_3$-$C_{10}$cycloalkyl, $C_2$-$C_6$alkenyl, $C_2$-$C_6$alkynyl, haloalkyl, haloalkoxy, OH, $C_1$-$C_4$alkoxy, $C_1$-$C_4$alkylcarbonyl, CN, $NH_2$, $NR^6R^7$, $SR^6$, $S(O)R^6$, $SO_2R^6$, $SO_3R^6$, $SO_2NR^6$, $CO_2H$, $CO_2R^6$, and $CONR^6R^7$; $R^{11}$ is selected from H, halogen, $NO_2$, $C_1$-$C_4$alkyl, $C_3$-$C_{10}$cycloalkyl, $C_2$-$C_6$alkenyl, $C_2$-$C_6$alkynyl, haloalkyl, haloalkoxy, OH, $C_1$-$C_4$alkoxy-, $OR^6$, $O(CR^9R^{10})_r$, $CO_2R^6$, $O(CR^9R^{10})_mNR^6R^7$, $O(CR^9R^{10})_pCN$, $O(CR_9R_{10})_rC(=O)NR^6R^7$, $C_1$-$C_4$alkylcarbonyl-, CN, $NH_2$, $NHR^6$, $Nr^6R^7$, $NR^7(CR^9R^{10})_rCO_2R^6$, $NR^7OR^6$, $NR^7(CR^9R^{10})_mOR^6$, $NR^7CH((CR^9R^{10})_pOR^6)_2$, $NR^7C(CR^9R^{10})_pOR^6)_3$, $NR^7C(=O)R^6$, $NR^7(CR^9R^{10})_mOR^6$, $NR^7(CR^9R^{10})_mNR^6R^7$, $NR^7(CR^9R^{10})_mSO_2(CR^9R^{10})_qR^6$, $SR^7$, $S(O)R^7$, $SO_2R^7$, $SO_2NR^6$, $SO_3R^7$, $CO_2H$, $CO_2R^6$, and $CONR^6R^7$;
E is selected from H, halogen, $NO_2$, $C_1$-$C_4$alkyl, $C_3$-$C_{10}$, cycloalkyl, $C_2$-$C_6$alkenyl, $C_2$-$C_6$ alkynyl, haloalkyl, haloalkoxy, OH, $OR^6$, CN, CHO, $CO_2R^6$, $CONR^6R^7$, $OCOR_6$, $OC(=O)OR^6$, $OC(=O)NR^6R^7$, $OCH_2CO_2R^6$, $C(=O)R^6$, $NH_2$, $NHR^6$, $NR^6R^7$, $NR^7C(=O)R^6$, $NR^7C(=O)OR^6$, $NR^7C(=O)C(=O)OR^6$, $NR^7C(=O)C(=O)NR^6R^7$, $NR^7C(=O)R^6$, $NR^7C(=O)OR^6$, $NR^7C(=O)C(=O)OR^6$, $NR^7C(=O)C(=O)NR^6R^7$, $NR^7C(=O)C(=O)(C_1$-$C_6$alkyl), $NR^7C(+NCN)OR^6$, $NR^7C(=O)NR^6R^7$, $NR^7C(=NCN)NR^6R^7$, $NR^7C(=NR^6)NR^7R^8$, $NR^6SO_2NR^6R^7$, $NR^7SO_2R^6$, $SR^6$, $S(=O)R^6$, $SO_2R^6$, $SO_3R^7$, $SO_2NR^6R^7$, NHOH, $HHOR^6$, $NR^6NR^7NR^8$, $N(COR^6)OH$, $N(CO_2R^6)$OH, $CO_2R^6$, $CONR^6R^7$, $CONR^7(CR^9R^{10})_rR^6$, $CO(CR^9R^{10})_pO(CHR^9)_qCO_2R^6$, $CO(CR^9CR^{10})_pR^6$, $CO(CR^9R^{10})_pO(CR^9R^{10})_pO(CHR^9)_q$, $CO^2R_6$, $CO(CR^9CR^{10})_r$, $OR^6$, $CO(CR^9R^{10})_pO9CR^9R^{10}_qR^6$, $CO(CR^6CR^{10})_rNR^6R^7$, $OC(O)O(CR9R10R10)_mNR^6R^7$, $O(CO)_M(CR^9R^{10})$, $R^6$, $O(CR^9R^{10})_mNR^6R^7_mNR^7C(O)$ $(CR^9R^{10})_rOR^6$, $NR^7C(\!=\!NC)$ $(CR^9R^{10})_r$, $R^6$, $NR^7CO$ $(CR^9R^{10})_rNR^6R^7$, $NR^7(CR^9R^{10})_mOR^6$, $NR^7(CR^9R^{10})_rCO_2R^6$, $NR^7(CR^9R^{10})_mNR^6R^7$, $NR^7$, $NR^3$ $(CR^9R^{10})_nSO_2(CR^9R^{10})_nCO_2R^6$, $NR^7CR^9R^{10})_mNR^6R^7$, $NR^7(CR^9R^{10})_nSO_2(CR^9R^{10})_qR^6$, $CONR^7(CR^9R^{10})_nSO_2(CR^9R^{10})_qR^6$, $SO_2NR^7(CR^9R^{10})_qR^6$, $SO_2NR^6$ $(CR^9R^{10})_mOR^6$, $C_2$-$C_6$ alkenyl, $C_3$-$C_{10}$-cycloalkyl, $C_3$-$C_{10}$ cycloalkylmethyl, aryl, heterocyclic optionally substituted with one or two alkyl groups, heteroaryl optionally substituted with one or two alkyl groups and alkylaryl, wherein said aryl groups may be substituted with 0-2 substituents independently selected from $R^{12}$;

$R^{12}$ at each occurrence are independently selected from H, halogen, $NO_2$, $C_1$-$C_4$alkyl, $C_3$-$C_{10}$cycloalkyl, $C_2$-$C_6$alkenyl, $C_2$-$C_6$alkynyl, haloalkyl, haloalkoxy, OH, oxo, $C_1$-$C_4$alkoxy-, $OR^6$, $O(CR^9R^{10})$, $CO_2R^6$, $O(CR^9R^{10})_mNR^6R^7$, $O(CR^9R^{10})_pCN$, $O(CR^9R^{10})_pC(\!=\!O)$ $NR^6R^7$, $C_1$-$C_4$alkylcarbonyl-, CN, $NH_2$, $NHR^6$, $NR^6R^7$, $NR^7$ $(CR^9R^{10})$, $CO_2R^6$, $NR^7OR^6$, $NR^7(CR^9R^{10})_mOR^6$, $NR^7CH$ $((CR^9R^{10})_pOR^6)_2$, $NR^7C((CR^9R^1O)_pOR^6)_3$, $NR^7C(\!=\!O)R^6$, $NR^7(CR^9R^{10})_mOR^6$, $NR^7(CR^9R^{10})_mNR^6R^7$, $NR^7$ $(CR^9R^{10})_qR^6$, $SR^7$, $S(O)R^7$, $SO_2R^7$, $SO_2NR^6$, $SO_3R^7$, $CO_2H$, $CO_2R^6$, and $CONR^6R^7$;

m is an integer having a value from 2-6;

p is an integer having a value from 1-3;

q is an integer having a value from 0-3;

r is an integer having a value from 0-6;

$R^4$ is hydrogen, lower alkyl and lower cycloalkyl;

$R^5$ is hydrogen, lower alkyl and lower cycloalkyl;

$R^6$, $R^7$ and $R^8$ are independently selected as follows:

i) $R^6$, $R^7$ and $R^8$ are independently selected from H, $C_1$-$C_6$alkyl, $C_3$-$C_{10}$cycloalkyl, $C_2$-$C_6$alkenyl, $C_2$-$C_6$alkynyl, $C_1$-$C_6$alkylcarbonyl, $C_3$-$C_7$cycloalkyl ($C_0$-$C_5$alkyl)carbonyl, $C_1$-$C_6$alkoxycarbonyl, aryl($C_0$-$C_5$ alkyl)carbonyl, aryl($C_1$-$C_5$alkoxy)carbonyl, heterocyclic($C_0$-$C_5$alkyl)carbonyl, heterocyclic($C_1$-$C_5$alkoxy)carbonyl, $C_1$-$C_6$alkylsulfonyl, arylsulfonyl, heteroarylsulfonyl, $C_0$-$C_4$alkylaryl, $C_0$-$C_4$alkylheterocyclic, wherein said cycloalkyl, aryl, or heterocyclic groups are substituted with 0-2 substituents independently selected from the group consisting of $C_1$-$C_4$alkyl, hydroxyl, $C_1$-$C_4$ alkoxy, F, Cl, Br, haloalkyl, $NO_2$ and CN or, ii) $R^6$ and $R^7$, or $R^6$ and $R^8$, or $R^7$ and $R^8$, when both substituents are on the same nitrogen atom (as in ($-NR^6R^7$) or ($-NR^7R^8$)), can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, 1-piperaziyl, 1-imidazolyl, 3-azabicyclo(3,2,2)nonan-3yl, and 1-tetrazolyl, the said heterocycle being optionally substituted with 0.3 groups selected from oxo, $C_0$-$C_4$alkylOH, $C_0$-$C_4$alkylOC$_1$-$C_4$alkyl, $C_0$-$C_4$alkylCONH$_2$, $C_0$-$C_4$alkylCO$_2$C$_0$-$C_4$alkyl, $C_1$-$C$ alkyl, $C_1$-$C_4$alkoxy, $C_3$-$C_7$cycloalkyl, $C_0$-$C_6$ alkylcarbonyl, $C_3$-$C_7$cycloalkylcarbonyl, $C_1$-$C_6$alkoxycarbonyl, $C_3$-$C_7$cycloalkoxycarbonyl, $-$NHCOalkyl, aryl, heteroaryl, aryl alkoxycarbonyl, heteroaryl alkoxycarbonyl, $C_1$-$C_6$ alkylsulfonyl, arylsulfonyl and heteroarylsulfonyl;

$R^9$ is hydrogen or $C_1$-$C_4$alkyl;

$R^{13}$ is hydrogen, alkyl, haloalkyl, aminocarbonyl, hydroxycarbonyl, alkoxycarbonyl, cycloalkylalkylaminocarbonyl, aryl optionally substituted with one or more $R^{14}$, heteroaryl, heterocyclyl, alkylthio, alkylaminocarbonyl or $OR^{15}$;

$R^{14}$ is hydrogen, halo, hydroxy, cyano, alkyl, haloalkyl, cyanoalkyl, aminoalkyl, alkoxy, hydroxycarbonyl, alkoxycarbonyl, aminocarbonyl, $CONR^aR^b$, where $R^a$ and $R^b$ are each independently selected from hydrogen, alkyl, alkenyl, alkynyl, cycloalkyl, alkoxycarbonylaminoalkyl and alkylamino; or $R^a$ and $R^b$ together with the nitrogen on which they are substituted form a 3-6 membered heterocyclic or heteroaryl ring;

$R^{15}$ is hydrogen, alkyl, hydroxycarbonylalkyl, alkylaminoalkyl, dialkylaminoalkyl, aminoalkyl, heterocyclyalkyl or heteroarylalkyl.

In one embodiment, $R^1$ is methyl, halo, hydroxyl, lower alkyl, lower cycloalkyl, lower alkynyl, trifluoromethyl, methoxy, trifluoromethoxy, cyano, $-NH_2$ or $-NR^4R^5$.

In another embodiment, $R^1$ is methyl, halo, hydroxyl, lower alkyl, lower cycloalkyl, lower alkynyl, trifluoromethyl, methoxy, trifluoromethoxy, cyano, $-NH_2$, $-NR^4R^5$ or $-OR^4$.

In certain embodiments, the compounds have formula (I) with the proviso that ring B is not substituted with $NH_2$.

In one embodiment, $R^1$ is hydrogen or lower alkyl.

In another embodiment, $R^1$ is hydrogen or methyl.

In another embodiment, $R^1$ is methyl.

In one embodiment, $R^2$ is hydrogen or alkyl.

In one embodiment, $R^2$ is hydrogen or lower alkyl.

In one embodiment, $R^2$ is hydrogen.

In another embodiment, $R^3$ is selected from alkyl, $-OR^4$, substituted alkyl, cycloalkyl, $-CR^4$cycloalkyl, heteroaryl, substituted heteroaryl, heterocycle and substituted heterocycle.

In one embodiment, $R^3$ is cycloalkyl, cycloalkylalkyl, alkoxyalkyl or heteroaryl.

In one embodiment, $R^3$ is methyl, isopropyl, ethyl, cyclopropyl, cyclopropylmethyl, methoxymethyl, oxazolyl or thiazolyl.

In another embodiment, Y is $-C(\!=\!O)NH-$, $-NH$ $(C\!=\!O)-$, $-NH(C\!=\!O)NH-$, $-SO_2NH-$, $-NHSO_2-$ or $-C(\!=\!O)-$.

In another embodiment, Y is a single bond, $-C(\!=\!O)$ NH— or $-SO_2NH$.

In another embodiment, B is a thiazolyl, oxazolyl, dithiazolyl, thiadiazolyl, oxadiazolyl or triazinyl ring optionally substituted with one or two $R^{13}$.

In another embodiment, B is a thiazolyl ring optionally substituted with one or two $R^{13}$.

In another embodiment, B is a thiazolyl ring optionally substituted with one $R^{13}$.

In another embodiment, Q is a single bond, $-CO(O)-$, $-C(O)-$ or $-C(O)NH-(C_{0-4}alkyl)-$.

In another embodiment, Q is a single bond.

In another embodiment, Q is $-C(O)-$.

In another embodiment, Q is $-CO(O)-$.

In another embodiment, Q is $-C(O)NH-(C_{0-4}alkyl)-$.

In another embodiment, Q is $-C(O)NH-$ or $-C(O)$ $NHCH_2CH_2-$.

In another embodiment, Q is $-C(O)NH-$.

In another embodiment, D is a monocyclic or bicyclic ring system optionally containing up to four heteroatoms selected from N. O, and S or D is $C_{1-6}$alkyl and wherein D is optionally substituted by one to four $(CR^9R^{10})_wE$ groups.

In another embodiment, D is $C_{1-6}$alkyl, alkoxy, cycloalkyl, aryl, arylalkyl, heterocyclyl or heteroaryl ring, wherein the heteroatoms are selected from O, N and S and D is optionally substituted with one or four $(CR^9R^{10})_wE$ groups.

In another embodiment, D is selected from methyl, ethyl, propyl, ethoxy cyclopropyl, phenyl, benzyl, benzimidazolyl, piperazinyl, piperidinyl, diazaoxazolyl or pyrimidinyl and D is optionally substituted with one or four $(CR^9R^{10})_w$E groups.

In another embodiment, D is selected from 1-piperazinyl, 4-piperidinyl, 4-pyridinyl, 1,3,4-diazaoxazolyl or 3-pyridinyl, and D is optionally substituted with one or two $(CR^9R^{10})_w$E groups.

In another embodiment, D is phenyl and D is optionally substituted with one or two $(CR^9R^{10})_w$E groups.

In another embodiment, w is 1.

In another embodiment, w is 0.

In another embodiment, D is substituted with one to four substituents selected from halo, alkyl, nitro, alkoxy, alkoxycarbonylalkoxy, alkoxyamidoalkylamido, hydroxycarbonyl, alkoxycarbonyl, alkylaminocarbonyl, alkylcarbonylamino, aryl, heteroaryl containing 1 to 3 heteroatoms and optionally substituted with one or two alkyl groups, and heterocyclyl containing 1 to 3 heteroatoms and optionally substituted with two or more alkyl or alkoxycarbonyl groups.

In another embodiment, D is substituted with one to four substituents selected from chloro, fluoro, methyl, methoxy, ethoxy, methylaminocarbonyl, methoxycarbonylamino, tert-butyloxyamidoethylamido, methoxycarbonyl or phenyl.

In another embodiment, D is substituted with heterocyclyl ring selected from morpholinyl or piperidinyl, where the heterocyclyl ring is further substituted with one or two methyl or methoxycarbonyl groups.

In another embodiment, D is substituted with heteroaryl ring selected from isoxazolyl, furyl, benzimidazolyl and thiazolyl, where the heteroaryl ring is further substituted with one or two methyl groups.

In another embodiment, D is substituted with N-morpholinyl, piperidin-4-yl or 1-methoxycarbonylpiperidin-4-yl.

In another embodiment, D is substituted with 2-benzimidazolyl, 3,5-dimethylisoxazol-4-yl, 5-methylisoxazol-3-yl or 2-methylthiazol-5-yl.

In another embodiment, D is selected from methyl, ethyl, propyl, isopropyl, hydroxycarbonylmethyl, methylaminocarbonylmethyl, ethoxycarbonylpropyl, ethoxycarbonylmethyl, phenyl, fluorophenyl, tolyl, methoxyphenyl, methoxycarbonylmethoxy, ethoxy, benzimidazolyl, methylpiperazinyl, piperidinyl, 1,3,4-diazaoxazolyl, morpholin-1-ylphenyl, piperidin-4-ylphenyl, 1-methoxycarbonylpiperidin-4-ylphenyl, benzyl, chlorophenyl, methylcarbonylaminophenyl, bromophenyl, carboxymethyl, tertbutyloxyamidoethylamidophenyl, methylaminocarbonylmethyl, N-methoxycarbonylpiperidinyl, piperidinyl, pyridinyl, cyclopropyl, dimethylisoxazolylmethyl, methylisoxazolylmethyl and methylthiazolylmethyl.

In another embodiment, D is selected from methyl, ethyl, propyl, isopropyl, cyclopropylmethyl, hydroxycarbonylmethyl, ethoxycarbonylpropyl, methylaminocarbonylmethyl, ethoxycarbonylmethyl, phenyl, 4-fluorophenyl, p-tolyl, 4-methoxyphenyl, 4-methoxycarbonylmethoxyphenyl, ethoxy, 2-benzimidazolylmethyl, 4-methylpiperazin-1-yl, 1,3,4-diazaoxazolyl, 4-piperidinyl, benzyl, 4-chlorophenyl, 4-morpholin-1-ylphenyl, 4-(piperidin-4-yl)phenyl, 4-(1-methoxycarbonylpiperidin-4-yl)phenyl, 4-ethoxycarbonylmethoxyphenyl, 4-methylamidophenyl, and 4-tertbutyloxyamidoethylamidophenyl.

In another embodiment, $R^{13}$ is selected from methyl, trifluoromethyl, tert-butyl, amido, methoxycarbonyl, carboxyl, ethoxycarbonyl, cyclopropylmethylaminocarbonyl, thienyl, methylenedioxybenzyl, ethylenedioxybenzyl, pyridinyl, and phenyl; and $R^{13}$ is optionally substituted with one or more $R^{14}$, where $R^{14}$ is hydrogen, chloro, fluoro, hydroxy, methyl, cyano, amino, aminoethyl, N-morpholinyl, methylsulfonylamino, tertbutoxyamidomethylamido, tertbutoxyamidoethylamidophenyl, aminomethylamido, methoxycarbonylpiperazinyl, methylcarbonyl, methoxy, ethoxy, methoxycarbonyl, trifluoromethyl, hydroxymethyl, amido, aminomethyl, carboxy, tertbutoxyamidoethylamido, aminoethylamido, methylsulfonyl, N-morpholinocarbonyl, cyclopropylamido, ethylthio, carboxymethoxy, N-morpholinoethoxy, aminoethoxy, ethylamido, n-butoxy, aminopropyloxy or carboxymethoxy.

In another embodiment, $R^{13}$ is selected from methyl, trifluoromethyl, tert-butyl, amido, methoxycarbonyl, carboxyl, ethoxycarbonyl, cyclopropylmethylaminocarbonyl, thienyl, methylenedioxybenzyl, ethylenedioxybenzyl, 4-cyanomethylphenyl, 4-cyanophenyl, 2-chlorophenyl, 4-hydroxyphenyl, m-tolyl, 3-fluorophenyl, p-tolyl, 3-cyanophenyl, 5-methylcarbonylthien-2-yl, 5-cyanothien-2-yl, 4-methoxyphenyl, 4-methoxycarbonylphenyl, 4-fluorophenyl, 2-methoxyphenyl, 2-trifluoromethylphenyl, 4-hydroxymethylphenyl, 3-aminocarbonylphenyl, 4-aminocarbonylphenyl, 3-aminomethylphenyl, 3-carboxyphenyl, 4-carboxyphenyl, o-tolyl, 2,4-difluorophenyl, 3-aminoethylaminocarbonylphenyl, 4-aminoethylaminocarbonylphenyl, 3-aminomethylaminocarbonylphenyl, 4-aminomethylaminocarbonylphenyl, 4-methylsulfonylphenyl, 4-(N-morpholino)carbonylphenyl, 4-ethoxy-3-fluorophenyl, 3-cyclopropylamidophenyl, 3-ethoxyphenyl, 4-ethylthiophenyl, 4-methoxy-3-fluorophenyl, 4-fluoro-3-methylphenyl, 3,4-difluorophenyl, 3-methyl-4-methoxyphenyl, 3-hydroxycarbonylmethoxyphenyl, 4-(N-morpholino)ethoxyphenyl, 4-hydroxyphenyl, phenyl, 3-aminoethoxyphenyl, 4-ethylaminocarbonylphenyl, 4-n-butoxyphenyl, 3-methyl-4-methoxyphenyl, 3-aminopropyloxyphenyl 4-cyanomethylphenyl, 4-aminophenyl, 3-aminophenyl, 4-aminoethylphenyl, 4-morpholin-1-ylphenyl, 4-methylsulfonylaminophenyl, 3-tertbutoxyamidomethylamidophenyl, 4-tertbutoxyamidomethylamidophenyl, 3-tertbutoxyamidoethylamidophenyl, 4-tertbutoxyamidoethylamidophenyl, 3-aminomethylamidophenyl, 4-(methoxycarbonylpiperazin-1-yl)phenyl and 2-methoxypyrimidin-3-yl.

In certain embodiments, the compounds provided herein are represented by formula (I-1):

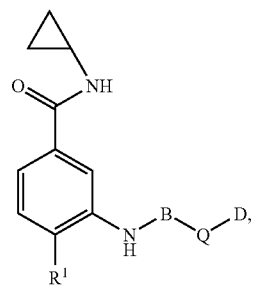

where B is selected from 1,2,4-triazole, 1,2,4-oxadiazole, 1,3,4-thiadiazole, 1,2,4-thiadiazole, oxazole and thiazole.

In certain embodiments, the compounds provided herein are represented by formula (I-2):

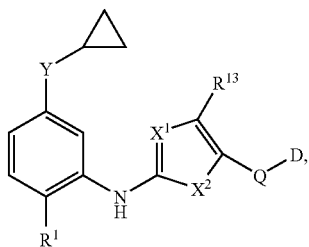

where $X^1$ is selected from O, S and optionally substituted N, where the substituent on the N when present is selected from hydrogen, alkyl, substitued alkyl, alkenyl or alkynyl and $X^2$ is S or O.

In certain embodiments, the compounds provided herein are represented by formula (I-3):

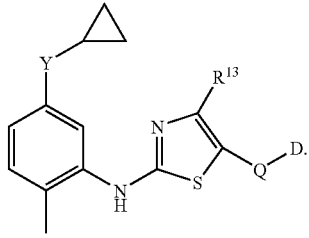

In certain embodiments, the compounds have formula (I-4):

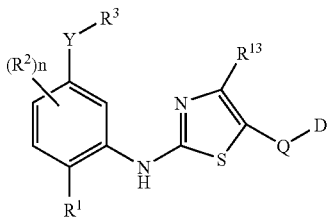

In certain embodiments, the compounds provided herein are represented by formula (I-5):

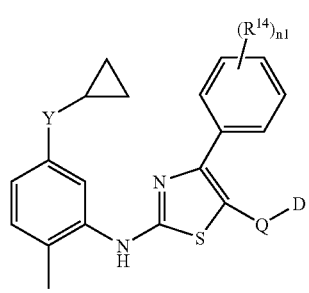

where $n_1$ is 0-5.

In certain embodiments, the compounds provided herein are represented by formula (I-6):

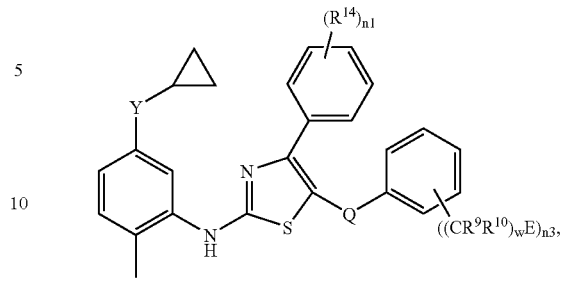

where $n_3$ is 1-4.

In certain embodiments, the compounds provided herein are represented by formula (I-7):

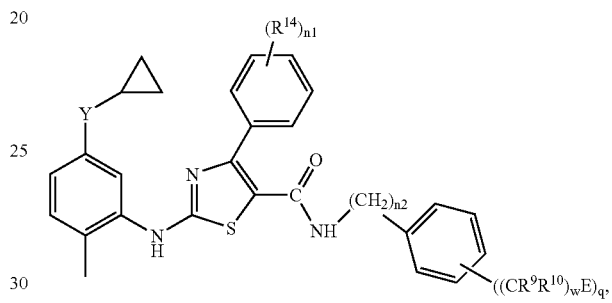

where $n_2$ is 0-4.

In certain embodiments, the compounds provided herein are represented by formula (I-8):

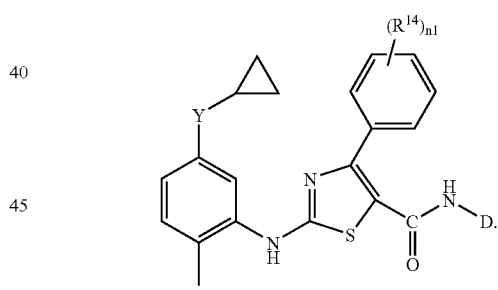

In certain embodiments, the compounds provided herein are represented by formula (I-9):

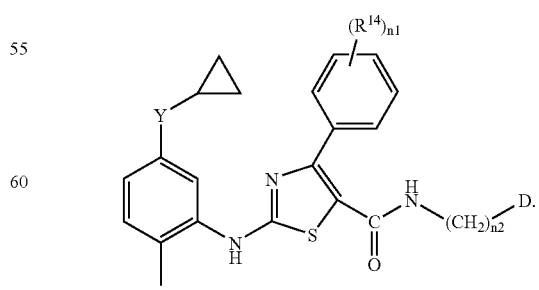

In certain embodiments, the compounds provided herein are selected from formula (I-10) as follows:

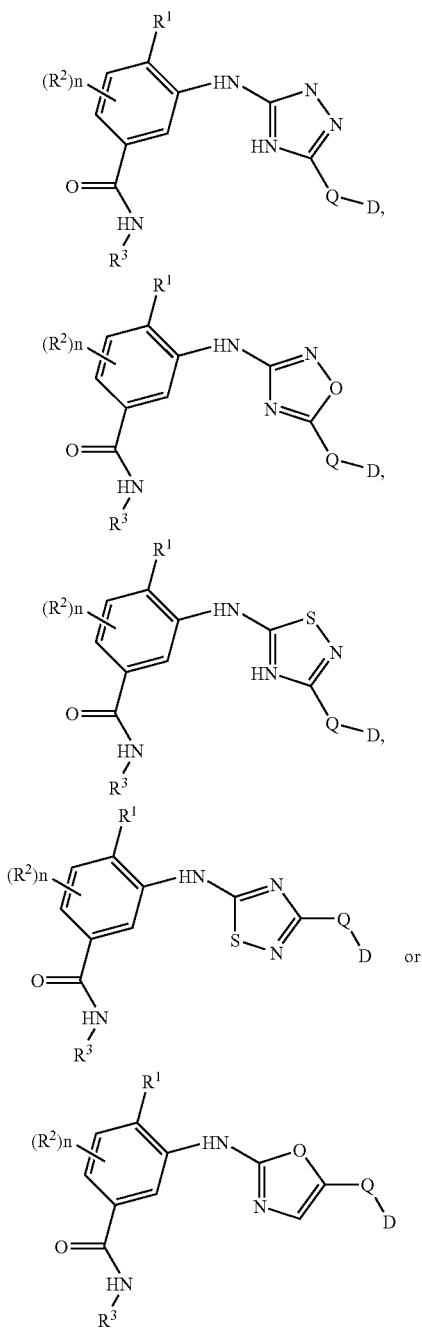

In one embodiment, the compounds are salts of the compounds of Formula (I). In certain embodiments, the salts are pharmaceutically acceptable (i.e. non-toxic, physiologically acceptable) salts, in other embodiments, the compounds are other salts which are useful, for example, in isolating or purifying the compounds provided herein.

In another embodiment, the compounds are selected from the compounds listed Table 1.

The compounds of Formula (I) may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for Formula (I) may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

Salt forms of the compounds may be advantageous for improving the compound dissolution rate and oral bioavailability.

In addition, zwitterions ("inner salts") may be formed.

All stereoisomers of the compounds are contemplated to be within the scope of the disclosure, either in admixture or in pure or substantially pure form. All the possible stereoisomers and their mixtures are contemplated to be within the scope of the disclosure. It embraces the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the Formula (I) may also have prodrug forms. Any compound that will be converted in vivo to provide the bioactive agent (i.e., the compound for formula I) is a prodrug and is within the scope the disclosure.

Various forms of prodrugs are well known in the art. For examples of such prodrug derivatives, see:

a) *Design of Prodrugs*, edited by H. Bundgaard, (Elsevier, 1985) and *Methods in Enzymology*, Vol.42, p. 309-396, edited by K. Widder, et al. (Acamedic Press, 1985);

b) *A Textbook of Drug Design and Development*, edited by Krosgaard-Larsen and H. Bundgaard, Chapter 5, "Design and Application of Prodrugs," by H. Bundgaard, p. 113-191 (1991); and c) H. Bundgaard, *Advanced Drug Delivery Reviews*, 8, 1-38 (1992), each of which is incorporated herein by reference.

It should further be understood that solvates (e.g., hydrates) of the compounds of Formula (I) are also contemplated herein. Methods of solvation are generally known in the art.

The ability of the compounds provided herein, to inhibit the synthesis or the activity of cytokines can be demonstrated using the in vitro assays described in section E.

C. Preparation of the Compounds

Compounds of formula I may be generally be prepared according to the following schemes and the knowledge of one skilled in the art. In addition to the documents incorporated by reference we disclose the following. Examples of methods useful for the production of compounds provided herein are illustrated in schemes 1-18.

Appropriately substituted 1,2,4-aminotriazoles of type (II), which are useful herein, can be made by several means, for example as shown in scheme 1, reaction of an appropriately substituted amine with a reagent such as 1,1'thiocarbonyldi-2(1H)-pyridone, 1,1'-thiocarbonyldiimidazole or thiophosgene in a solvent such as methylene chloride or dioxane yields the isothiocyanate. Treatment of the isothiocyanate with sodium salt of cyanamide yields the sodium salt of N-cyanothiourea which is cyclized to the aminotriazole (II) using a appropriately substituted hydrazine and a dehydrating agent such as 1-ethyl-3-(3-dimethylaminopropyl)carbodiimide hydrochloride (EDC), or DCC. (*Bioorg. Med. Chem. Letters* 12: 3125-3128 (2002))

Scheme 1

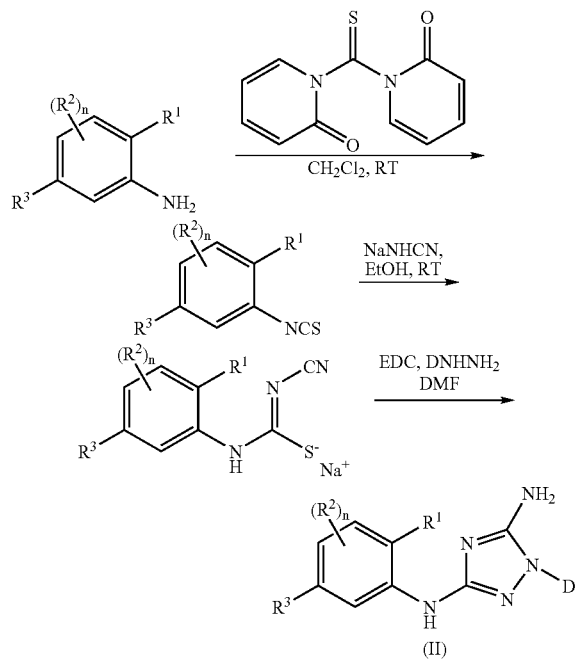

1,2,4-Aminotriazoles of type (II), which are useful herein, may also be prepared as outlined in Scheme 2. An appropriately substituted amine can react with diphenyl cyanocarbonimidate to yield the N-cyano-O-phenylisourea. Cyclization of N-cyano-O-phenylisourea to the appropriately substituted triazole (II) is achieved using an appropriately substituted hydrazine and a solvent such as acetonitrile.

Scheme 2

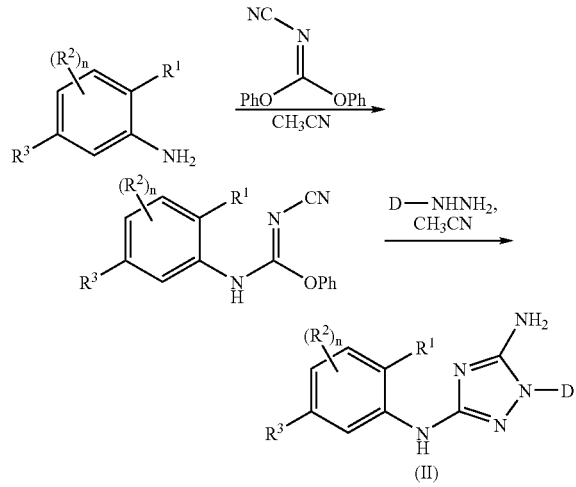

Appropriately substituted 1,2,4-triazoles of type (111), which are useful herein, can be prepared as by several methods for example as outlined in Scheme 3. Acylisothiocyanates are useful intermediates in the production of some compounds provided herein and are either commercially available or readily prepared by reaction of an acid chloride, with either sodium or potassium isothiocyanate in an inert solvent such as dioxane. Acid chlorides are either commercially available or readily prepared by reaction of a carboyxylic acid and a reagent such as thionyl chloride, or oxalyl chloride in the presence of a catalytic amount of N,N-dimethylformamide, in an inert solvent such as chloroform or methylene chloride. Reaction of an appropriately substituted amine with an acylisothiocyanate yields the thiourea. The thiourea is cyclized to (III) using hydrazine in a solvent such as ethyl alcohol or a solvent mixture such as THF and ethyl alcohol, at a temperature preferably between 60° C. and the boiling point of the solvents utilized. (*Bioorg. Med. Chem. Letters* 12: 3125-3128 (2002))

Scheme 3

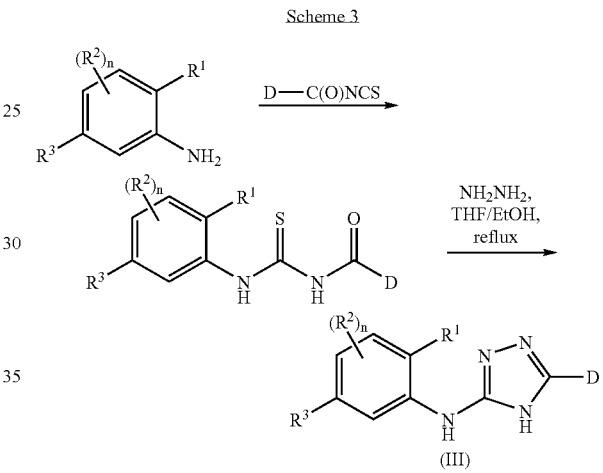

Appropriately substituted 2-amino-1,3,4-oxadiazoles of type (IV), which are useful herein, can be prepared by several methods one of which is outlined in Scheme 4. Reaction of an appropriately substituted amine with an activating agent such as 1,1'carbonyldiimidazole followed by treatment with a appropriately substituted hydrazine yields the carbonylhydrazide. The carbonylhydrazide on treatment with 1,2-dibromotetrachloroethane and triphenylphosphine in the presence of a suitable base such as triethylamine and an appropriate solvent such as acetonitrile yields compound (IV). (*Bioorg. Med. Chem. Letters* 12: 3125-3128 (2002))

Scheme 4

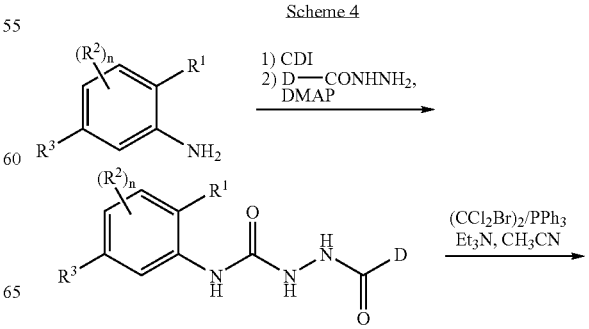

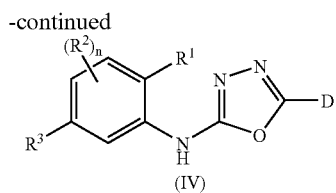

(IV)

Appropriately substituted 3-amino-1,2,4-oxadiazoles of type (V), useful herein, can be prepared by several methods one of which is outlined in Scheme 5. Reaction of an appropriately substituted amine with an appropriately substituted acylisothiocyanate yields the thiourea. Reaction of the thiourea with a base such as sodium hydroxide or sodium hydride followed by a alkylating agent such as methyl iodide gives the S-methylisothiocarbamoyl intermediate which on treatment with hydroxylamine in the presence of a suitable solvent such as ethyl alcohol or butyl alcohol at a temperature preferably between 60 and 110° C. results in cyclization to the desired 3-amino-1,2,4-oxadiazole. (*Bioorg. Med. Chem. Letters* 12: 3125-3128 (2002))

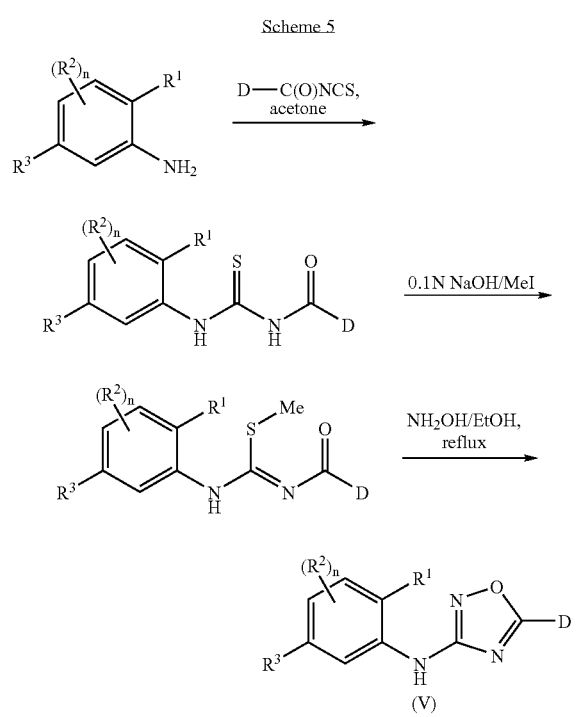

Appropriately substituted 2-amino-1,3,4-thiadiazoles of type (VI), which are useful herein, can be prepared by several methods one of which is illustrated in Scheme 6. Reaction of an appropriately substituted isothiocyanate with an appropriately substituted hydrazide yields the thiourea, which is cyclized to the desired heterocycle using a dehydrating agent such as methansulphonic acid, in an inert solvent such as toluene or xylene, at a temperature preferably between 80° C. to 140° C. (*Bioorg. Med. Chem. Letters* 12: 3125-3128 (2002))

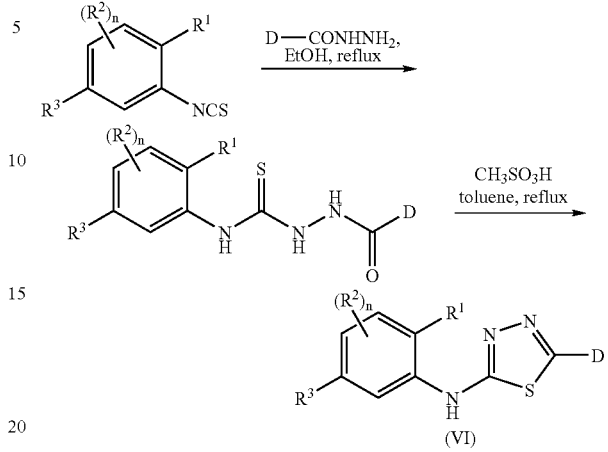

(VI)

Appropriately substituted 3-amino-1,2,4-thiadiazoles of type (VII), useful herein, can be made by several method known to one skilled in the art of organic chemistry. One method is outlined in scheme 7. Reaction of an appropriately substituted isothiocyanate and an amidoxime in a solvent such as chloroform, or toluene at a 10 temperature preferably between 60° C. and 110° C. results in the production of the desired heterocycle. Amidoximes useful herein are either commercially available, or readily prepared by many methods known to one skilled in the art of organic chemistry such as reaction of a nitrile with anhydrous hydrochloric acid in anhydrous methanol followed by reaction of resulting imidate with hydroxylamine.

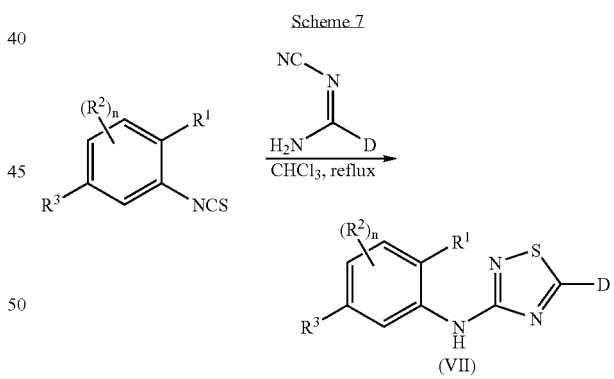

(VII)

Appropriately substituted 5-amino-1,2,4-thiadiazoles of type (VII*), useful herein, can be made by several method known to one skilled in the art of organic chemistry. One method is outlined in scheme 7*. Reaction of an appropriately substituted isothiocyanate and an N-hydroxy-amidine in a solvent such as DMF under microwave raditation at a temperature of 200° C. results in the production of the desired heterocycle. N-Hydroxy-amidines useful herein are either commercially available, or readily prepared by many methods known to one skilled in the art of organic chemistry such as reaction of a nitrile with hydroxylamine hydrochloride and an appropriate base such as potassium carbonate in ethanol.

Scheme 7*

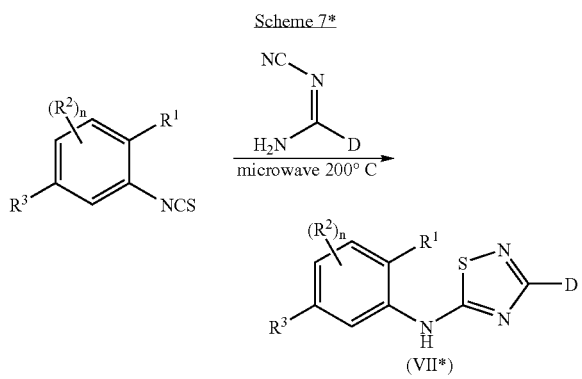

3-Aminoisoxazoles of type (VIII) that are useful herein can be prepared by several methods including the method outlined in scheme 8. Reaction of an appropriately substituted isocyanate with a ketone in the presence of a base such as sodium hydride and an alkylating agent such as methyl iodide gives a thiomethyl intermediate which on treatment with hydroxylamine in a solvent such as ethyl or butyl alcohol at a temperature preferably between 60-120° C. yields the appropriately substituted 3-aminoisoxazoles. Ketones useful herein are either commercially avialble or readily prepared by several methods such as Friedel-Crafts acylation as described in chapter 11 of "Advanced Organic Chemistry" 3'd edition, Part B, Carey, F. A. and Sundberg, R. J., Plenum Press New York, 1990, hydrolysis of an enol ether, or oxidation of an alcohol, as outlined in "Comprehensive Organic Transformations, A Guide to Functional Group Preparations" Larock, R. C., VCH Publishers, New York, 1989. (*Bioorg. Med. Chem. Letters* 12: 3125-3128 (2002))

Scheme 8

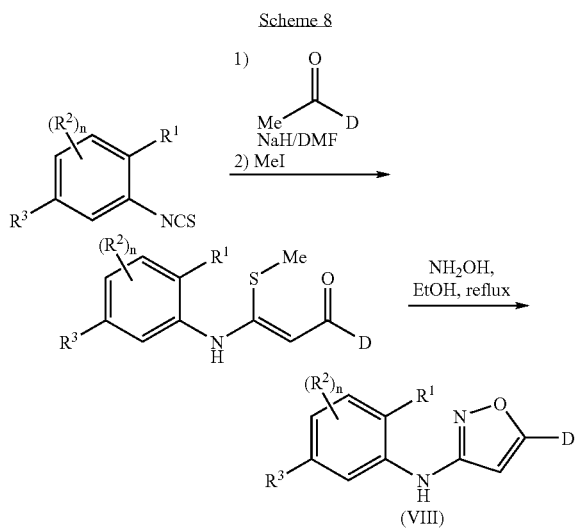

5-Aminothiazoles of type (IX) that are useful herein can be prepared by several methods including the method outlined in scheme 9. Reaction of an amine with an amino acid in the presence of an activating agent such as 1,1'carbonyldiimidazole in a suitable solvent such as tetrahydrofuran yields an amide. Amides may be readily prepared by a number of methods including reaction of an amine with an acid chloride, or coupling of a carboxylic acid and the amine in the presence of a variety of coupling agents such as EDC, DCI, in the presence of an amine base. The coupling reaction may be enhanced by the addition of 1hydroxybenzotriazole or similar additives. Reaction of the amide with Lawesson's reagent in the presence of a base such as pyridine at a temperature preferably between 80-120° C. yields the appropriately substituted 5-aminothiazoles. (*Bioorg. Med. Chem. Letters* 12: 3125-3128 (2002))

Scheme 9

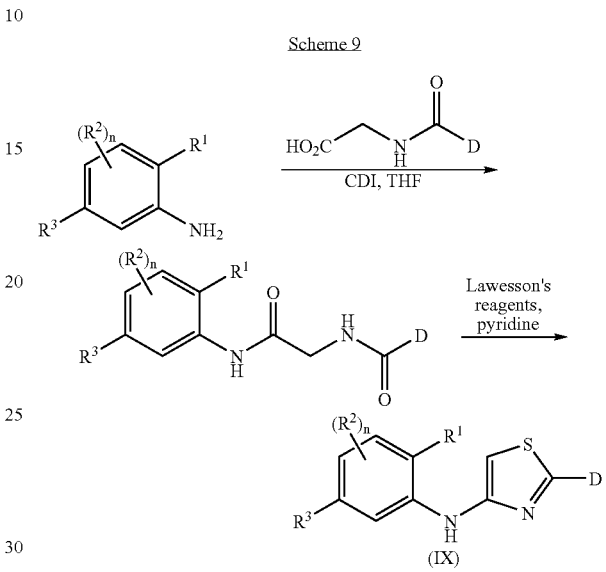

2-Aminothiazoles of type (X) useful herein can be prepared by several methods 20 including the method outlined in scheme 10. Reaction of an isothiocyanate with ammonia in a solvent such as dioxane yields the thiourea. Aryl bromides useful herein are either commercially available or readily prepared by reaction of a carboxylic acid with thionylbromide. Treatment of the thiourea with an acylbromide, in the presence of a solvent such as ethyl alcohol or dioxane, at a temperature preferably between 60° C. and 110° C., yields the appropriately substituted 2-amino-1,3-thiazoles. (*Bioorg. Med. Chem. Letters* 12: 3125-3128 (2002))

Scheme 10

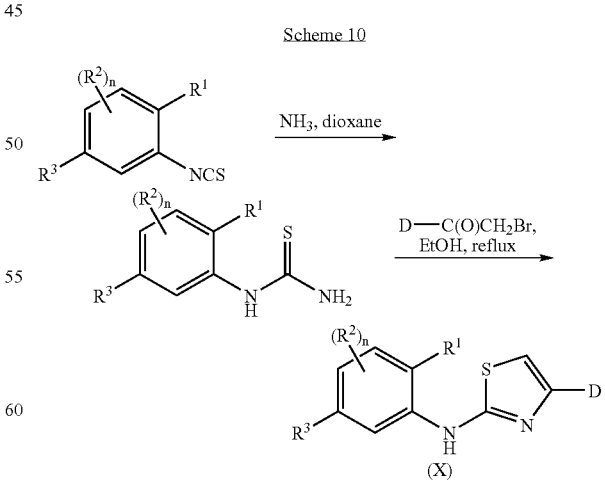

2-Aminothiazoles of type (X*) useful herein can be prepared by several methods 20 including the method outlined in scheme 10*. Treatment of the thiourea with an acylbromide, additionally substituted with an electron withdrawing group such as cyano, ester, or amide, in the presence of a solvent such as ethyl alcohol or dioxane, at a temperature preferably between 60° C. and 110° C., yields the appropriately substituted 2-amino-1,3-thiazoles.

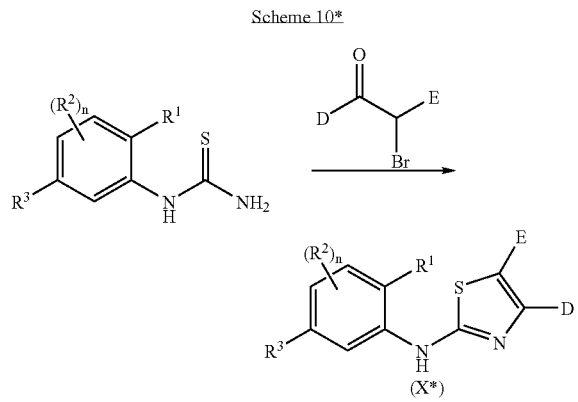

Alternatively, 2-aminothiazoles of type (X**) useful herein can be prepared by the method outlined in scheme 10* Reaction of 2,4-dibromothiazole, obtained by treatment of 2,4-thiazolidinedione with phosphorus oxybromide at a temperature preferably between 60° C. and 110° C., with lithium diisopropylamide and an isocyanate at low temperature provides the 2,4-dibromothiazole-5-carboxamide. Treatment of this intermediate by an aniline in the presence of a solvent such as dimethylsulfoxide at a temperature preferably between 60° C. and 110° C. yields the 4-bromo-2-anilino derivative, which can be treated with and an appropriately substituted boronic acid, catalytic palladium(0), and a base in the presence of a solvent such as ethyl alcohol or dioxane, at a temperature preferably between 60° C. and 110° C., to provide the appropriately substituted 2-amino-1,3-thiazoles.

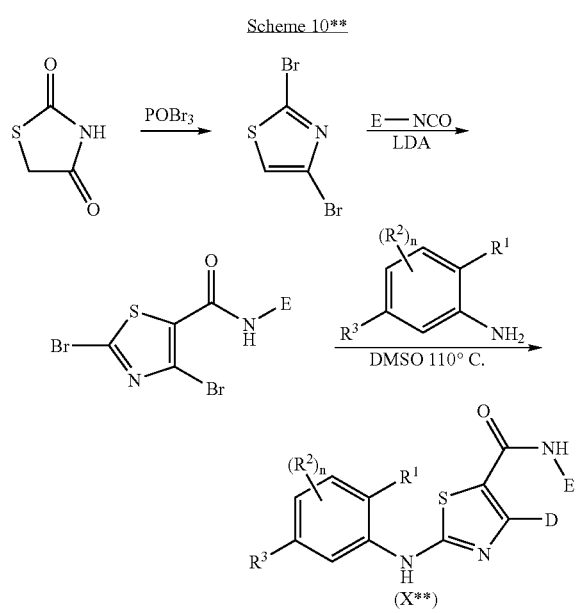

2-Aminothiazoles of type (X*) useful herein can be prepared by several methods including the method outlined in scheme 10*. Reaction of an appropriately substituted methyl vinyl ether such methyl trans 3-methoxyacrylate with NBS in a solvent followed by treatment with the thiourea yields the aminothiazole. (*Tetrahedron Lett.*, 42: 2101-2102 (2001))

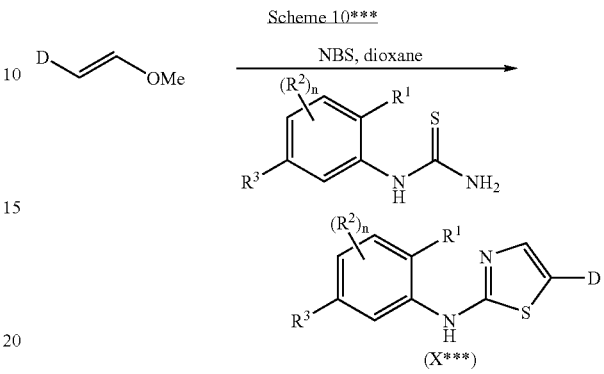

Substituted acyl bromides useful herein may be prepared by several methods, examples of which are outlined in scheme 10B. Appropriately substituted ketones additionally substituted at the beta carbon with an electron withdrawing group such as cyano, ester, or amide can be treated with bromine in an appropriate solvent such as chloroform or methylene chloride to provide acyl bromides.

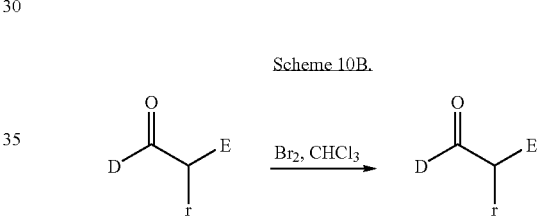

Substituted β-ketoamides useful herein may be prepared by several methods, examples of which are outlined in scheme 10Ca-c. The lithium salt of an appropriately substituted methyl ketone, generated by treatment with a base such as lithium diisopropyl amine, in an appropriate solvent such as THF can be reacted with an iscyanate to provide the desired β-ketoamide.

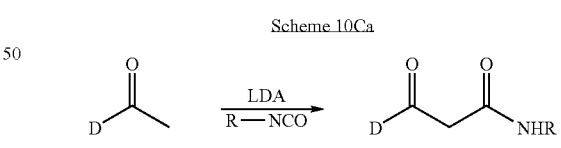

Alternatively, β-ketoesters can be heated with an amine and a catalytic amount of a mild acid such as p-toluenesulfonic acid in an appropriate solvent such as dioxane bromine to provide the β-ketoamide. Microwave heating may accelerate the reaction.

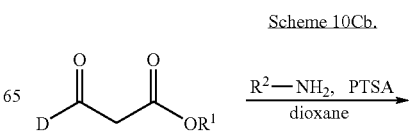

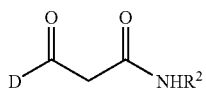

The requistite β-ketoesters useful herein can be purchased or may be prepared by several methods, examples of which are outlined in scheme 10D. Appropriately substituted esterse can be treated with the lithium salt of ethyl or methyl acetated to provide β-ketoesters.

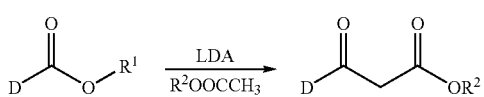

2-Amino-1,3-oxazolines of type (XI) useful herein may be prepared by several methods, an example of which is outlined in scheme 11. An appropriately substituted isothiocyanate is reacted with an aminoalcohol in a suitable solvent such as dioxane to yield the thiourea. Treatment of the thiourea with 2-chloro-3-ethylbenzoxazolium tetrafluoroborate in the presence of a base such as triethylamine in a solvent such as acetonitrile yields the appropriately substituted 2-amino-1,3-oxazolines.

Aminoalcohols useful herein are either commercially available or readily prepared by several methods. One convenient method is reduction of azidoketones of the type described in schemes 14a-14d, either by catalytic hydrogenation in the presence of palladium on carbon in a solvent such as ethanol or ethyl acetate, or by a hydride reagent such as lithium aluminum hydride in a solvent such as dioxane or tetrahydrofuran. (*Bioorg. Med. Chem. Letters* 12: 3125-3128 (2002))

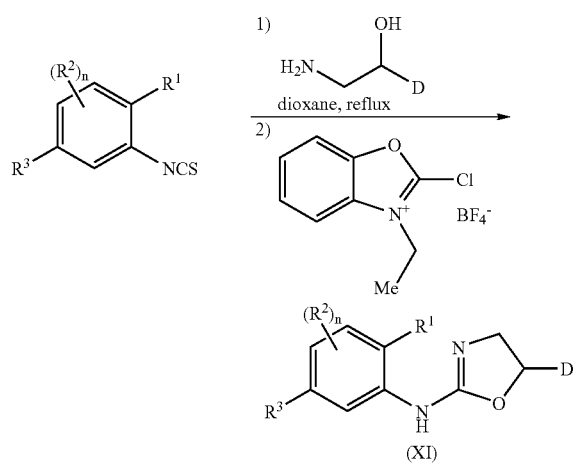

2-Aminooxazoles of type (XII), which are useful herein, can be prepared by several methods, including the method outlined in Scheme 12. Reaction of an isothiocyanate with a 3-ketoamine in the presence of a base such as triethylamine and a solvent such as dioxane yields the thiourea. Reaction of the thiourea in the presence of a dehydrating agent such as dicyclohexylcarbodiimide or EDC, in a solvent such as diox- ane or toluene, at a temperature preferably between 60° C. and 110° C., yields the appropriately substituted 2-aminooxazoles. β-Ketoamines useful herein are either commercially available or readily prepared by several methods. One method is reduction of azidoketones of the type described in schemes 14a-14d by phosphine reagents such as triphenylphosphine in a solvent such as dioxane, followed by the addition of water or dilute ammonium hydroxide. (*Bioorg. Med. Chem. Letters* 12: 3125-3128 (2002))

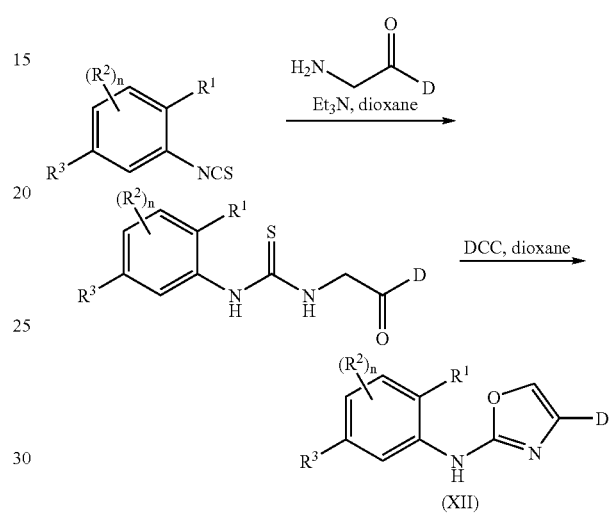

A second method of preparing 2-aminooxazoles of type (XII) is outlined in scheme 13. Reaction of an appropriately substitited isothiocyanate with an acylazide of the type described in schemes 14a-14d in the presence of a phosphine such as triphenylphosphine in a solvent such as dichloromethane or dioxane at a temperature from room temperature to 100° C.

Caution: Appropriate safety methods, which are known to those experienced in conducting azide reactions, such as use of a blast shield, blast wall, or similar containment device, particularly when the reaction involves heating the organic azide, as well as the use of appropriate personal protection to avoid exposure to azides which may be toxic, must be exercised during the preparation and use of organic azides.

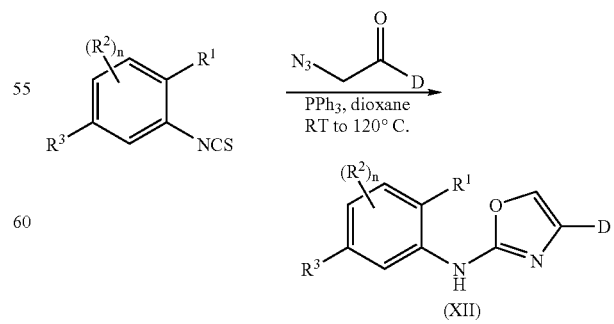

Azides useful herein may be prepared using one of the sequences outlined in schemes 14a-14d.

Scheme 14a outlines the treatment of the α-bromoketone with sodium azide in a solvent such as acetone, generally at room temperature, to yield the desired α-azidoketones useful as intermediates herein. α-Bromoketones are either commercially available or readily prepared by reaction of a ketone with a 10 brominating agent such as bromine in acetic acid or pyridinium bromide per bromide and 30% hydrobromic acid.

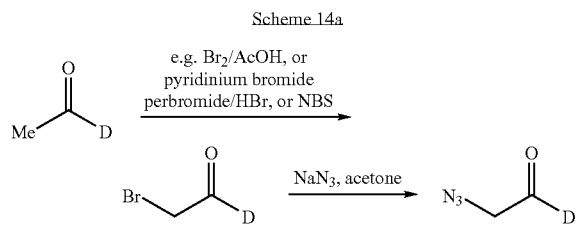

Scheme 14b outlines the treatment of the α-bromoketone with sodium azide in acetone to give the α-azidoketone. In this case, the α-bromoketone is prepared by reaction of a carboxylic acid with isobutylchloroformate and N-methylmorpholine to provide the mixed anhydride, which on treatment with diazomethane gives the α-diazoketone. Reaction of the α-diazoketone with either HBr gas in a solvent such as ether or dioxane, or aqueous 48% HBr, provides the α-bromoketone.

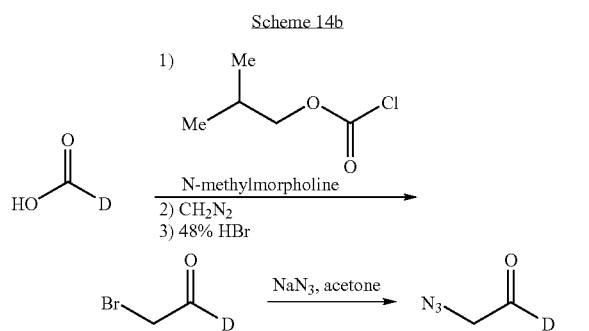

Scheme 14c illustrated preparation of α-bromoketone by reaction of a ketone with sulfuric acid and bromine to yield the α,α-dibromoketone, which on treatment with diethylphosphite and triethylamine yields the α-(mono)bromoketone. Treatment of the α-bromoketone with sodium azide in acetone gives the α-azidoketone.

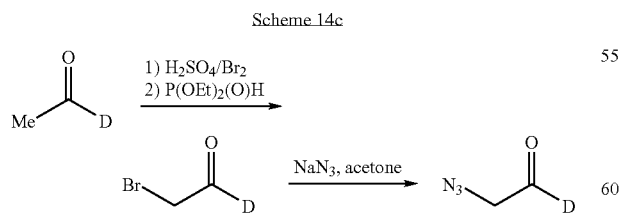

Scheme 14d illustrated preparation of a-bromoketone by reaction of an aryl bromide with tributyl-(1-ethoxyvinyl)tin and bis(triphenylphosphine)palladium dichloride to provide an intermediate enol ether. Treatment of the enol ether with N-bromosuccinamide at a temperature from 0° C. to room temperature yields the α-bromoketone. As previously described treatment of the a-bromoketone with sodium azide in acetone gives the α-azidoketone.

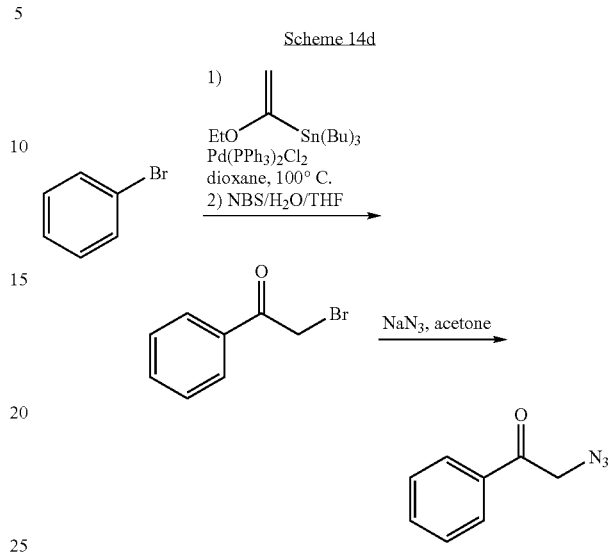

Imidazoles useful herein may be prepared according to the method outlined in scheme 15. Reaction of a guanidine with an α-bromoketone yields 2-aminoimidazoles of type (XIV) in the presence of a base, such as potassium carbonate, in a solvent, such as N,N-dimethylformamide, provides the desired aminoimidazoles. It is recognized that more than one isomeric imidazole can form during this reaction and the desired product can be obtained by a suitable chromatographic method or by recrystalization. (*Bioorg. Med. Chem. Letters* 12: 3125-3128 (2002))

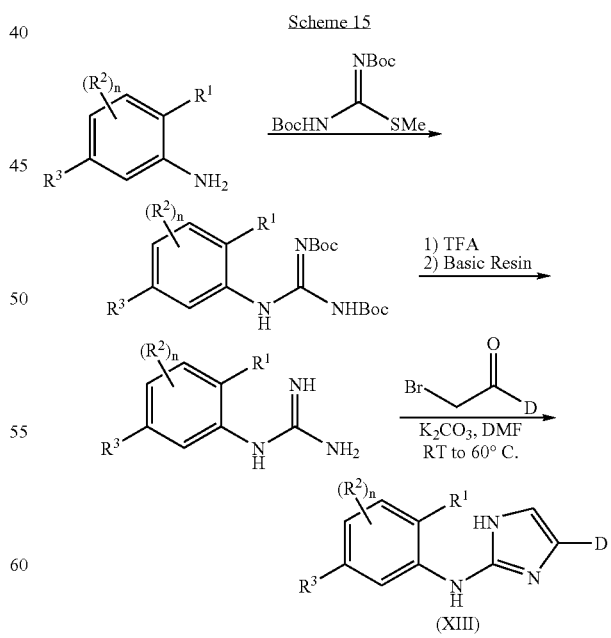

Amines attached to aryl or heteroaryl ring systems are useful as intermediates herein. There are many methods of preparing such intermediates known to one skilled in the art of organic chemistry. Several methods of preparing amines useful herein are illustrated in schemes 16-18.

Substituted aniline of type (XV) can be prepared from commercially available methyl 4-iodobenzoate as depicted in scheme 16. Nitration followed by reduction of the nitro group yields the aniline. Palladium-catalyzed coupling with ethynyltrimethylsilane, followed by desilylation and saponification gives the desired ethynyl-substituted aminobenzoic acid. Coupling with methoxyamine using coupling agent EDC affords the desired aniline (XV). (*Eur. J. Org. Chem,* 4607 (2001))

yields the ethynyl-substituted aminobenzoic acid. Coupling with methoxyamine using coupling agent EDC affords the desired aniline (XV). (*Eur. J. Org. Chem.,* 4607 (2001))

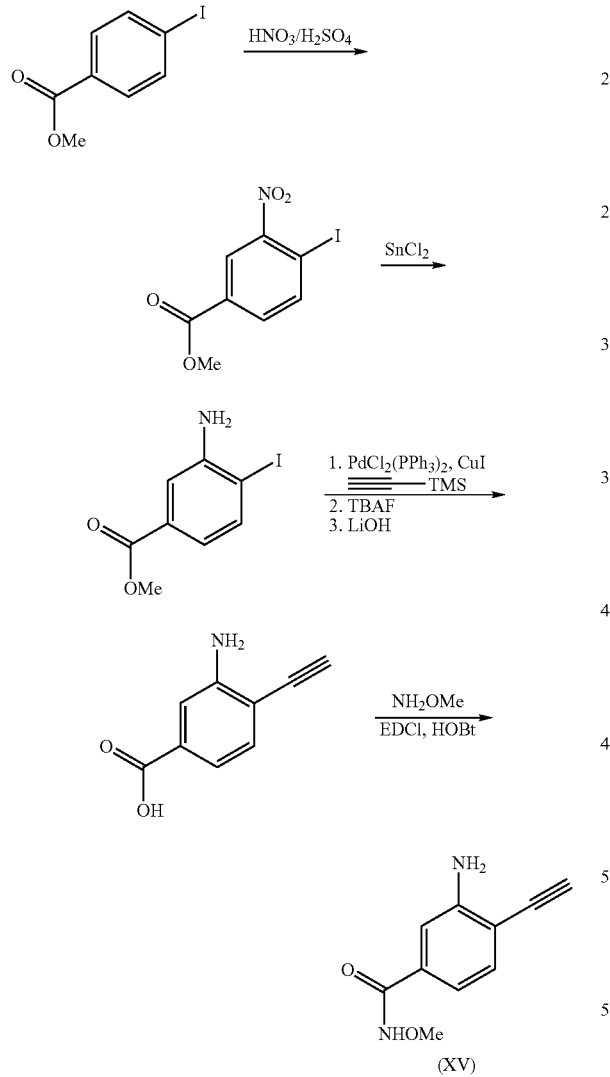

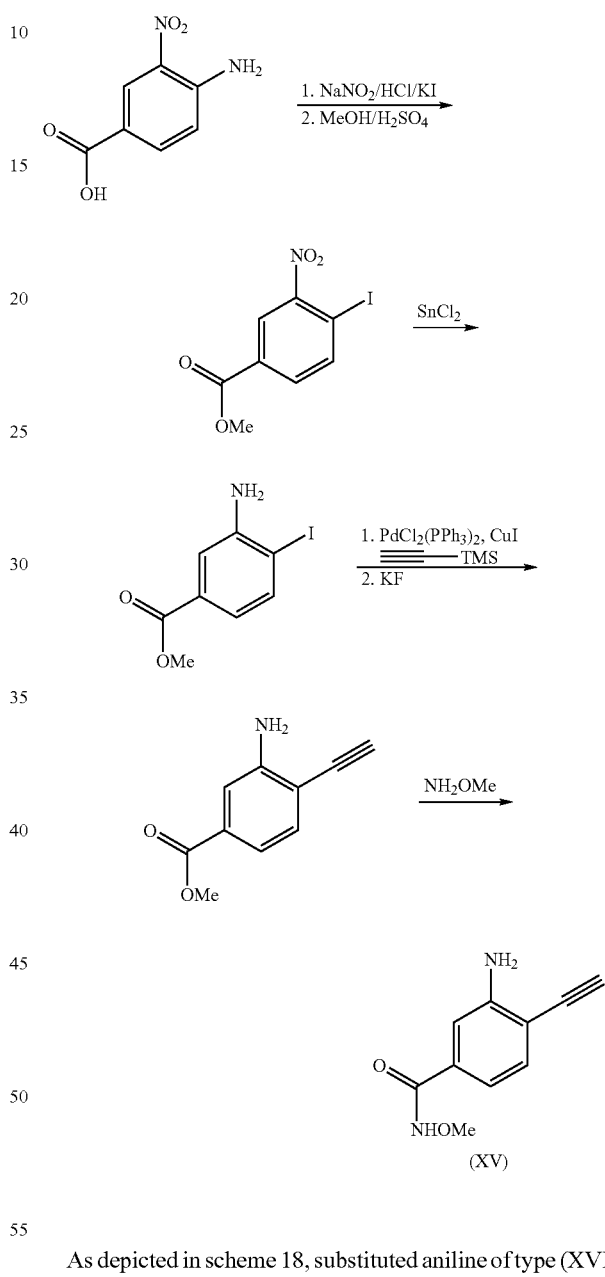

Alternatively, substituted aniline of type (XV) can be prepared 4-amino-3-nitrobenzoic acid as depicted in scheme 17. Iodide substitution of the aryldiazonium salt, followed by esterification with methanol gives methyl 4-iodo-3-nitrobenzoate. The nitro group can be reduced by SnCl$_4$ to give the desired aniline. Palladium catalyzed coupling with ethynyltrimethylsilane, followed by desilylation and saponification As depicted in scheme 18, substituted aniline of type (XVI) can be prepared from intermediate methyl 4-iodo-3-nitrobenzoate, which can be synthesized as shown in scheme 17. Palladium catalyzed coupling with vinyltributyltin followed by carbene addition to the resulty styrene double bond gives the cyclopropyl substituted methyl nitrobenzoate. Reduction of the nitro group followed by Boc protection and saponification gives the protected 3-amino-4-cyclopropylbenzoic acid. Coupling with an alkoxyamine using coupling agent EDC affords the desired aniline (XVI).

Scheme 18

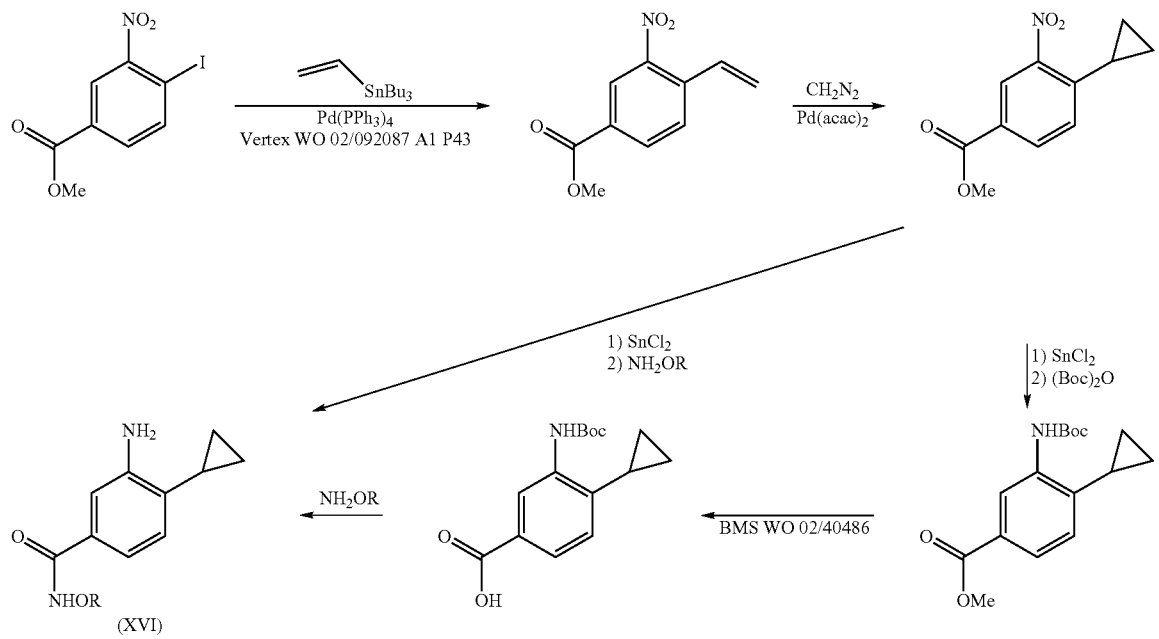

References of additional synthetic methods are as follows:
1) *J. Heterocyclic Chem.* 17, 631 (1980)
2) *Tetrahedron* 55(48), 13703 (1999)
3) EP 0 713 876
4) *Chemische Berichte* 126(10), 2317 (1993)
5) *Journal of Organic Chem.* 58(24), 6620 (1993)
6) *Tetrahedron Letters* 35, 3239 (1973)
7) *Journal of Chemical Research, Synopses* 1, 2 (1997)
8) *Boletin de la Sociedad Quimica del Peru* 53(3), 150 (1987)
9) *Journal of the Chemical Society, Chemical Communications* 2, 35 (1973)
10) *Comptes Rendus des Seances de l'Academie des Sciences, Series C: Sciences Chimiques* 274(20), 1703 (1972)

D. Formulation of Pharmaceutical Compositions

The pharmaceutical compositions provided herein contain therapeutically effective amounts of one or more of the cytokine activity modulators provided herein that are useful in the prevention, treatment, or amelioration of one or more of the symptoms of diseases or disorders associated with cytokine activity, in one embodiment, p38 kinase activity. Such diseases or disorders include, but are not limited to, inflammatory diseases, autoimmune diseases, destructive bone disorders, proliferative disorders, angiogenic disorders, infectious diseases, neurodegenerative diseases, and viral diseases.

The compositions contain one or more compounds provided herein. The compounds are formulated into suitable pharmaceutical preparations such as solutions, suspensions, tablets, dispersible tablets, pills, capsules, powders, sustained release formulations or elixirs, for oral administration or in sterile solutions or suspensions for parenteral administration, as well as transdermal patch preparation and dry powder inhalers. Typically the compounds described above are formulated into pharmaceutical compositions using techniques and procedures well known in the art (see, e.g., Ansel *Introduction to Pharmaceutical Dosage Forms, Fourth Edition* 1985, 126).

In the compositions, effective concentrations of one or more compounds or pharmaceutically acceptable derivatives is (are) mixed with a suitable pharmaceutical carrier or vehicle. The compounds may be derivatized as the corresponding salts, esters, enol ethers or esters, acids, bases, solvates, hydrates or prodrugs prior to formulation, as described above. The concentrations of the compounds in the compositions are effective for delivery of an amount, upon administration, that treats, prevents, or ameliorates one or more of the symptoms of diseases or disorders associated with cytokine activity or in which cytokine activity is implicated. Such diseases or disorders include, but are not limited to, inflammatory diseases, autoimmune diseases, destructive bone disorders, proliferative disorders, angiogenic disorders, infectious diseases, neurodegenerative diseases, and viral diseases.

Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

In addition, the compounds may be formulated as the sole pharmaceutically active ingredient in the composition or may be combined with other active ingredients. Liposomal suspensions, including tissue-targeted liposomes, such as tumor-targeted liposomes, may also be suitable as pharmaceutically acceptable carriers. These may be prepared according to methods known to those skilled in the art. For example, liposome formulations may be prepared as described in U.S. Pat. No. 4,522,811. Briefly, liposomes such as multilamellar vesicles (MLV's) may be formed by drying down egg phosphatidyl choline and brain phosphatidyl serine (7:3 molar ratio) on the inside of a flask. A solution of a compound provided herein in phosphate buffered saline lacking divalent cations (PBS) is added and the flask shaken until the lipid film is dispersed. The resulting vesicles are washed to remove unencapsulated compound, pelleted by centrifugation, and then resuspended in PBS.

The active compound is included in the pharmaceutically acceptable carrier in an amount sufficient to exert a therapeutically useful effect in the absence of undesirable side effects on the patient treated.

The concentration of active compound in the pharmaceutical composition will depend on absorption, inactivation and excretion rates of the active compound, the physicochemical characteristics of the compound, the dosage schedule, and amount administered as well as other factors known to those of skill in the art. For example, the amount that is delivered is sufficient to ameliorate one or more of the symptoms of diseases or disorders associated with cytokine activity or in which cytokine activity is implicated, as described herein.

The effective amount of a compound of provided herein may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

The active ingredient may be administered at once, or may be divided into a number of smaller doses to be administered at intervals of time. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions.

Pharmaceutically acceptable derivatives include acids, bases, enol ethers and esters, salts, esters, hydrates, solvates and prodrug forms. The derivative is selected such that its pharmacokinetic properties are superior to the corresponding neutral compound.

Thus, effective concentrations or amounts of one or more of the compounds described herein or pharmaceutically acceptable derivatives thereof are mixed with a suitable pharmaceutical carrier or vehicle for systemic, topical or local administration to form pharmaceutical compositions. Compounds are included in an amount effective for ameliorating one or more symptoms of, or for treating or preventing diseases or disorders associated with cytokine activity or in which cytokine activity is implicated, as described herein. The concentration of active compound in the composition will depend on absorption, inactivation, excretion rates of the active compound, the dosage schedule, amount administered, particular formulation as well as other factors known to those of skill in the art.

The compositions are intended to be administered by a suitable route, including orally in form of capsules, tablets, granules, powders or liquid formulations including syrups; parenterally, such as subcutaneously, intravenously, intramiscularly, with inteasternal injection or infusion techniques (as sterile injectable aq. or non-aq. solutions or suspensions); nasally such as by inhalation spray; topically, such as in the form of a cream or ointment; rectally such as in the form of suppositories; liposomally; and locally. The compositions can be in liquid, semi-liquid or solid form and are formulated in a manner suitable for each route of administration. In certain embodiments, administration of the formulation include parenteral and oral modes of administration. In one embodiment, the compositions are administered orally.

Solutions or suspensions used for parenteral, intradermal, subcutaneous, or topical application can include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using cosolvents, such as dimethylsulfoxide (DMSO), using surfactants, such as TWEEN®, or dissolution in aqueous sodium bicarbonate. Derivatives of the compounds, such as prodrugs of the compounds may also be used in formulating effective pharmaceutical compositions.

Upon mixing or addition of the compound(s), the resulting mixture may be a solution, suspension, emulsion or the like. The form of the resulting mixture depends upon a number of factors, including the intended mode of administration and the solubility of the compound in the selected carrier or vehicle. The effective concentration is sufficient for ameliorating the symptoms of the disease, disorder or condition treated and may be empirically determined.

The pharmaceutical compositions are provided for administration to humans and animals in unit dosage forms, such as tablets, capsules, pills, powders, granules, sterile parenteral solutions or suspensions, and oral solutions or suspensions, and oil-water emulsions containing suitable quantities of the compounds or pharmaceutically acceptable derivatives thereof. The pharmaceutically therapeutically active compounds and derivatives thereof are typically formulated and administered in unit-dosage forms or multiple-dosage forms. Unit-dose forms as used herein refers to physically discrete units suitable for human and animal subjects and packaged individually as is known in the art. Each unit-dose contains a predetermined quantity of the therapeutically active compound sufficient to produce the desired therapeutic effect, in association with the required pharmaceutical carrier, vehicle or diluent. Examples of unit-dose forms include ampoules and syringes and individually packaged tablets or capsules. Unit-dose forms may be administered in fractions or multiples thereof. A multiple-dose form is a plurality of identical unit-dosage forms packaged in a single container to be administered in segregated unit-dose form. Examples of multiple-dose forms include vials, bottles of tablets or capsules or bottles of pints or gallons. Hence, multiple dose form is a multiple of unit-doses which are not segregated in packaging.

The composition can contain along with the active ingredient: a diluent such as lactose, sucrose, dicalcium phosphate, or carboxymethylcellulose; a lubricant, such as magnesium stearate, calcium stearate and talc; and a binder such as starch, natural gums, such as gum acaciagelatin, glucose, molasses, polyinylpyrrolidine, celluloses and derivatives thereof, povidone, crospovidones and other such binders known to those of skill in the art. Liquid pharmaceutically administrable compositions can, for example, be prepared by dissolving, dispersing, or otherwise mixing an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, acetate, sodium citrate, cyclodextrine derivatives, sorbitan monolaurate, triethanolamine sodium acetate, triethanolamine oleate, and other such agents. Actual methods of preparing such dosage forms are known, or will be apparent, to those skilled in this art; for example, see Remington's Pharmaceutical Sciences, Mack Publishing Company, Easton, Pa., 15th Edition, 1975. The composition or formulation to be administered will, in any event, contain a quantity of the active compound in an amount sufficient to alleviate the symptoms of the treated subject.

Dosage forms or compositions containing active ingredient in the range of 0.005% to 100% with the balance made up from-non-toxic carrier may be prepared. For oral administration, a pharmaceutically acceptable non-toxic composition is formed by the incorporation of any of the normally employed excipients, such as, for example pharmaceutical grades of mannitol, lactose, starch, magnesium stearate, talcum, cellulose derivatives, sodium crosscarmellose, glucose, sucrose, magnesium carbonate or sodium saccharin. Such compositions include solutions, suspensions, tablets, capsules, powders and sustained release formulations, such as, but not limited to, implants and microencapsulated delivery systems, and biodegradable, biocompatible polymers, such as collagen, ethylene vinyl acetate, polyanhydrides, polyglycolic acid, polyorthoesters, polylactic acid and others. Methods for preparation of these compositions are known to those skilled in the art. The contemplated compositions may contain 0.001%-100% active ingredient, in one embodiment 0.1-85%, in another embodiment 75-95%.

The compounds may be administered in a form suitable for immediate release or extended release. Immediate release or extended release may be achieved with suitable pharmaceutical compositions or, particularly in the case of extended release, with devices such as subcutaneous implants or osmotic pumps. Exemplary compositions for topical administration include a topical carrier such as PLASTIBASE® (mineral oil gelled with polyethylene).

The compositions may include other active compounds to obtain desired combinations of properties. The compounds provided herein, or pharmaceutically acceptable derivatives thereof as described herein, may also be advantageously administered for therapeutic or prophylactic purposes together with another pharmacological agent known in the general art to be of value in treating one or more of the diseases or medical conditions referred to hereinabove, such as diseases or disorders associated with nuclear receptor activity or in which nuclear receptor activity is implicated. It is to be understood that such combination therapy constitutes a further aspect of the compositions and methods of treatment provided herein.

1. Compositions for Oral Administration

Oral pharmaceutical dosage forms are either solid, gel or liquid. The solid dosage forms are tablets, capsules, granules, and bulk powders. Types of oral tablets include compressed, chewable lozenges and tablets which may be enteric-coated, sugar-coated or film-coated. Capsules may be hard or soft gelatin capsules, while granules and powders may be provided in non-effervescent or effervescent form with the combination of other ingredients known to those skilled in the art.

In certain embodiments, the formulations are solid dosage forms, preferably capsules or tablets. The tablets, pills, capsules, troches and the like can contain any of the following ingredients, or compounds of a similar nature: a binder; a diluent; a disintegrating agent; a lubricant; a glidant; a sweetening agent; and a flavoring agent.

Examples of binders include microcrystalline cellulose, gum tragacanth, glucose solution, acacia mucilage, gelatin solution, sucrose and starch paste. Lubricants include talc, starch, magnesium or calcium stearate, *lycopodium* and stearic acid. Diluents include, for example, lactose, sucrose, starch, kaolin, salt, mannitol and dicalcium phosphate. Glidants include, but are not limited to, colloidal silicon dioxide. Disintegrating agents include crosscarmellose sodium, sodium starch glycolate, alginic acid, sodium alginate, corn starch, potato starch, bentonite, methylcellulose, agar and carboxymethylcellulose. Coloring agents include, for example, any of the approved certified water soluble FD and C dyes, mixtures thereof; and water insoluble FD and C dyes suspended on alumina hydrate. Sweetening agents include sucrose, lactose, mannitol and artificial sweetening agents such as saccharin, and any number of spray dried flavors. Flavoring agents include natural flavors extracted from plants such as fruits and synthetic blends of compounds which produce a pleasant sensation, such as, but not limited to peppermint and methyl salicylate. Wetting agents include propylene glycol monostearate, sorbitan monooleate, diethylene glycol monolaurate and polyoxyethylene laural ether. Emetic-coatings include fatty acids, fats, waxes, shellac, ammoniated shellac and cellulose acetate phthalates. Film coatings include hydroxyethylcellulose, sodium carboxymethylcellulose, polyethylene glycol 4000 and cellulose acetate phthalate.

If oral administration is desired, the compound could be provided in a composition that protects it from the acidic environment of the stomach. For example, the composition can be formulated in an enteric coating that maintains its integrity in the stomach and releases the active compound in the intestine. The composition may also be formulated in combination with an antacid or other such ingredient.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar and other enteric agents. The compounds can also be administered as a component of an elixir, suspension, syrup, wafer, sprinkle, chewing gum or the like. A syrup may contain, in addition to the active compounds, sucrose as a sweetening agent and certain preservatives, dyes and colorings and flavors.

The active materials can also be mixed with other active materials which do not impair the desired action, or with materials that supplement the desired action, such as antacids, H2 blockers, and diuretics. The active ingredient is a compound or pharmaceutically acceptable derivative thereof as described herein. Higher concentrations, up to about 98% by weight of the active ingredient may be included.

Pharmaceutically acceptable carriers included in tablets are binders, lubricants, diluents, disintegrating agents, coloring agents, flavoring agents, and wetting agents. Enteric-coated tablets, because of the enteric-coating, resist the action of stomach acid and dissolve or disintegrate in the neutral or alkaline intestines. Sugar-coated tablets are compressed tablets to which different layers of pharmaceutically acceptable substances are applied. Film-coated tablets are compressed tablets which have been coated with a polymer or other suitable coating. Multiple compressed tablets are compressed tablets made by more than one compression cycle utilizing the pharmaceutically acceptable substances previously mentioned. Coloring agents may also be used in the above dosage forms. Flavoring and sweetening agents are used in compressed tablets, sugar-coated, multiple compressed and chewable tablets. Flavoring and sweetening agents are especially useful in the formation of chewable tablets and lozenges.

Liquid oral dosage forms include aqueous solutions, emulsions, suspensions, solutions and/or suspensions reconstituted from non-effervescent granules and effervescent preparations reconstituted from effervescent granules. Aqueous solutions include, for example, elixirs and syrups. Emulsions are either oil-in-water or water-in-oil.

Elixirs are clear, sweetened, hydroalcoholic preparations. Pharmaceutically acceptable carriers used in elixirs include solvents. Syrups are concentrated aqueous solutions of a sugar, for example, sucrose, and may contain a preservative. An emulsion is a two-phase system in which one liquid is dispersed in the form of small globules throughout another liquid. Pharmaceutically acceptable carriers used in emulsions are non-aqueous liquids, emulsifying agents and preservatives. Suspensions use pharmaceutically acceptable suspending agents and preservatives. Pharmaceutically acceptable substances used in non-effervescent granules, to be reconstituted into a liquid oral dosage form, include diluents, sweeteners and wetting agents. Pharmaceutically acceptable substances used in effervescent granules, to be reconstituted into a liquid oral dosage form, include organic acids and a source of carbon dioxide. Coloring and flavoring agents are used in all of the above dosage forms.

Solvents include glycerin, sorbitol, ethyl alcohol and syrup. Examples of preservatives include glycerin, methyl and propylparaben, benzoic add, sodium benzoate and alcohol. Examples of non-aqueous liquids utilized in emulsions include mineral oil and cottonseed oil. Examples of emulsifying agents include gelatin, acacia, tragacanth, bentonite, and surfactants such as polyoxyethylene sorbitan monooleate. Suspending agents include sodium carboxymethylcellulose, pectin, tragacanth, Veegum and acacia. Diluents include lactose and sucrose. Sweetening agents include sucrose, syrups, glycerin and artificial sweetening agents such as saccharin. Wetting agents include propylene glycol monostearate, sorbitan monooleate, diethylene glycol monolaurate and polyoxyethylene lauryl ether. Organic adds include citric and tartaric acid. Sources of carbon dioxide include sodium bicarbonate and sodium carbonate. Coloring agents include any of the approved certified water soluble FD and C dyes, and mixtures thereof. Flavoring agents include natural flavors extracted from plants such fruits, and synthetic blends of compounds which produce a pleasant taste sensation.

For a solid dosage form, the solution or suspension, in for example propylene carbonate, vegetable oils or triglycerides, is preferably encapsulated in a gelatin capsule. Such solutions, and the preparation and encapsulation thereof, are disclosed in U.S. Pat. Nos. 4,328,245; 4,409,239; and 4,410,545. For a liquid dosage form, the solution, e.g., for example, in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and other such carriers, and encapsulating these solutions or suspensions in hard or soft gelatin capsule shells. Other useful formulations include those set forth in U.S. Pat. Nos. Re 28,819 and 4,358,603. Briefly, such formulations include, but are not limited to, those containing a compound provided herein, a dialkylated mono- or poly-alkylene glycol, including, but not limited to, 1,2-dimethoxymethane, diglyme, triglyme, tetraglyme, polyethylene glycol-350-dimethyl ether, polyethylene glycol-550-dimethyl ether, polyethylene glycol-750-dimethyl ether wherein 350, 550 and 750 refer to the approximate average molecular weight of the polyethylene glycol, and one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, thiodipropionic acid and its esters, and dithiocarbamates.

Other formulations include, but are not limited to, aqueous alcoholic solutions including a pharmaceutically acceptable acetal. Alcohols used in these formulations are any pharmaceutically acceptable water-miscible solvents having one or more hydroxyl groups, including, but not limited to, propylene glycol and ethanol. Acetals include, but are not limited to, di(lower alkyl) acetals of lower alkyl aldehydes such as acetaldehyde diethyl acetal.

In all embodiments, tablets and capsules formulations may be coated as known by those of skill in the art in order to modify or sustain dissolution of the active ingredient. Thus, for example, they may be coated with a conventional enterically digestible coating, such as phenylsalicylate, waxes and cellulose acetate phthalate.

Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., GANTREZ®); and agents to control release such as polyacrylic copolymer (e.g., CARBOPOL 934®). Lubricants, glidants, flavors, coloring agents and stabilizers may also be added for ease of fabrication and use.

2. Injectables, Solutions and Emulsions

Parenteral administration, generally characterized by injection, either subcutaneously, intramuscularly or intravenously is also contemplated herein. Injectables can be prepared in conventional forms, either as liquid solutions or suspensions, solid forms suitable for solution or suspension in liquid prior to injection, or as emulsions. Suitable excipients are, for example, water, saline, dextrose, glycerol, mannitol, 1,3-butanediol, Ringer's solution, an isotonic sodium chloride solution or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, mono-or diglycerides, fatty acids, such as oleic acid, sodium acetate, sorbitan monolaurate, triethanolamine oleate and cyclodextrins. Implantation of a slow-release or sustained-release system, such that a constant level of dosage is maintained (see, e.g., U.S. Pat. No. 3,710,795) is also contemplated herein. Briefly, a compound provided herein is dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The compound diffuses through the outer polymeric membrane in a release rate controlling step. The percentage of active compound contained in such parenteral compositions is highly dependent on the specific nature thereof, as well as the activity of the compound and the needs of the subject.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

If administered intravenously, suitable carriers include physiological saline or phosphate buffered saline (PBS), and solutions containing thickening and solubilizing agents, such as glucose, polyethylene glycol, and polypropylene glycol and mixtures thereof.

Pharmaceutically acceptable carriers used in parenteral preparations include aqueous vehicles, nonaqueous vehicles, antimicrobial agents, isotonic agents, buffers, antioxidants, local anesthetics, suspending and dispersing agents, emulsifying agents, sequestering or chelating agents and other pharmaceutically acceptable substances.

Examples of aqueous vehicles include Sodium Chloride Injection, Ringers Injection, Isotonic Dextrose Injection, Sterile Water Injection, Dextrose and Lactated Ringers Injection. Nonaqueous parenteral vehicles include fixed oils of vegetable origin, cottonseed oil, corn oil, sesame oil and peanut oil. Antimicrobial agents in bacteriostatic or fungistatic concentrations must be added to parenteral preparations packaged in multiple-dose containers which include phenols or cresols, mercurials, benzyl alcohol, chlorobutanol, methyl and propyl p-hydroxybenzoic acid esters, thimerosal, benzalkonium chloride and benzethonium chloride. Isotonic agents include sodium chloride and dextrose. Buffers include phosphate and citrate. Antioxidants include sodium bisulfate. Local anesthetics include procaine hydrochloride. Suspending and dispersing agents include sodium carboxymethylcelluose, hydroxypropyl methylcellulose and polyvinylpyrrolidone. Emulsifying agents include Polysorbate 80 (TWEEN® 80). A sequestering or chelating agent of metal ions include EDTA. Pharmaceutical carriers also include ethyl alcohol, polyethylene glycol and propylene glycol for water miscible vehicles and sodium hydroxide, hydrochloric acid, citric acid or lactic acid for pH adjustment.

The concentration of the pharmaceutically active compound is adjusted so that an injection provides an effective amount to produce the desired pharmacological effect. The exact dose depends on the age, weight and condition of the patient or animal as is known in the art.

The unit-dose parenteral preparations are packaged in an ampoule, a vial or a syringe with a needle. All preparations for parenteral administration must be sterile, as is known and practiced in the art.

Illustratively, intravenous or intraarterial infusion of a sterile aqueous solution containing an active compound is an effective mode of administration. Another embodiment is a sterile aqueous or oily solution or suspension containing an active material injected as necessary to produce the desired pharmacological effect.

Injectables are designed for local and systemic administration. Typically a therapeutically effective dosage is formulated to contain a concentration of at least about 0.1% w/w up to about 90% w/w or more, preferably more than 1% w/w of the active compound to the treated tissue(s). The active ingredient may be administered at once, or may be divided into a number of smaller doses to be administered at intervals of time. It is understood that the precise dosage and duration of treatment is a function of the tissue being treated and may be determined empirically using known testing protocols or by extrapolation from in vivo or in vitro test data. It is to be noted that concentrations and dosage values may also vary with the age of the individual treated. It is to be further understood that for any particular subject, specific dosage regimens should be adjusted over time according to the individual need and the professional judgment of the person administering or supervising the administration of the formulations, and that the concentration ranges set forth herein are exemplary only and are not intended to limit the scope or practice of the claimed formulations.

The compound may be suspended in micronized or other suitable form or may be derivatized to produce a more soluble active product or to produce a prodrug. The form of the resulting mixture depends upon a number of factors, including the intended mode of administration and the solubility of the compound in the selected carrier or vehicle. The effective concentration is sufficient for ameliorating the symptoms of the condition and may be empirically determined.

3. Lyophilized Powders

Of interest herein are also lyophilized powders, which can be reconstituted for administration as solutions, emulsions and other mixtures. They may also be reconstituted and formulated as solids or gels.

The sterile, lyophilized powder is prepared by dissolving a compound provided herein, or a pharmaceutically acceptable derivative thereof, in a suitable solvent. The solvent may contain an excipient which improves the stability or other pharmacological component of the powder or reconstituted solution, prepared from the powder. Excipients that may be used include, but are not limited to, dextrose, sorbital, fructose, corn syrup, xylitol, glycerin, glucose, sucrose or other suitable agent. The solvent may also contain a buffer, such as citrate, sodium or potassium phosphate or other such buffer known to those of skill in the art at, typically, about neutral pH. Subsequent sterile filtration of the solution followed by lyophilization under standard conditions known to those of skill in the art provides the desired formulation. Generally, the resulting solution will be apportioned into vials for lyophilization. Each vial will contain a single dosage 10-1000 mg, in one embodiment, 100-500 mg or multiple dosages of the compound. The lyophilized powder can be stored under appropriate conditions, such as at about 4° C. to room temperature.

Reconstitution of this lyophilized powder with water for injection provides a formulation for use in parenteral administration. For reconstitution, about 1-50 mg, preferably 5-35 mg, more preferably about 9-30 mg of lyophilized powder, is added per mL of sterile water or other suitable carrier. The precise amount depends upon the selected compound. Such amount can be empirically determined.

4. Topical Administration

Topical mixtures are prepared as described for the local and systemic administration. The resulting mixture may be a solution, suspension, emulsions or the like and are formulated as creams, gels, ointments, emulsions, solutions, elixirs, lotions, suspensions, tinctures, pastes, foams, aerosols, irrigations, sprays, suppositories, bandages, dermal patches or any other formulations suitable for topical administration.

The compounds or pharmaceutically acceptable derivatives thereof may be formulated as aerosols for topical application, such as by inhalation (see, e.g., U.S. Pat. Nos. 4,044,126, 4,414,209, and 4,364,923, which describe aerosols for delivery of a steroid useful for treatment of inflammatory diseases, particularly asthma). These formulations for administration to the respiratory tract can be in the form of an aerosol or solution for a nebulizer, or as a microfine powder for insufflation, alone or in combination with an inert carrier such as lactose. In such a case, the particles of the formulation will typically have diameters of less than 50 microns, preferably less than 10 microns.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

The compounds may be formulated for local or topical application, such as for topical application to the skin and mucous membranes, such as in the eye, in the form of gels, creams, and lotions and for application to the eye or for intracisternal or intraspinal application. Topical administration is contemplated for transdermal delivery and also for administration to the eyes or mucosa, or for inhalation therapies. Nasal solutions of the active compound alone or in combination with other pharmaceutically acceptable excipients can also be administered.

These solutions, particularly those intended for ophthalmic use, may be formulated as 0.01%-10% isotonic solutions, pH about 5-7, with appropriate salts.

5. Compositions for Other Routes of Administration

Other routes of administration, such as topical application, transdermal patches, and rectal administration are also contemplated herein.

For example, pharmaceutical dosage forms for rectal administration are rectal suppositories, capsules and tablets for systemic effect. Rectal suppositories are used herein mean solid bodies for insertion into the rectum which melt or soften at body temperature releasing one or more pharmacologically or therapeutically active ingredients. Pharmaceutically acceptable substances utilized in rectal suppositories are bases or vehicles and agents to raise the melting point. Examples of bases include cocoa butter (theobroma oil), glycerin-gelatin, carbowax (polyoxyethylene glycol) and appropriate mixtures of mono-, di- and triglycerides of fatty acids. Combinations of the various bases may be used. Agents to raise the melting point of suppositories include spermaceti and wax. Rectal suppositories may be prepared either by the compressed method or by molding. The typical weight of a rectal suppository is about 2 to 3 gm.

Tablets and capsules for rectal administration are manufactured using the same pharmaceutically acceptable substance and by the same methods as for formulations for oral administration.

6. Articles of Manufacture

The compounds or pharmaceutically acceptable derivatives may be packaged as articles of manufacture containing packaging material, a compound or pharmaceutically acceptable derivative thereof provided herein, which is effective for modulating the activity of cytokines, in one embodiment, the activity of p38 kinases, or for treatment, prevention or amelioration of one or more symptoms of cytokine, in one embodiment, p38 kinase, mediated diseases or disorders, or diseases or disorders in which cytokine activity, in one embodiment, p38 kinase activity, is implicated, within the packaging material, and a label that indicates that the compound or composition, or pharmaceutically acceptable derivative thereof, is used for modulating the activity of cytokines, in one embodiment, p38 kinases, or for treatment, prevention or amelioration of one or more symptoms of cytokine, in one embodiment, p38 kinase, mediated diseases or disorders, or diseases or disorders in which cytokine activity, in one embodiment, p38 kinase activity, is implicated.

The articles of manufacture provided herein contain packaging materials. Packaging materials for use in packaging pharmaceutical products are well known to those of skill in the art. See, e.g., U.S. Pat. Nos. 5,323,907, 5,052,558 and 5,033,252. Examples of pharmaceutical packaging materials include, but are not limited to, blister packs, bottles, tubes, inhalers, pumps, bags, vials, containers, syringes, bottles, and any packaging material suitable for a selected formulation and intended mode of administration and treatment. A wide array of formulations of the compounds and compositions provided herein are contemplated as are a variety of treatments for any disease or disorder in which cytokine activity, in one embodiment, p38 kinase activity, is implicated as a mediator or contributor to the symptoms or cause.

E. Evaluation of the Activity of the Compounds

Standard physiological, pharmacological and biochemical procedures are available for testing the compounds to identify those that possess biological activities that modulate the activity of cytokines, including the p38 kinase activity.

Compound inhibitory activity was measured in a radioactive enzyme assay. The buffer composition was adopted from Lisnock et al (Biochemistry, 1998, vol. 37, pp 16573-16581). Peptide substrate was selected from Chen et al (Biochemistry, 2000, vol. 39, 2079-2087). The concentrations of p38α, [γ-$^{33}$P-ATP] and peptide were equal 1 nM, 85 uM and 250 uM, respectively. Incorporation of $^{33}$P into peptide was measured using absorption on filtermats with subsequent wash with 100 mM phosphoric acid followed by ethanol.

Other conditions for the p38α enzymatic assay were also described in literature. They either differed from the assay described in either buffer composition (Biochemistry, 2000, vol. 39, 2079-2087)), or substrate (Biochemistry, 1998, vol. 37, pp 16573-16581), or both (Protein Sci., 1998, vol. 7, pp. 2249-2255).

F. Methods of use of the Compounds and Compositions

In certain embodiments, the compounds provided herein are selective inhibitors of p38 kinase activity, and in one embodiment, the compounds are inhibitors of isoforms of p38 kinase, including, but not limited to p38α and p38β kinases. Accordingly, compounds of formula (I) have utility in treating conditions associated with p38 kinase activity. Such conditions include diseases in which cytokine levels are modulated as a consequence of intracellular signaling via p38, and in particular, diseases that are associated with an overproduction of cytokines IL-1, IL-4, IL-8, and TNF-α.

In view of their activity as inhibitors of p38α/β kinase, compounds of Formula (I are useful in treating p38 associated conditions including, but not limited to, inflammatory diseases, autoimmune diseases, destructive bone disorders, proliferative disorders, angiogenic disorders, infectious diseases, neurodegenerative diseases, and viral diseases.

Inflammatory diseases related to p38-associated condition include, but are not limited to acute pancreatitis, chronic pancreatitis, asthma, allergies, and adult respiratory distress syndrome.

Autoimmune diseases related to p38-associated condition include, but are not limited to, glomeralonephritis, rheumatoid arthritis, systemic lupus erythematosus, scleroderma, chronic thyroiditis, Graves' disease, autoimmune gastritis, insulin-dependent diabetes mellitus (Type I), autoimmune hemolytic anemia, autoimmune neutropenia, thrombocytopenia, atopic dermnatitis, chronic active hepatitis, myasthenia gravis, multiple sclerosis, inflammatory bowel disease, ulcerative colitis, Crohn's disease, psoriasis, or graft vs. host disease.

Destructive bone disorders related to p38-associated condition include, but are not limited to, osteoporosis, osteoarthritis and multiple myeloma-related bone disorder.

Proliferative diseases which are related to p38-associated condition include, but are not limited to, acute myelogenous leukemia, chronic myelogenous leukemia, metastatic melanoma, Kaposi's sarcoma, and multiple myeloma.

Infectious diseases related to p38-associated condition include, but are not limited to, sepsis, septic shock, and Shigellosis.

Viral diseases related to p38-associated condition include, but are not limited to, acute hepatitis infection (including hepatitis A, hepatitis B and hepatitis C), HIV infection and CMV retinitis.

Degenerative or diseases related to p38-associated condition include, but are not limited to, Alzheimer's disease, Parkinson's disease, cerebral ischemia, and other neurodegenerative diseases.

"p38-associated conditions" also include ischemia/reperfusion in stroke, heart attacks, myocardial ischemia, organ hypoxia, vascular hyperplasia, cardiac hypertrophy, and thrombin-induced platelet aggregation.

In addition, p38 inhibitors provided herein are also capable of inhibiting the expression of inducible pro-inflammatory proteins such as prostaglandin endoperoxide synthase-2 (PGHS-2), also referred to as cyclooxygenase-2 (COX-2). Therefore, other "p38-mediated conditions" are edema, analgesia, fever and pain, such as neuromuscular pain, headache, cancer pain, dental pain and arthritis pain.

The diseases that may be treated or prevented by the p38 inhibitors provided herein, may also be conveniently grouped by the cytokine (IL-1, TNF, IL-6, IL-8) that is believed to be responsible for the disease.

Thus, an IL-1-mediated disease or condition includes rheumatoid arthritis, osteoarthritis, stroke, endotoxemia and/or toxic shock syndrome, inflammatory reaction induced by endotoxin, inflammatory bowel disease, tuberculosis, atherosclerosis, muscel degeneration, cachexia, psoriatic arthritis, Reiter's syndrome, gout, traumatic arthritis, rubella arthritis, acute synovitis, diabetes, pancreatic .beta.-cell disease and Alzheimer's disease.

TNF-mediated disease or condition includes, rheumatoid arthritis, rheumatoid spndylitis, osteoarthritis, gouty arthritis and other arthritic conditions, sepsis, septic shock, endotoxic shock, gram negative sepsis, toxic shock syndrome, adult respiratory distress syndrome, cerebral malaria, chronic pulmonary inflammatory disease, silicosis, pulmonary sarcoisosis, bone resorption diseases, reperfusion injury, graft vs. host reaction, allograft rejections, fever and myalgias due to infection, cachexia secondary to infection, AIDS, ARC or malignancy, keloid formation, scar tissue formation, Crohn's disease, ulcerative colitis or pyresis. TNF-mediated diseases also include viral infections, such as HIV, CMV, influenza and herpes; and vetinary viral infections, such as lentivirus infections, including, but not limited to equine infectious anaemia virus, caprine arthritis virus, visna virus or maedi virus; or retrovirus infections, including feline immunodeficiency virus, bovine immunodeficiency virus, or canine immunodeficiency virus.

IL-8 mediated disease or conditon includes diseases characterized by massive neutrophil infiltration, such as psoriasis, inflammatory bowel disease, asthma, cardiac and renal reperfusion injury, adult respiratory distress syndrome, thrombosis and glomerulonephritis.

In addition, the compounds provided herein may be used topically to treat or prevent conditions caused or exacerbated by IL-1 or TNF. Such conditions include inflamed joints, eczema, psoriasis, inflammatory skin conditions such as sunburn, inflammatory eye conditions such as conjuctivitis, pyresis, pain and other conditions associated with inflammation.

In one embodiment, the specific conditions or diseases that may be treated with the compounds provided herein include, but are not limited to, pancreatitis (acute or chronic), asthma, allergies, adult respiratory distress syndrome, chronic obstructive pulmonary disease, glomerulonephritis, rheumatoid arthritis, systemic lupus erythematosus, scleroderma, chronic thyroiditis, Grave's disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs. host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoisosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovascularization, and infantile haemangiomas; viral diseases including acute hepatitis infection (including hepatitis A, hepatitis B and hepatitis C), HIV infection and CMV retinitis, AIDS, SARS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin induced platelet aggregation, endotoxemia and/or toxic shock syndrome, and conditions associated with prostaglandin endoperoxidase synthase-2.

In addition, p38 inhibitors provided herein inhibit the expression of inducible pro-inflammatory proteins such as prostaglandin endoperoxide synthase-2 (PGHS-2), also referred to as cyclooxygenase-2 (COX-2). Accordingly, additional p38-associated conditions include edema, analgesia, fever and pain, such as neuromuscular pain, headache, pain caused by cancer, dental pain and arthritis pain. The compounds provided herein also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

G. Combination Therapy

Also provided herein are methods treating p38 kinase-associated conditions by administering to a subject in need thereof an effective amount of compounds of Formula (I) alone or in combination with each other and/or other suitable therapeutic agents useful in treating such conditions. Exemplary of such other therapeutic agents include corticosteroids, rolipram, calphostin, CSAIDs, 4-substituted imidazo (1,2-A) quinoxalines as disclosed in U.S. Pat. No. 4,200,750 and in S. Ceccarelli et al, "Imidazo(1,2-a)quinoxalin-4-amines: A Novel Class of Nonxanthine $A_1$ Adenosine Receptor Antagonists," *European Journal of Medicinal Chemistry* Vol. 33, (1998), at pp. 943-955; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, Prograf); cytotoxic drugs such as azathioprine and cyclophosphamide; TNF-α inhibitors such as tenidap, anti-TNF antibodies or soluble TNF receptor, and rapamycin (sirolimus or Rapamune) or derivatives thereof.

The above other therapeutic agents, when employed in combination with the compounds provided herein, may be used, for example, in those amounts indicated in the Physicians' Desk Reference (PDR) or as otherwise determined by one of ordinary skill in the art. In the methods provided herein, such other therapeutic agent(s) may be administered prior to, simultaneously with, or following the administration of the compounds provided herein.

The following Examples illustrate exemplary embodiments, and are not intended to limit the scope of the claims. Abbreviations employed in the Examples are defined herein. Compounds of the Examples are identified by the example and step in which they are prepared (for example, "1A" denotes the title compound of step A of Example 1), or by the example only where the compound is the title compound of the example (for example, "2" denotes the title compound of Example 2).

General Methods. Mass spectral data were obtained on a Thermo Finnigan LCQ Duo Ion Trap mass spectrometer. HPLC data were obtained on a $C_{18}$ Betasol column (2.1×50 mm) using gradient elution 10-90% (solvent A, acetonitrile+ 0.025% v TFA; solvent B, water+0.025% v TFA) over 6 minutes (flow rate 0.40 mL/min) or over 4 minutes (flow rate 0.50 mL/min). Purification by prepatory HPLC on a Thermo Hypersi-Keystone Betasil C18 column 250×21.2 mm, particle size 5 μm, mobile phase: A, water+0.025% TFA; B, acetonitrile+0.025% TFA; gradient from 40 to 70% B; flow rate 15 mL/min.

EXAMPLE 1

Preparation of N-methoxy-4-methyl-3-(5-phenyl-4H-[1,2,4]triazol-3-ylamino)-benzamide

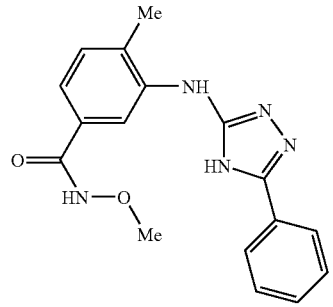

A. 3-(3-Benzoyl-thioureido)-N-methoxy-4-methyl-benzamide

To a stirred suspension of 3-amino-N-methoxy-4-methyl-benzamide (420 mg, 1.94 mmol, preparation: BMS WO 02/40486 A2, P66) in $CH_2Cl_2$ (10 ml) was added benzoyl isothiocyanate (332 mg, 2.03 mmol), followed by the addition of N,N-diisopropylethylamine (372 ul, 2.14 mmol). The reaction mixture was stirred at RT for one hour before it was washed with water, dried over $Na_2SO_4$, concentrated to give a crude. The mixture was then purified by a flash chromatography, eluting with 1:2 EtOAc/hexanes to give the benzamide 1A as an off-white solid (578 mg, 1.68 mmol, 87%). $^1$H NMR (300 MHz, DMSO-d$^6$) δ2.31 (s, 3H), 3.71 (s, 3H), 7.41 (d, J=8.4 Hz, 1H), 7.53-7.70 (m, 4H), 7.94 (s, 1H), 8.01 (d, J=7.4 Hz, 2H); MS m/z 343.9 [M+H]$^+$.

B. N-methoxy-4-methyl-3-(5-phenyl-4H-[1,2,4]triazol-3-ylamino)-benzamide

To a mixture of benzamide 1A in THF (2 ml) and EtOH (1 ml) was added hydrazine monohydrate. The mixture was then refluxed (bath T=77-80° C.) for 1.5 hr. It was cooled to room temperature and purified by preparative HPLC to give the title compound as a white solid (9.4 mg, 0.029 mmol, 9.0%). $^1$H NMR (300 MHz, CD$_3$OD) δ2.39 (s, 3H), 3.81 (s, 3H), 7.37 (d, J=7.9 Hz, 1H), 7.46 (d, J=7.9 Hz, 1H), 7.51-7.53 (m, 3H), 7.94-7.97 (m, 2H), 8.08 (s, 1H); MS m/z 324.0 [M+H]$^+$.

EXAMPLE 2

Preparation of N-methoxy-4-methyl-3-(5-phenyl-[1,2,4]oxadiazol-3-ylamino)-benzamide

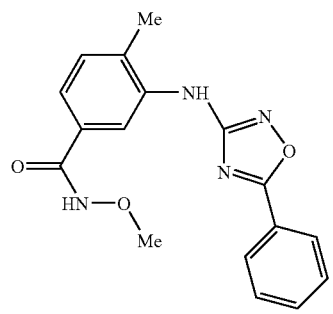

A. 3-(3-Benzoyl-2-methyl-isothioureido)-N-methoxy-4-methyl-benzamide

To a stirred suspension of 3-(3-Benzoyl-thioureido)-N-methoxy-4-methyl-benzamide (101 mg, 0.29 mmol, see preparation 1A) in CH$_2$Cl$_2$ (2 ml) was added THF (1 ml) to form a homogeneous solution. MeI (20 ul, 0.32 mmol) was added followed by N,N-diisopropylethylamine (56 ul, 0.32 mmol). The reaction mixture was stirred at RT for 2 hr. More MeI (40 ul, 0.64 mmol) and N,N-diisopropylethylamine (112 ul, 0.64 mmol) was added and the reaction was left to stir at RT overnight. The mixture was then poured into water, extracted twice with CH$_2$Cl$_2$. The combined organic extracts were dried over Na$_2$SO$_4$, concentrated and vacuum dried to give the title compound 2A as a white solid (113 mg), which was used for the next reaction without further purification. MS m/z 357.9 [M+H]$^+$.

B. N-Methoxy-4-methyl-3-(5-phenyl-[1,2,4]oxadiazol-3-ylamino)-benzamide

Hydroxylamine (58 ul, 0.58 mmol) was added to a suspension of compound 2A (113 mg, crude, ~0.29 mmol) in EtOH (1 ml). The mixture was heated at reflux for 1.5 hr. It was then cooled to RT, and purified by preparatory HPLC to give the title compound as a white solid (11.2 mg, 12% over two steps). $^1$H NMR (300 MHz, CD$_3$OD), δ2.41 (s, 3H), 3.82 (s, 3H), 7.31-7.40 (m, 2H), 7.59-7.66 (m, 3H), 8.13-8.18 (m, 3H); MS m/z 324.9 [M+H]$^+$.

EXAMPLE 3

Preparation of N-Cyclopropyl-4-methyl-3-(4-phenyl-thiazol-2-ylamino)-benzamide

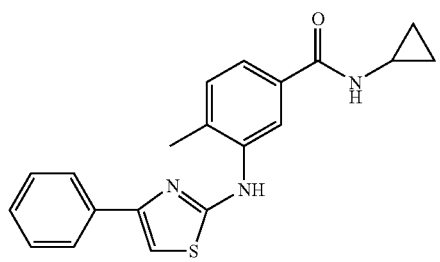

A. 3-Amino-N-cyclopropyl-4-methyl-benzamide

To a mixture of 3-amino-4-methyl-benzoic acid (10.2 g, 67.5 mmol) and cyclopropyl amine (9.33 mL, 135.0 mmol, 2 eq) in DMF (150 mL) was added EDCI (15.5 g, 81 mmol, 1.2 eq) followed by DMAP (cat.) at RT. The reaction was stirred overnight at RT, then concentrated. The residue was redissolved in water and extracted with EtOAc. The organic layer was washed with aqueous NaCl solution, dried over Na$_2$SO$_4$, and concentrated. The crude product was purified by flash chromatography on silica gel (gradient elution: 1:1 EtOAc/hexanes then 100% EtOAc) to provide 3A as a solid (9.5 g, 72%).

B. N-Cyclopropyl-3-isothiocyanato-4-methyl-benzamide

To a solution of 1,1'-thiocarbonyldi-2(1H)-pyridone (10.35 g, 44.6 mmol) in 20 mL of CH$_2$Cl$_2$ was added 3-amino-N-cyclopropyl-4-methyl-benzamide 3A (8.5 g, 44.6 mmol, 1 eq). The mixture was stirred at RT for 3 hrs. The precipitate which was formed was filtered, washed with CH$_2$Cl$_2$, and reserved. The organic filtrate was washed with water and dried (Na$_2$SO$_4$), concentrated and combined with previously obtained solid to provide the thioisocyanate 3B as a white solid (7.45 g) which was used without further purification.

C. N-Cyclopropyl-4-methyl-3-thioureido-benzamide

A suspension of N-cyclopropyl-3-isothiocyanato-4-methyl-benzamide 3B (7.45 g) in a 7N solution of ammonia in methanol (40 mL) was stirred at room temperature for 1 hr. The mixture was concentrated, then redissolved in MeOH and reconcentrated to give the desired product as white solid (6.1 g, 60% for two steps).

D. N-Cyclopropyl-4-methyl-3-(4-phenyl-thiazol-2-ylamino)-benzamide

To a stirred solution of N-Cyclopropyl-4-methyl-3-thioureido-benzamide 3A (41 mg, 0.16 mmol) in 5 mL of ethanol was added 2-bromoacetophenone (33 mg, 0.16 mmol) and the reaction was heated at 75° C. overnight. After 16 hours, the reaction was cooled and concentrated and the crude product was purified by flash chromatography on silica gel loaded with CH$_2$Cl$_2$ and eluted with 2:1 hexanes/ethyl acetate followed by 1:2 hexanes/ethyl acetate to provide the title compound as a solid (32 mg, 94%). HPLC, t$_R$, 3.54 min.(6 minute method); MS, m/z 350.0 [M+1]$^+$.

The following analogues were prepared by the same method, using the appropriately subsbtituted bromoacetopheneone in step D:

3D-2. 3-[4-(4-Cyano-phenyl)-thiazol-2-ylamino]-N-cyclopropyl-4-methyl-benzamide.

HPLC, t$_R$, 2.38 min. (4 minute method); MS, m/z 375.0 [M+1]$^+$.

3D-3. N-Cyclopropyl-3-[4-(4-fluoro-phenyl)-thiazol-2-ylamino]-4-methyl-benzamide.

HPLC, t$_R$, 2.38 min. (4 minute method); MS, m/z 368.0 [M+1]$^+$.

3D-4. N-Cyclopropyl-3-[4-(4-methoxy-phenyl)-thiazol-2-ylamino]-4-methyl-benzamide.

HPLC, t$_R$, 2.68 min. (4 minute method); MS, m/z 380.1 [M+1]$^+$.

3D-5. N-Cyclopropyl-3-[4-(3-methoxy-phenyl)-thiazol-2-ylamino]-4-methyl-benzamide.

HPLC, t$_R$, 2.74 min. (4 minute method); MS, m/z 380.1 [M+1]$^+$.

3D-6. N-Cyclopropyl-3-[4-(2-methoxy-phenyl)-thiazol-2-ylamino]-4-methyl-benzamide.

HPLC, t$_R$, 2.50 min. (4 minute method); MS, m/z 380.1 [M+1]$^+$.

The following analogue was prepared by the same method, using 2-bromopropiophenone in step D:

3D-7. N-Cyclopronyl-4-methyl-3-(5-methyl-4-phenyl-thiazol-2-ylamino)-benzamide.

HPLC, t$_R$, 2.38 min. (4 minute method); MS, m/z 364.1 [M+1]$^+$.

EXAMPLE 4

Preparation of 2-(5-Cyclopropylcarbamoyl-2-methyl-phenylamino)-thiazole-4-carboxylic acid phenylamide

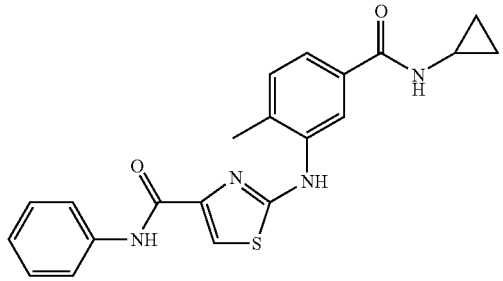

A. 2-(5-Cyclopropylcarbamoyl-2-methyl-phenylamino)-thiazole-4-carboxylic acid ethyl ester.

To a stirred solution of N-Cyclopropyl-4-methyl-3-thioureido-benzamide 3A (100 mg, 0.48 mmol) in 10 mL of ethanol was added ethyl bromopyruvate (89 mg, 0.48 mmol) and the reaction was heated at 75° C. overnight. After 16 hours, the reaction was cooled and concentrated and the crude product was purified by flash chromatography on silica gel loaded with $CH_2Cl_2$ and eluted with 1:1 hexanes/ethyl acetate followed by 1:2 hexanes/ethyl acetate to provide the title compound as a solid (75 mg, 45%). HPLC, $t_R$, 2.97 min. (4 minute method); MS, m/z 346.0 $[M+1]^+$.

B. (5-Cyclopropylcarbamoyl-2-methyl-phenylamino)-thiazole-4-carboxylic acid phenylamide.

To a stirred solution of ester 4A (60 mg, 0.17 mmol) in MeOH (5 mL) was added 10% NaOH (3 mL). The mixture was stirred at room temperature for 3 hrs, when the solution was acidified with conc. HCl to pH<3.0. The mixture was extracted with EtOAc, dried over $Na_2SO_4$, filtered and concentrated to give a white solid. The solid was dissolved in 10 mL of DMF and the solution was treated with EDCI (49 mg, 0.25 mmol), and HOBt (39 mg, 0.25 mmol). After stirring, for 15 min at room temperature, aniline (46 mL, 0.25 mmol) and DIPEA (0.18 mL, 1.03 mmol) were added and the reaction mixture was stirred at room temperature overnight. The reaction was quenched with water, extracted with $CH_2Cl_2$, dried over $Na_2SO_4$, filtered, and concentrated. The residue was purified by flash chromatography on silica gel eluted with 1:2 hexane/ethyl acetate to give the title compound as a white solid (42 mg, 62%). HPLC, $t_R$, 2.26 min. (4 minute method); MS, m/z 393.0 $[M+1]^+$.

EXAMPLE 5

Preparation of N-Isopropyl-4-methyl-3-(4-phenyl-thiazol-2-ylamino)-benzamide

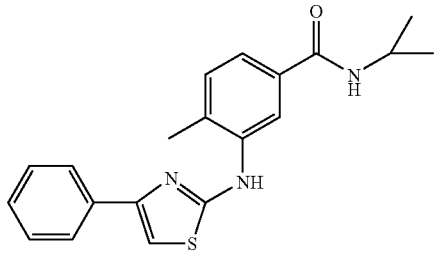

A. 3-Isothiocyanato-4-methyl-benzoic acid methyl ester.

To a solution of 1,1'-thiocarbonyldi-2(1H)-pyridone (5.72 g, 34.6 mmol) in 20 mL of $CH_2Cl_2$ was added ethyl 3-amino-4-methyl-benzoate (8.05 g, 34.6 mmol, 1 eq). The mixture was stirred at RT for 3 hrs. The precipitate was filtered off and washed with $CH_2Cl_2$. The organic filtrate was washed with water and dried ($Na_2SO_4$), concentrated and the crude product was purified by flash chromatography on silica gel loaded with $CH_2Cl_2$ and eluted with 9:1 hexanes/ethyl acetate to provide 5A as a white solid (5.16 g, 72%).

B. 4-Methyl-3-thioureido-benzoic acid methyl ester.

To a stirred solution of thioisocyanate 5A (5.16 g, 25 mmol) in $CH_2Cl_2$ was added a 7N solution of ammonia in methanol (10.6 mL, 75 mmol) was stirred at room temperature for 1 hr when additional ammonia in methanol solution was added. The mixture was concentrated, then redissolved in MeOH and reconcentrated to give the desired product 5B as white solid (5.5 g, 98%).

C. 4-Methyl-3-(4-phenyl-thiazol-2-ylamino)-benzoic acid methyl ester.

To a stirred solution of thiourea 5B (4.87 g, 21.7 mmol) in 5 mL of ethanol was added 2-bromoacetophenone (4.33 g, 21.7 mmol) and the reaction was heated at 75° C. overnight. After 16 hours, the reaction was cooled the precipitate filtered and reserved. The filtrate was concentrated and the crude product was purified by flash chromatography on silica gel loaded with $CH_2Cl_2$/methanol and eluted with 10:1 hexanes/ethyl acetate followed by 6:1 hexanes/ethyl acetate. The purified material was combined with the previously obtained precipitate to provide the title compound as a the hydrobromide salt (8.30 mg, 94%). MS, m/z 325.1 $[M+1]^+$.

D. 4-Methyl-3-(4-phenyl-thiazol-2-ylamino)-benzoic acid.

To a stirred solution of ester 5C (6.43 g, 19.8 mmol) in MeOH (50 mL) was added a solution of sodium hydroxide (10% in water, 40 mL) and the reaction was stirred at 65° C. for 3 hrs. The mixture was acidified to pH<3 with conc. HCl. The white precipitate was filtered and washed with water to give the desired product as a white solid (4.1 g, 67%). HPLC, $t_R$, 2.38 min. (4 minute method); MS, m/z 311.1 $[M+1]^+$.

E. N-Isopropyl-4-methyl-3-(4-phenyl-thiazol-2-ylamino)-benzamide.

To a mixture of acid 5D (100 mg, 0.32 mmol, 1 eq) in DMF was added EDCI (185 mg, 0.97 mmol, 3 eq), HOBt (148 mg, 0.97 mmol, 3 eq). The mixture was stirred for 15 at room temperature, when 2-propylamine (0.97 mmol, 3 eq) and DIPEA (1.93 mmol, 6 eq) were added and the mixture was stirred at room temperature overnight. The reaction was concentrated and water was added. The mixture was extracted with $CH_2Cl_2$, and the extract dried with $Na_2SO_4$, filtered and concentrated. The crude product was purified by flash chromatograph on silica gel loaded in $CH_2Cl_2$ and eluted with 3:1 hexanes/ethyl acetate to provide the title compound as a white foamy solid (106 mg, 94%). HPLC, $t_R$, 2.49 min. (4 minute method); MS, m/z 352.1 $[M+1]^+$.

The following analogues were prepared by the same method, using the appropriate amine in step E:

5E-2. N-Ethyl-4-methyl-3-(4-phenyl-thiazol-2-ylamino)-benzamide.

HPLC, $t_R$, 2.33 min. (4 minute method); MS, m/z 338.1 $[M+1]^+$.

5E-3. N-(2-Methoxy-ethyl)-4-methyl-3-(4-phenyl-thiazol-2-ylamino)-benzamide.

HPLC, $t_R$, 2.20 min. (4 minute method); MS, m/z 368.0 $[M+1]^+$.

5E-4. [4-Methyl-3-(4-phenyl-thiazol-2-ylamino)-phenyl]-morpholin-4-yl-methanone.

HPLC, $t_R$, 2.31 min. (4 minute method); MS, m/z 380.1 [M+1]$^+$.

5E-5. 4-Methyl-3-(4-phenyl-thiazol-2-ylamino)-1-thiazol-2-yl-benzamide.

HPLC, $t_R$, 1.62 min. (4 minute method); MS, m/z 393.0 [M+1]$^+$.

5E-6. 4-Methyl-3-(4-phenyl-thiazol-2-ylamino)-N-[1,2,4]triazol-4-yl-benzamide.

HPLC, $t_R$, 2.00 min. (4 minute method); MS, m/z 377.7 [M+1]$^+$.

5E-7. 4-Methyl-N-(5-methyl-[1,3,4]thiadiazol-2-yl)-3-(4-phenyl-thiazol-2-ylamino)-benzamide.

HPLC, $t_R$, 2.51 min. (4 minute method); MS, m/z 408.6 [M+1]$^+$.

EXAMPLE 6

Preparation of N-Cyclopropyl-4-methyl-3-(5-phenyl-oxazol-2-ylamino)-benzamide

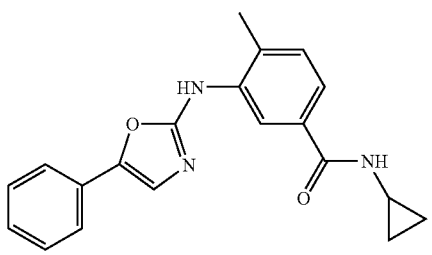

A. 2-Azido-1phenyl-ethanone.

To a stirred solution of 2-bromoacetophenone (5.37 g, 27 mmol) in acetone (50 mL) and water (18 mL) was added sodium azide (1.84 g, 28 mmol, 1.05 eq) and the mixture was stirred for 30 minutes. The mixture was diluted with water and extracted with CH$_2$Cl$_2$, dried over Na$_2$SO$_4$, filtered and concentrated. The crude product was purified by flash chromatography on silica gel eluted with 9:1 hexanes/ethyl acetate to provide the desired product as a yellow oil (3.23 g, 74%).

B. N-Cyclopropyl-4-methyl-3-(5-phenyl-oxazol-2-ylamino)-benzamide.

To a stirred solution of compound 6A (74 mg, 0.32 mmol) and 3B (58 mg, 0.36 mmol) in CH$_2$Cl$_2$ (10 mL) was added triphenylphosphine (94 mg, 0.36 mmol). The reaction mixture was stirred room temperature overnight, then concentrated. The crude product was purified by flash chromatography on silica gel loaded in CH$_2$Cl$_2$/MeOH and eluted with 1:1 hexane/ethyl acetate followed by 1:2 hexane/ethyl acetate to provide the title compound as an off-white solid (82 mg, 77%). (TTM2003.201.A105). HPLC, $t_R$, 3.19 min. (4 minute method); MS, m/z 334.0 [M+H]$^+$.

EXAMPLE 7

Preparation of N-Cyclopropyl-4-methyl-3-(5-phenyl-4H-[1,2,4]triazol-3-ylamino)-benzamide

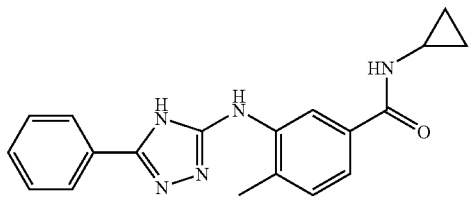

A. 3-(3-Benzoyl-thioureido)-N-cyclopropyl-4-methyl-benzamide.

The mixture of thioisocyanate 3B (500 mg, 2.63 mmol) and aniline 3A (429 mg, 2.63 mmol) was stirred at room temperature for 1 h. The mixture was concentrated to give the desired compound 7A which was used without further purification. HPLC, $t_R$, 2.78 min. (6 minute method); MS, m/z 334.0 [M+H]$^+$.

B. N-Cyclopropyl-4-methyl-3-(5-phenyl-4H-[1,2,4]triazol-3-ylamino)-benzamide.

To the stirred solution of compound 7A (150 mg, 0.42 mmol) in DMF was added hydrazine monohydrate (41 µL, 0.84 mmol) followed by the addition of triethylamine (0.24 mL, 1.68 mmol) and mercury(II) chloride (0.23 g, 0.84). The reaction mixture was stirred at room temperature for 3 hrs, then filtered through a pad of Celite which was washed with EtOAc. The organics were concentrated and the crude product was purified by flash chromatography on silica gel eluent with 2:1 CH$_2$Cl$_2$/EtOAc to give the title compound as a white solid (66 mg, 47%). HPLC, $t_R$, 2.78 min. (6 minute method); MS, m/z 334.0 [M+H]$^+$.

EXAMPLE 8

Preparation of N-Cyclopropyl-4-methyl-3-(5-phenyl-[1,2,4]oxadiazol-3-ylamino)-benzamide

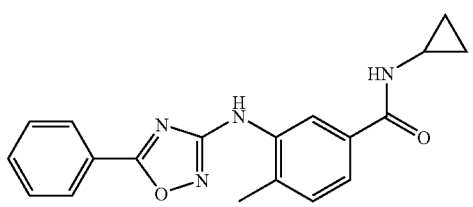

To the stirred solution of compound 7A (167 mg, 0.47 mmol) in DMF was added hydroxylamine (50% in H$_2$O, 62 µL, 0.94 mmol) followed by the addition triethylamine (0.26 mL, 1.88 mmol) and mercury(II) chloride (0.25 g, 0.94 mmol). After 3 hrs at room temperature, additional hydroxylamine (50% in H$_2$O, 62 µL, 0.94 mmol) and mercury(II) chloride (0.25 g, 0.94 mmol) were added and the reaction was stirred overnight. The mixture was filtered through a pad of Celite which was washed with EtOAc. The organics were concentrated and the crude product was purified by flash chromatography on silica gel eluent with 9:1 CH$_2$Cl$_2$/EtOAc to give the title compound as a white solid (83 mg, 52%). HPLC, $t_R$, 3.61 min. (6 minute method); MS, m/z 335.9 [M+H]$^+$.

EXAMPLE 9

N-Cyclopropyl-4-methyl-3-(5-phenyl-[1,3,4]thiadiazol-2-ylamino)-benzamide

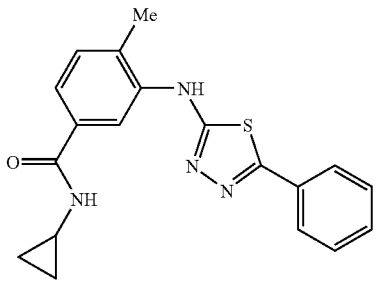

A. N-Cyclopropyl-4-methyl-3-([3-benzamido]-thioureido)-benzamide

Benzoylhydrazine (72 mg, 0.529 mmol) and the thioisocyanate 3B (123 mg, 0.529 mmol) were suspended in EtOH (3 ml) and stirred at 80° C. for 2.5 hr. After cooling down at room temperature, the resulting precipitate was filtered off and washed with ethanol to afford the desired compound 9A as a pure white solid (131 mg, 0.355 mmol, 67%). HPLC (4 minutes gradient) $t_R$ 1.90 min; MS m/z 368.94 [M+H]$^+$; $^1$H NMR (DMSO-$d_6$, 300 MHz) δ 0.57 (m, 2H), 0.67 (m, 2H), 2.23 (s, 3H), 2.84 (m, 1H), 7.28 (d, J=7.7, 1H), 7.66-7.48 (m, 5H), 7.96 (d, J=7.3, 2H), 8.42 (d, J=3.3, 1H), 9.65 (s, 1H), 9.70 (s, 1H), 10.56 (s, 1H) ppm.

B. N-Cyclopropyl-4-methyl-3-(5-phenyl-[1,3,4]thiadiazol-2-ylamino)-benzamide

To the compound 9A (106 mg, 0.2877 mmol) was added neat concentrated sulfuric acid (1.5 ml) and the resulting suspension was stirred at room temperature for 50 min. The mixture was slowly added into ice water (10 ml) and the resulting suspension was added into an aqueous ammonia solution. The resulting solid was filtered off and washed with water to afford a crude material (64 mg). Purification by flash chromatography (SiO$_2$, MeOH 1 to 2% in CH$_2$Cl$_2$) afforded the pure title compound as a white powder (32 mg, 0.091 mmol, 32%). HPLC (4 minutes gradient) $t_R$ 2.44 min; MS m/z 351.02 [M+H]$^+$; $^1$H NMR (DMSO-$d_6$, 300 MHz) δ 0.57 (m, 2H), 0.67 (m, 2H), 2.33 (s, 3H), 2.85 (m, 1H), 7.32 (d, J=7.89, 1H), 7.50-7.53 (m, 4H), 7.83 (m, 2H), 8.21 (s, 1H), 8.37 (d, J=3.5, 1H), 9.73 (br s, 1H) ppm.

EXAMPLE 10

N-Cyclopropyl-4-methyl-3-(3-phenyl-[1,2,4]thiadiazol-5-ylamino)-benzamide

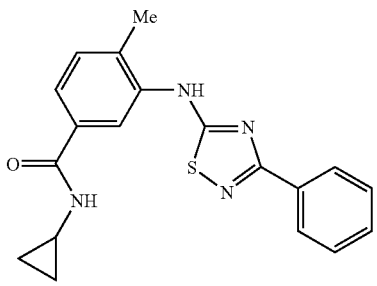

A. N-Hydroxy-benzamidine

Benzonitrile (1 ml, 9.79 mmol) was mixed with hydroxylamine hydrochloride (1.36 g, 1.96 mmol) and K$_2$CO$_3$ (2.71 g, 1.96 mmol) in anhydrous ethanol (15 ml). The solution was stirred at 80° C. for 16 hr. Water was added and the aqueous phase was extracted with EtOAc (3×), dried over MgSO$_4$ and the volatiles removed in vacuo to give a viscous oil (816 mg, 5.99 mmol, 62%). The compound 10A was used for next step without any further purification. HPLC (4 minutes gradient) $t_R$ 0.62 min; MS m/z 137.06 [M+H]$^+$.

B. N-Cyclopropyl-4-methyl-3-(3-phenyl-[1,2,4]thiadiazol-5-ylamino)-benzamide

Compound 10A (68 mg, 0.499 mmol) and thioisocyanate 3B (77 mg, 0.331 mmol) were dissolved in anhydrous DMF (1 ml). The mixture was heated under microwave irradiation at 200° C. for 10 min. Water was added and the resulting mixture was stirred at room temperature for 1 hr. The beige solid was filtered off and washed with water and hexanes to afford the title comopund (25 mg, 0.071 mmol, 14%). HPLC (4 minutes gradient) $t_R$ 2.76 min; MS m/z 351.01 [M+H]$^+$; $^1$H NMR (DMSO-$d_6$, 300 MHz) δ 0.59 (m, 2H), 0.68 (m, 2H), 2.36 (s, 3H), 2.88 (m, 1H), 7.36 (d, J=7.7, 1H), 7.49-7.65 (m, 4H), 8.15 (m, 2H), 8.39 (d, J=3.7, 1H), 8.58 (s, 1H), 10.31 (s, 1H) ppm.

EXAMPLE 11

2-(5-Cyclopropylcarbamoyl-2-methyl-phenylamino)-4-methyl-thiazole-5-carboxylic acid benzyl ester

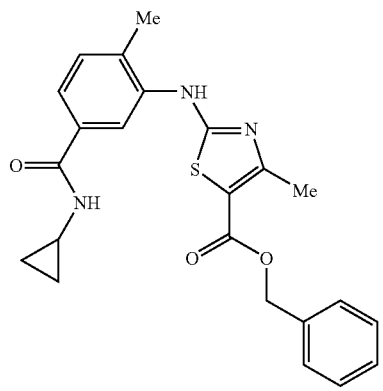

To a stirred solution of benzyl acetoacetate (555 mg, 2.887 mmol) in CHCl$_3$ (5 ml) was added dropwise bromine (147 μl, 2.869 mmol). After stirring at room temperature for 1 hr, the volatiles were removed in vacuo to afford an oily residue. This residue (200 mg, ca. 0.74 mmol) was mixed with thiourea 3C (184 mg, 0.738 mmol) in ethanol (1.5 ml) and the resulting solution was stirred at 80° C. for 3 hr. The solvent was removed in vacuo and the crude material was purified by flash chromatography (SiO$_2$, MeOH 1 to 5% in CH$_2$Cl$_2$). Subsequent recrystallization in ethanol afforded the title compound as a beige solid (59 mg, 0.140 mmol, 19%). HPLC (4 minutes gradient) $t_R$ 2.99 min; MS m/z 422.02 [M+H]$^+$; $^1$H NMR (DMSO-$d_6$, 300 MHz) δ 0.57 (m 2H), 0.67 (m, 2H), 2.26 (s, 3H), 2.83 (m, 1H), 5.22 (s, 2H), 7.35 (m, 6H), 7.60 (d, J=7.7, 1H), 8.03 (s, 1H), 8.39 (d, J=3.4, 1H), 10.06 (s, 1H) ppm.

EXAMPLE 12

2-(5-Cyclopropylcarbamoyl-2-methyl-phenylamino)-4-methyl-thiazole-5-carboxylic acid benzylamide

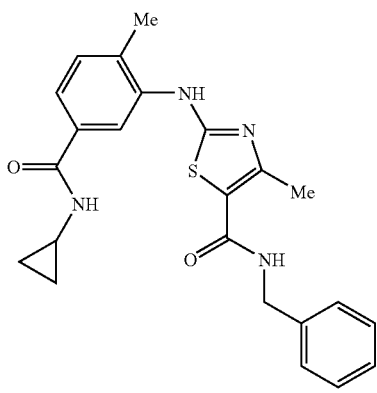

The title compound was prepared according to the procedure for Example 10 starting from acetoacetobenzylamide. Purification by flash chromatography (SiO$_2$, MeOH 1 to 10% in CH$_2$Cl$_2$) afforded a pale brown solid (46% yield). HPLC (4 minutes gradient) t$_R$ 1.97 min; MS m/z 421.06 [M+H]$^+$.

EXAMPLE 13

2-(5-Cyclopropylcarbamoyl-2-methyl-phenylamino)-thiazole-4-carboxylic acid ethyl ester

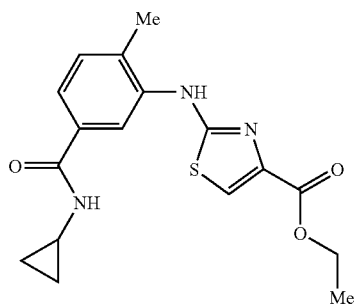

Thiourea 3C (124 mg, 0.497 mmol) and ethylbromopyruvate (69 µl, 0.550 mmol) were mixed in ethanol (1.5 ml) and heated at 80° C. for 45 min. After removal of the volatiles in vacuo the crude material was purified by flash chromatography (SiO$_2$, MeOH 1 to 4% in CH$_2$Cl$_2$) to afford a white powder (105 mg, 0.304 mmol, 61% yield). HPLC (4 minutes gradient) t$_R$ 2.25 min; MS m/z 345.97 [M+H]$^+$; $^1$H NMR (DMSO-d$_6$, 300 MHz) δ 0.55 (m, 2H), 0.67 (m, 2H), 1.28 (t, J=7.0, 3H), 2.28 (s, 3H), 2.83 (m, 1H), 4.24 (q, J=7.1, 2H), 7.31 (d, J=7.8, 1H), 7.51 (d, J=7.7, 1H), 7.70 (s, 1H), 8.14 (s, 1H), 8.34 (s, 1H), 9.64 (s, 1H) ppm.

EXAMPLE 14

5-Bromo-2-(5-cyolopropylcarbamoyl-2-methyl-phenylamino)-thiazole-4-carboxylic acid ethyl ester

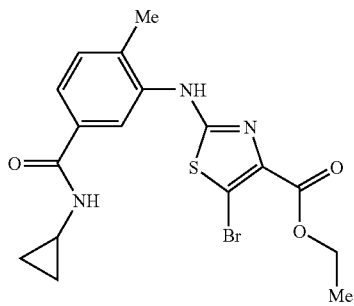

To a stirred suspension of compound 13 (23.6 mg, 0.0683 mmol) in CHCl$_3$ (0.5 ml) was added dropwise a solution of N-bromosuccinimide (13 mg, 0.0730 mmol) in CHCl$_3$ (0.5 ml). The mixture was stirred at room temperature for 30 min and the volatiles removed in vacuo. Trituration of the crude material in CH$_2$Cl$_2$/EtOAc provided an off white solid that was filtered off and dried (18 mg, 0.042 mmol, 62% yield). HPLC (4 minutes gradient) t$_R$ 2.65 min; MS m/z 423.90, 425.88 [M+H]$^+$; $^1$H NMR (DMSO-d$_6$, 300 MHz) δ 0.56 (m, 2H), 0.67 (m, 2H), 1.29 (t, J=7.1, 3H), 2.28 (s, 3H), 2.83 (m, 1H), 4.26 (q, J=7.0, 2H), 7.32 (d, J=7.9, 1H), 7.54 (d, J=7.4, 1H), 8.12 (s, 1H), 8.35 (d, J=3.6, 1H), 9.84 (s, 1H) ppm.

EXAMPLE 15

2-(5-Cyclopropylcarbamoyl-2-methyl-phenylamino)-4-(4-nitro-phenyl)-thiazole-5-carboxylic acid ethyl ester

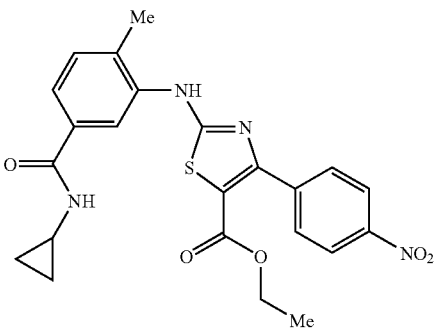

The title compound was prepared according to the procedure for Example 10 starting from ethyl 4-nitrobenzoyl acetate. After 30 min of heating the title compound precipitated out of the reaction mixture to give a pure yellow solid material (67% yield). HPLC (4 minutes gradient) t$_R$ 3.03 min; MS m/z 467.02 [M+H]$^+$; $^1$H NMR (DMSO-d$_6$, 300 MHz) δ 0.56 (m, 2H), 0.68 (m, 2H), 1.16 (t, J=7.0, 3H), 2.32 (s, 3H), 2.84 (m, 1H), 4.14 (q, J=6.7, 2H), 7.38 (d, J=7.9, 1H), 7.63 (d, J=7.7, 1H), 7.97 (d, J=8.5, 2H), 8.17 (s, 1H), 8.27 (d, J=8.4, 2H), 8.42 (d, J=3.3, 1H), 10.29 (s, 1H) ppm.

EXAMPLE 16

N-Cyclopropyl-4-methyl-3-[4-(4-nitro-phenyl)-thiazol-2-ylamino]-benzamide

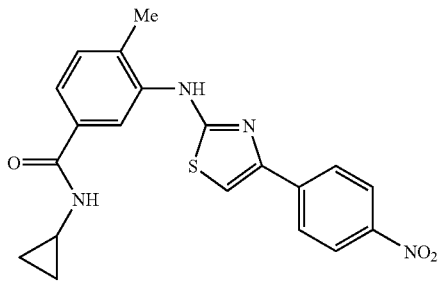

The title compound was prepared according to the procedure for Example 13 starting from α-bromo-4-nitroacetophenone. After 1.5 hr of heating the compound precipitated out of the reaction mixture to give a pure orange solid material (85% yield). HPLC (4 minutes gradient) $t_R$ 2.90 min; MS m/z 395.00 [M+H]$^+$; $^1$H NMR (DMSO-d$_6$, 300 MHz) δ 0.57 (m, 2H), 0.69 (m, 2H), 2.33 (s, 3H), 2.86 (m, 1H), 7.31 (d, J=7.8, 1H), 7.50 (d, J=7.7, 1H), 7.72 (s, 1H), 8.14 (d, J=8.7, 2H), 8.27 (d, J=8.7, 2H), 8.40 (d, J=3.6, 1H), 8.54 (s, 1H), 9.61 (s, 1H) ppm.

EXAMPLE 17

3-[5-Bromo-4-(4-nitro-phenyl)-thiazol-2-ylamino]-N-cyclopropyl-4-methyl-benzamide

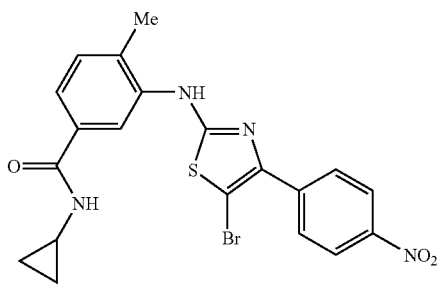

The title compound was prepared according to the procedure for Example 13. After one hour the compound precipitated out of the reaction mixture in a pure form as an orange solid (63% yield). HPLC (4 minutes gradient) $t_R$ 3.28 min; MS m/z 472.92, 474.88 [M+H]$^+$; $^1$H NMR (DMSO-d$_6$, 300 MHz) δ 0.57 (m, 2H), 0.60 (m, 2H), 2.32 (s, 3H), 2.85 (m, 1H), 7.32 (d, J=7.9, 1H), 7.51 (d, J=7.6, 1H), 8.19 (d, J=8.8, 2H), 8.32 (d, J=8.7, 2H), 8.39 (d, J=3.7, 1H), 8.43 (s, 1H), 9.78 (s, 1H) ppm.

EXAMPLE 18

2-(5-Cyclopropylcarbamoyl-2-methyl-phenylamino)-4-(4-morpholin-4-yl-phenyl)-thiazole-5-carboxylic acid benzylamide

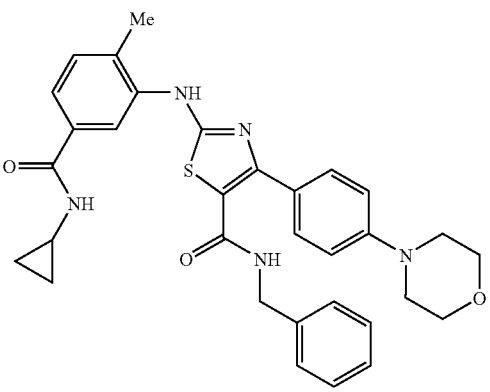

A. N-Benzyl-3-(4-morpholin-4-yl-phenyl)-3-oxo-propionamide

Under nitrogen atmosphere, LDA (1.8M solution in heptane/THF/ethylbenzene, 4.1 ml, 7.38 mmol) was added through syringe in anhydrous THF (10 ml). The mixture was cooled to −78° C. and a THF solution (5 ml) of 4-morpholinoacetophenone (1.01 g, 4.92 mmol) was added dropwise through syringe. The mixture was allowed to warm up to 0° C. for 30 min and then cooled down to −78° C. Benzylisocyanate (0.30 ml, 2.43 mmol) was added dropwise. The mixture was stirred at −78° C. for 25 min and allowed to warm up to room temperature overnight. The mixture was quenched by a saturated aqueous ammonium chloride solution and the compound was extracted with EtOAc (3×). The combined extracts were dried over MgSO$_4$ and the volatiles removed in vacuo. Addition of CH$_2$Cl$_2$ to the resulting oil induces formation of an insoluble solid. The compound was filtered off affording the intermediate 18A as a yellow solid (202 mg, 0.597 mmol, 25% yield). HPLC (4 minutes gradient) $t_R$ 2.30 min; MS m/z 339.07 [M+H]$^+$; $^1$H NMR (DMSO-d$_6$, 300 MHz) δ 3.32 (m, 4H), 3.74 (m, 4H), 3.85 (s, 2H), 4.30 (d, J=5.8, 2H), 6.99 (d, J=8.8, 2H), 7.24-7.35 (m, 5H), 7.86 (d, J=8.7, 2H), 8.60 (t, J=5.4, 1H) ppm.

B. 2-(5-Cyclopropylcarbamoyl-2-methyl-phenylamino)-4-(4-morpholin-4-yl-phenyl)-thiazole-5-carboxylic acid benzylamide To a stirred solution of intermediate 18A (90 mg, 0.266 mmol) in CHCl$_3$ (0.5 ml) was added dropwise bromine (42.4 mg, 0.264 mmol) as a solution in CHCl$_3$ (0.5 ml). The mixture was stirred at room temperature for 25 min and the volatiles removed in vacuo to afford a yellowish solid (112 mg, 0.140 mmol, 85% crude). This solid (111 mg, 0.223 mmol) was mixed with thiourea 3C (56 mg, 0.225 mmol) in ethanol (1.5 ml) and the resulting mixture stirred at 80° C. for 30 min. The volatiles were removed in vacuo and the residue dissolved in CH$_2$Cl$_2$ containing a little amount of methanol. The organic phase was washed with saturated NaHCO$_3$, dried over MgSO$_4$ and the volatiles removed in vacuo. Upon addition of EtOAc, the expected compound precipitated in a very pure form and was isolated by filtration to give the title compound as an off white solid (63 mg, 0.222 mmol, 50% yield). HPLC (4 minutes gradient) $t_R$ 2.60 min; MS m/z 568.15 [M+H]$^+$; $^1$H NMR (DMSO-d$_6$, 300 MHz) δ 0.56 (m, 2H), 0.68 (m, 2H), 2.31 (s, 3H), 2.84 (m, 1H), 3.15 (br s, 4H), 3.75 (br s, 4H), 4.32 (d, J=5.6, 2H), 6.87 (d, J=8.6, 2H), 7.23-7.35 (m, 6H), 7.53 (m, 3H), 8.21 (br t, 1H), 8.33 (s, 1H), 8.38 (d, J=3.8, 1H), 9.67 (s, 1H) ppm.

EXAMPLE 19

2-(5-Cyclopropylcarbamoyl-2-methyl-phenylamino)-thiazole-5-carboxylic acid methyl ester

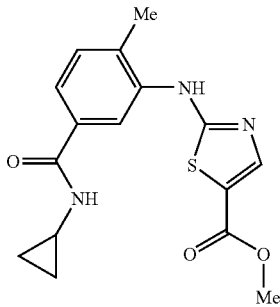

The compound was prepared according to a literature procedure (*Tet. Lett.*, 42 (2001) 2101-2102). Methyl trans 3-methoxyacrylate (0.12 ml, 1.116 mmol) was dissolved in a mixture of water (1 ml) and 1,4-dioxane (1 ml) and cooled down to −15° C. N-bromosuccinimide (145 mg, 1.23 mmol) was added and the solution allowed to warm to room temperature under stirring for 3 hours. The thiourea 3C (306 mg, 1.23 mmol) was added and the mixture stirred at 80° C. for 30 min. Concentrated aqueous NH$_4$OH was added and the compound extracted with CH$_2$Cl$_2$ (2×). The combined extracts were dried over MgSO$_4$ and the solvent removed in vacuo to afford a crude material. Purification by flash chromatography (SiO$_2$, MeOH 1 to 4% in CH$_2$Cl$_2$) provided the expected compound as an off white solid (223 mg, 0.673 mmol, 61%). HPLC (4 minutes gradient) t$_R$ 2.11 min; MS m/z 331.95 [M+H]$^+$; $^1$H NMR (DMSO-d$_6$, 300 MHz) δ 0.57 (m, 2H), 0.67 (m, 2H), 2.28 (s, 3H), 2.82 (m, 1H), 3.75 (s, 3H), 7.34 (d, J=7.9, 1H), 7.57 (d, J=7.6, 1H), 7.90 (s, 1H), 8.13 (s, 1H), 8.40 (d, J=3.6, 1H), 10.10 (br s, 1H) ppm.

EXAMPLE 20

2-(5-Cyclopropylcarbamoyl-2-methyl-phenylamino)-thiazole-5-carboxylic acid

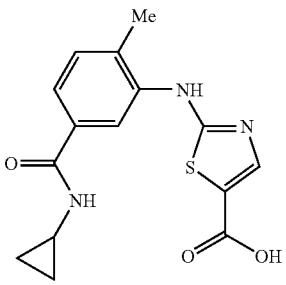

Compound 19 (99 mg, 0.299 mmol) was suspended in a mixture of methanol (0.5 ml), THF (0.5 ml) and water (0.5 ml) and stirred at 60° C. for 13 hr (90% conversion by HPLC). The reaction was completed by heating at 80° C. for 3 hr. The solvents were removed in vacuo and water was added to dissolve the residue. The title compound was precipitated in a pure form by addition of a concentrated solution of HCl. Filtration and drying provided a brown solid (58 mg, 61%) HPLC (4 minutes gradient) t$_R$ 1.63 min; MS m/z 318.0 [M+H]$^+$; $^1$H NMR (DMSO-d$_6$, 300 MHz) δ 0.56 (m, 2H), 0.67 (m, 2H), 2.28 (s, 3H), 2.84 (m, 1H), 7.33 (d, J=7.9, 1H), 7.56 (d, J=7.6, 1H), 7.80 (s, 1H), 8.14 (s, 1H), 8.40 (d, J=3.7, 1H), 10.02 (br s, 1H) ppm.

EXAMPLE 21

2-(5-Cyclopropylcarbamoyl-2-methyl-phenylamino)-4-phenyl-thiazole-5-carboxylic acid cyclopropylmethyl-amide

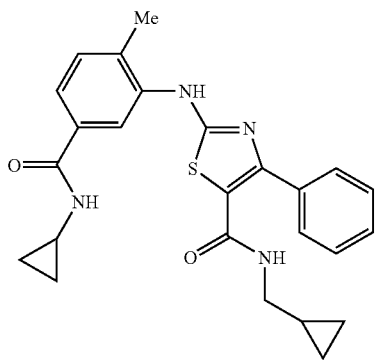

A. N-Cyclopropylmethyl-3-oxo-3-phenyl-propionamide

Ethyl benzoylacetate (621 mg, 3.23 mmol) and cyclopropylmethylamine (0.34 ml, 3.92 mmol) were dissolved in 1,4-dioxane (1 ml). Para-toluenesulfonic acid (3 crystals, catalytic) was added and the mixture heated under microwave irradiation at 150° C. for 30 min. The crude mixture was poured onto a SiO$_2$ column and purified by flash chromatography (eluted with EtOAc 10 to 35% in hexanes). The title compound was isolated as a yellow solid (309 mg, 44%). HPLC (4 minutes gradient) t$_R$ 2.04 min; MS m/z 218.0 [M+H]$^+$.

B. 2-(5-Cyclopropylcarbamoyl-2-methyl-phenylamino)-4-phenyl-thiazole-5-carboxylic acid cyclopropylmethyl-amide The title compound was prepared according to the procedure for Example 10 starting from intermediate 21A. Purification by flash chromatography (SiO$_2$, MeOH 1 to 3% in CH$_2$Cl$_2$) afforded a pale brown solid (33% yield). HPLC (4 minutes gradient) t$_R$ 2.62 min; MS m/z 446.57 [M+H]$^+$; $^1$H NMR (DMSO-d$_6$, 300 MHz) δ 0.12 (m, 2H), 0.38 (m, 2H), 0.56 (m, 2H), 0.68 (m, 2H), 0.91 (m, 1H), 2.32 (s, 3H), 2.84 (m, 1H), 2.99 (t, J=6.2, 2H), 7.32 (d, J=7.8, 1H), 7.39 (m, 3H), 7.52 (d, J=7.7, 1H), 7.70 (d, J=6.2, 2H), 7.85 (br t, 1H), 8.35 (s, 1H), 8.40 (d, J=3.7, 1H), 9.71 (s, 1H) ppm.

EXAMPLE 22

4-{3-[2-(5-Cyclopropylcarbamoyl-2-methyl-phenylamino)-5-methoxycarbonylthiazol-4-yl]-phenyl}-piperidine-1-carboxylic acid methyl ester

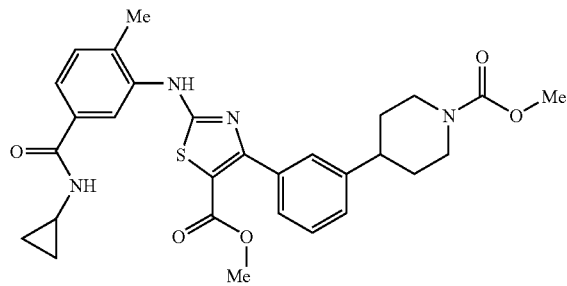

A. 4-(3-Methoxycarbonyl-phenyl)-piperidine-1-carboxylic acid methyl ester

To a stirred solution of 4-(3-methoxycarbonylphenyl) piperidine hydrochloride (871 mg, 3.406 mmol) in anhydrous $CH_2Cl_2$ (10 ml) was added triethylamine (1.04 ml, 7.48 mmol). The mixture was cooled down to 0° C. and methylchloroformate (0.32 ml, 4.141 mmol) was added dropwise through syringe. The mixture was allowed to warm to room temperature over 3 hr. After adding a 0.2 N HCl solution, the compound was extracted with $CH_2Cl_2$, the organic phase dried over $MgSO_4$ and the solvent removed by evaporation. Purification by flash chromatography ($SiO_2$, EtOAc 20 to 30% in hexanes), afforded the title compound 21A as a colorless viscous oil (874 mg, 3.151 mmol, 93%). HPLC (4 minutes gradient) $t_R$ 2.83 min; MS m/z 278.0 [M+H]$^+$; $^1$H NMR (DMSO-$d_6$, 300 MHz) δ 1.52 (qd, J=4.0, J=12.5, 2H), 1.77 (d, J=12.3, 2H), 2.82 (m, 3H), 3.61 (s, 3H), 3.85 (s, 3H), 4.11 (m, 2H), 7.46 (t, J=7.5, 1H), 7.56 (d, J=7.6, 1H), 7.81 (m, 2H) ppm.

B. 4-[3-(2-Methoxycarbonyl-acetyl)-phenyl]-piperidine-1-carboxylic acid methyl ester A LDA solution (1.8M in heptane/THF/ethylbenzene, 3.7 ml, 6.66 mmol) and THF (10 ml) were mixed in a dry flask under nitrogen atmosphere and cooled down to −78° C. Anhydrous methyl acetate (0.24 ml, 3.026 mmol) was added dropwise through syringe and the mixture stirred at −78° C. for 40 min. A solution of ester 21A (836 mg, 3.014 mmol) in THF (5 ml) was added dropwise and the mixture allowed to warm to room temperature over 3 hr. The reaction was quenched with saturated ammonium chloride, the compound was extracted with EtOAc (2×) and the combined extracts dried over $MgSO_4$. After removal of the solvents and purification by flash chromatography ($SiO_2$, EtOAc 10 to 35% in hexanes), the title compound 21B was isolated as a viscous yellow oil (255 mg, 0.798 mmol, 27%). HPLC (4 minutes gradient) $t_R$ 2.59 min; MS m/z 319.92 [M+H]$^+$; $^1$H NMR (DMSO-$d_6$, 300 MHz) δ 1.52 (qd, J=4.0, J=12.5, 2H), 1.77 (d, J=12.1, 2H), 2.79 (m, 3H), 3.61 (s, 3H), 3.65 (s, 3H), 4.11 (m, 2H), 4.23 (s, 2H), 7.48 (t, J=7.6, 1H), 7.57 (d, J=7.5, 1H), 7.81 (m, 2H) ppm.

C. 4-{3-[2-(5-Cyclopropylcarbamoyl-2-methyl-phenylamino)-5-methoxycarbonylthiazol-4-yl]-phenyl}-piperidine-1-carboxylic acid methyl ester The title compound was prepared according to the procedure for Example 10 starting from intermediate 22B. Purification by flash chromatography ($SiO_2$, MeOH 1 to 3% in $CH_2Cl_2$) provided an off white solid (58%). HPLC (4 minutes gradient) $t_R$ 2.85 min; MS m/z 549.14 [M+H]$^+$; $^1$H NMR (DMSO-$d_6$, 300 MHz) δ 0.56 (m, 2H), 0.68 (m, 2H), 1.54 (qd, J=3.5, J=12.2, 2H), 1.80 (d, J=12.2, 2H), 2.32 (s, 3H), 2.86 (m, 4H), 3.61 (s, 3H), 3.65 (s, 3H), 4.11 (m, 2H), 7.31-7.37 (m, 3H), 7.55-7.63 (m, 3H), 8.25 (s, 1H), 8.41 (d, J=3.8, 1H), 10.16 (s, 1H) ppm.

EXAMPLE 23

4-{3-[2-(5-Cyclopropylcarbamoyl-2-methyl-phenylamino)-5-(cyclopropylmethyl-carbamoyl)-thiazol-4-yl]-phenyl}-piperidine-1-carboxylic acid methyl ester

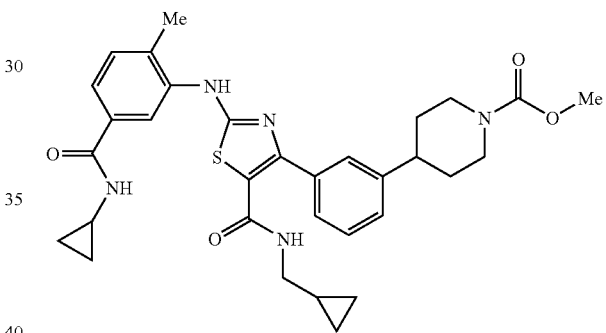

A. 4-{3-[2-(Cyclopropylmethyl-carbamoyl)-acetyl]-phenyl}-piperidine-1-carboxylic acid methyl ester The title compound was prepared according to the procedure used for Example 20 starting from intermediate 22B. Purification by flash chromatography ($SiO_2$, EtOAc 20 to 60% in hexanes) afforded a foamy solid (36% yield). HPLC (4 minutes gradient) $t_R$ 2.38 min; MS m/z 359.10 [M+H]$^+$.

B. 4-{3-[2-(5-Cyclopropylcarbamoyl-2-methyl-phenylamino)-5-(cyclopropylmethyl-carbamoyl)-thiazol-4-yl]-phenyl}-piperidine-1-carboxylic acid methyl ester The title compound was prepared according to the procedure used for Example 10 starting from intermediated 22A. Purification by flash chromatography ($SiO_2$, MeOH 1 to 4% in $CH_2Cl_2$) provided an off white solid (41% yield). HPLC (4 minutes gradient) $t_R$ 2.74 min; MS m/z 588.09 [M+H]$^+$; $^1$H NMR (DMSO-$d_6$, 300 MHz) δ 0.13 (m, 2H), 0.37 (m, 2H), 0.56 (m, 2H), 0.68 (m, 2H), 0.80 (m, 1H), 1.53 (qd, J=3.2, J=12.0, 2H), 1.80 (d, J=11.9, 2H), 2.32 (s, 3H), 2.85 (m, 4H), 2.99 (t, J=6.0, 2H), 3.60 (s, 3H), 4.10 (m, 2H), 7.25-7.36 (m, 3H), 7.51-7.60 (m, 3H), 7.89 (br t, 1H), 8.40 (s, 2H), 9.70 (s, 1H) ppm.

EXAMPLE 24

4-{3-[2-(5-cyclopropylcarbamoyl-2-methyl-phenylamino)-5-[1,3,4]oxadiazol-2-yl-thiazol-4-yl]-phenyl}-piperidinium trifluoroacetate

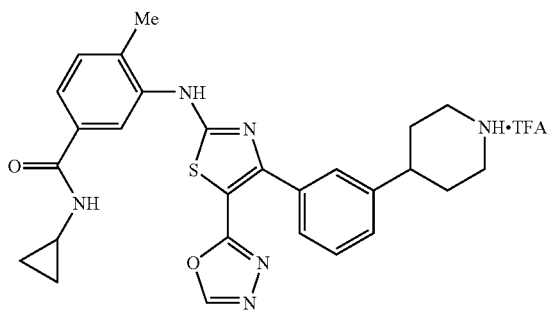

A. 4-{3-[2-(5-Cyclopronylcarbamoyl-2-methyl-phenylamino)-5-[1,3,4]oxadiazol-2-yl-thiazol-4-yl]-phenyl}-piperidine-1-carboxylic acid methyl ester Compound 22C (98 mg, 0.179 mmol) was dissolved in methanol (1 ml), hydrazine hydrate (1 ml) and DMF (4 drops). The mixture was stirred at room temperature for 8 hr. The volatiles were removed in vacuo. The resulting yellow solid was suspended in trimethyl orthoformate (2 ml) and heated under microwave irradiation to 120° C. for 30 min. After removal of the volatiles, the residue was dissolved in a mixture of 1,4-dioxane (2 ml) and acetic acid (0.1 ml) and heated using microwave irradiation at 160° C. for 30 min. After removal of the volatiles in vacuo, the title compound 24A was purified by flash chromatography (SiO$_2$ MeOH 1 to 4% in CH$_2$Cl$_2$) to afford a beige solid (83 mg, 0.149 mmol, 83% yield). HPLC (4 minutes gradient) t$_R$ 2.58 min; MS m/z 559.12 [M+H]$^+$; $^1$H NMR (DMSO-d$_6$, 300 MHz) δ 0.57 (m, 2H), 0.68 (m, 2H), 1.53 (qd, J=3.4, J=12.3, 2H), 1.80 (d, J=12.2, 2H), 2.34 (s, 3H), 2.84 (m, 4H), 3.60 (s, 3H), 4.09 (m, 2H), 7.37 (m, 3H), 7.56 (m, 3H), 8.37 (s, 1H), 8.41 (d, J=3.7, 1H), 9.13 (s, 1H), 10.14 (s, 1H) ppm.

B. 4-{3-[2-(5-cyclopropylcarbamoyl-2-methyl-phenylamino)-5-[1,3,4]oxadiazol-2-yl-thiazol-4-yl]-phenyl}-piperidinium trifluoroacetate Under nitrogen atmosphere, compound 24A (57 mg, 0.102 mmol) was dissolved in a 33% HBr solution in AcOH (0.5 ml) and stirred at room temperature for 6 hr. The reaction was quenched at 0° C. with saturated NaHCO$_3$ and the resulting solid extracted by CH$_2$Cl$_2$ (3×). The organic extracts were dried over MgSO$_4$ and the volatiles removed in vacuo to give a crude material. Purification by preparative HPLC afforded the title compound TFA salt as a glassy solid (3.8 mg, 0.0062 mmol, 6% yield). HPLC (4 minutes gradient) t$_R$ 1.86 min; MS m/z 501.24 [M+H]$^+$.

EXAMPLE 25

N-Cyclopropyl-4-methyl-3-[4-(4-nitro-phenyl)-5-[1,3,4]oxadiazol-2-yl-thiazol-2-ylamino]-benzamide

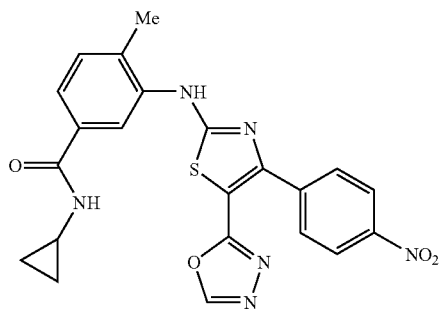

The title compound was prepared according to the procedure for Example 24A starting from compound 15. Purification by flash chromatography (SiO2, MeOH 1 to 2% in CH$_2$Cl$_2$) afforded the title compound as a yellow solid (15% yield). HPLC (4 minutes gradient) t$_R$ 2.57 min; MS m/z 463.0 [M+H]$^+$; $^1$H NMR (DMSO-d$_6$, 300 MHz) δ 0.57 (m, 2H), 0.69 (m, 2H), 2.27 (s, 3H), 2.84 (m, 1H), 7.37 (d, J=7.9, 1H), 7.60 (d, J=8.1, 1H), 8.02 (d, J=8.6, 2H), 8.29 (m, 3H), 8.42 (d, J=3.7, 1H), 9.17 (s, 1H) ppm.

EXAMPLE 26

2-(5-Cyclopropylcarbamoyl-2-methyl-phenylamino)-thiazole-5-carboxylic acid benzylamide

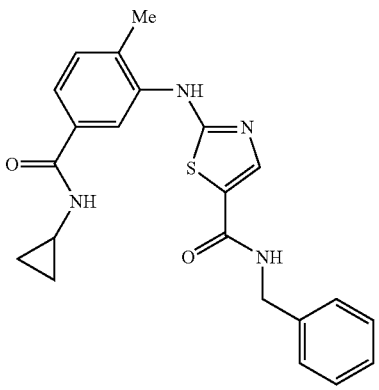

Compound 20 (45 mg, 0.142 mmol) and benzylamine (16 µl, 0.146 mmol) were dissolved in anhydrous DMF (1 ml). To the stirred solution were added HOBt.H$_2$O (26 mg, 0.170 mmol) and EDCI (33 mg, 0.172 mmol) and the mixture stirred at room temperature for 1.5 hr. The mixture was poured onto a SiO$_2$ column and the compound eluted with 1 to 6% MeOH in CH$_2$Cl$_2$. The combined CH$_2$Cl$_2$ phases were washed with water and dried over MgSO$_4$. Evaporation of the solvents afforded the title compound as an off white solid (19 mg, 0.047 mmol, 33% yield). HPLC (4 minutes gradient) $t_R$ 2.28 min; MS m/z 407.10 [M+H]$^+$; $^1$H NMR (DMSO-d$_6$, 300 MHz) δ 0.56 (m, 2H), 0.67 (m, 2H), 2.28 (s, 3H), 2.83 (m, 1H), 4.40 (d, J=5.6, 2H), 7.25-7.37 (m, 6H), 7.5.3 (d, J=7.7, 1H), 7.86 (s, 1H), 8.18 (s, 1H), 8.38 (d, J=3.4, 1H), 8.84 (br t, 1H), 9.76 (s, 1H) ppm.

EXAMPLE 27

Preparation of 4-Bromo-2-(5-cyclopropylcarbamoyl-2-methyl-phenylamino)-thiazole 5-carboxylic acid benzylamide

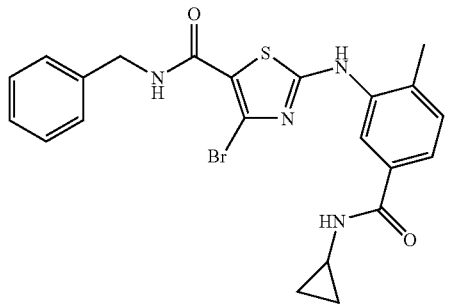

A. 2,4-Dibromo-thiazole

A stirred solution of 2,4-thiazolidinedione (5 g, 42.7 mmol) in phosphorus oxybromide (25 g, 87.2 mmol) was heated to 110° C. for 3 hours. After cooling to room temperature, 250 g of crushed ice was added (CAUTION). The precipitate that is formed was filtered and dissolved in a mixture of acetone/methylene chloride/MeOH. The remaining aqueous phase was extracted with ether and methylene chloride. The combined organic phases were dried over MgSO$_4$ and the volatiles removed in vacuo. The crude product was purified by column chromatography on silica gel (EtOAc 20% to 100% in hexanes) to provide 2,4-dibromo-thiazole 26A as a yellow solid (5.36 g, 55% yield).

B. 2,4-Dibromo-thiazole-5-carboxylic acid benzylamide

To a stirred solution of 2,4-dibromo-thiazole (4.95 g, 20.4 mmol) in THF at −78° C. was added LDA (1.8M in THF/hexanes, 13.6 ml, 24.5 mmol) slowly. The reaction was then stirred at −78° C. for 30 min., when benzylisocyanate (3.8 ml, 30.6 mmol) was added slowly. The mixture was then stirred at −78° C. for 30 min. before it was slowly warmed up to RT. Water was then added carefully to quench the reaction. The mixture was extracted with EtOAc and the combined extracts were dried over sodium sulfate and concentrated. The crude product was purified by column chromatography on silica gel (10% EtOAc/hexanes) to give 2,4-dibromo-thiazole-5-carboxylic acid benzylamide 26B as a white solid (5.05 g, 13.43 mmol, 66%).

C. 4-Bromo-2-(5-cyclopropylcarbamoyl-2-methyl-phenylamino)-thiazole-5-carboxylic acid benzylamide To a mixture of 2,4-dibromo-thiazole-5-carboxylic acid benzylamide 27B (3.86 g, 10.3 mmol), and 3-amino-N-cyclopropyl-4-methyl-benzamide 3A (7.81 g, 41.1 mmol) in DMSO (10 ml, anhydrous grade) was added diisopropylethylamine (1.79 ml, 10.3 mmol) and the solution was deoxygenated and then heated at 110° C. under nitrogen for 20 hours. The mixture was cooled to RT, dissolved in methylene chloride, and washed with water. The aqueous layer was extracted twice with methylene chloride, and the combined organics were dried over sodium sulfate and concentrated. The crude product was triturated with EtOAc and filtered to give the title compound 21C as an off-white solid (2.93 g, 6.04 mmol, 59%).

EXAMPLE 28

2-(5-Cyclopropylcarbamoyl-2-methyl-phenylamino)-4-(4-fluoro-3-methyl-phenyl)-thiazole-5-carboxylic acid benzylamide

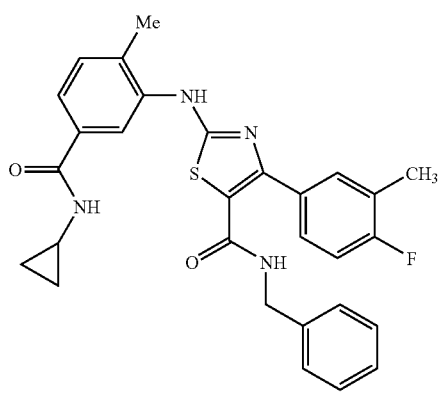

A microwave reaction flask was charged with 4-bromo-2-(5-cyclopropylcarbamoyl-2-methyl-phenylamino)-thiazole-5-carboxylic acid benzylamide (10 mg, 0.02 mmol, 1.0 eq), 3-methyl-4-fluorophenylboronic acid (32 mg, 0.21 mmol, 10 eq), tetrakistriphenylphosphine palladium (5 mg, 0.004 mmol, 0.2 eq), 200 μL of dioxane, and 200 μL of saturated aqueous K$_2$CO$_3$. The mixture was heated with stirring in the microwave at 120° C. for 10 minutes. The layers were separated and dioxane layer was concentrated and purified by preparative HPLC. Fractions containing product were concentrated to provide the title compound as a white solid (7.5 mg, 71%). HPLC (4 minutes gradient) $t_R$ 2.61 min; MS m/z 515.24 [M+H]$^+$; $^1$H NMR (DMSO-d$_6$, 500 MHz) δ 0.53 (m, 2H), 0.66 (m, 2H), 2.16 (s, 3H), 2.29 (s, 3H), 2.82 (m, 1H), 4.29 (d, J=4.3, 2H), 7.05 (t, J=8.9, 1H), 7.20-7.30 (m, 6H), 7.44-7.51 (m, 3H), 8.30-8.36 (m, 3H), 9.72 (s, 1H) ppm.

Additional analogues were prepared by this method using the appropriately substituted boronic acid and analyzed by HPLC and MS.

TABLE 1

| Example | Structure | Name | MW | m/z | T$_r$ |
|---|---|---|---|---|---|
| 28-2 | 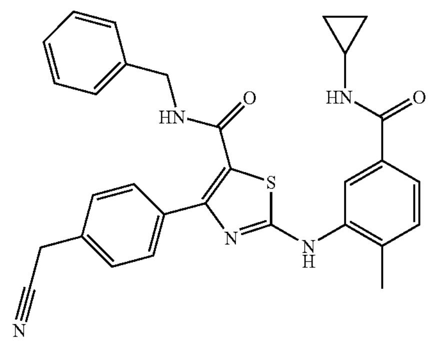 | 4-(4-Cyanomethyl-phenyl)-2-(5-cyclo-propylcarbamoyl-2-methylphenylamino)-thiazole-5-carboxylic acid benzylamide | 521.643 | 522.1 | 2.72 |
| 28-3 | 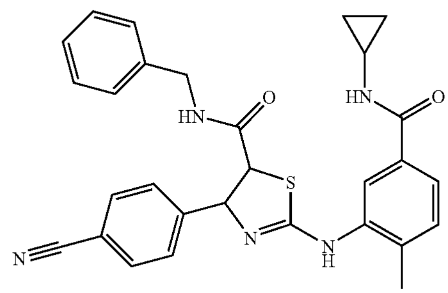 | 4-(4-Gyano-phenyl)-2-(5-cyclopropyl-carbamoyl-2-methyl-phenylamino)-4,5-dihydro-thiazole-5-carboxylic acid benzylamide | 509.632 | 508.06 | 2.75 |
| 28-4 | 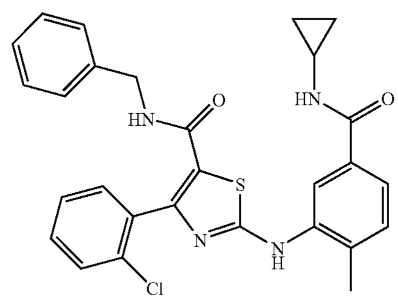 | 4-(2-Chloro-phenyl)-2-(5-cyclopropyl-carbamoyl-2-methyl-phenylamino)-thiazole-5-carboxylic acid benzylamide | 517.051 | 517.06 | 2.91 |
| 28-5 | 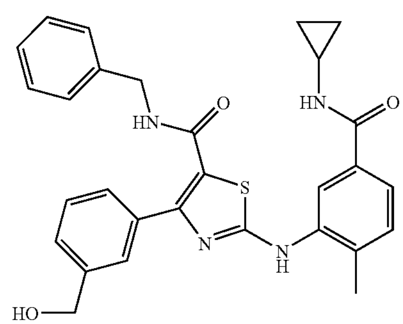 | 2-(5-Cyclopropyl-carbamoyl-2-methyl-phenylamino)-4-(3-hydroxymethylphen-yl)-thiazole-5-carbox-ylic acid benzylamide | 512.632 | 512.99 | 2.39 |
| 28-6 | 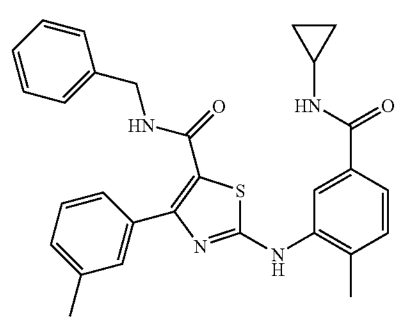 | 2-(5-Cyclopropylcar-bamoyl-2-methyl-phenylamino)-4-m-tolyl-thiazole-5-carboxylic acid benzylamide | 496.633 | 497.14 | 2.97 |

TABLE 1-continued

| Example | Structure | Name | MW | m/z | T$_r$ |
|---|---|---|---|---|---|
| 28-7 | 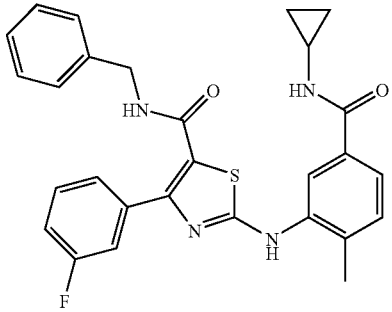 | 2-(5-Cyclopropylcarbamoyl-2-methylphenylamino)-4-(3-fluorophenyl)thiazole-5-carboxylic acid benzylamide | 500.596 | 501.08 | 2.87 |
| 28-8 | 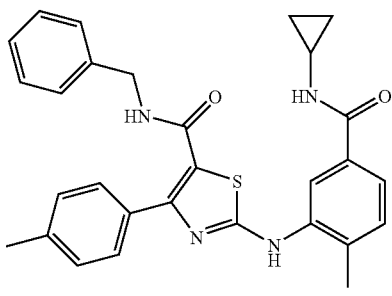 | 2-(5-Cyclopropylcarbamoyl-2-methylphenylamino)-4-p-tolylthiazole-5-carboxylic acid benzylamide | 496.633 | 497.1 | 2.95 |
| 28-9 | 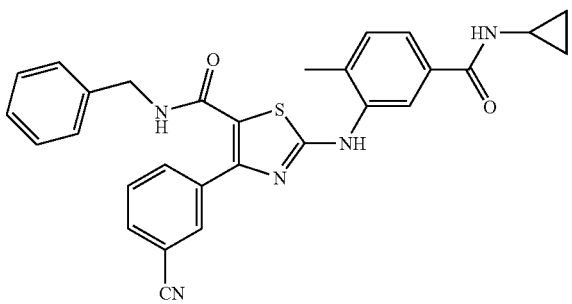 | 4-(3-Cyano-phenyl)-2-(5-cyclopropylcarbamoyl-2-methylphenylamino)thiazole-5-carboxylic acid benzylamide | 507.616 | 508.05 | 2.74 |
| 28-10 | 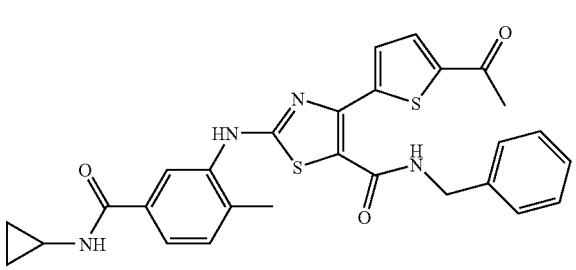 | 4-(5-Acetyl-thiophen-2-yl)-2-(5-cyclopropylcarbamoyl-2-methylphenylamino)-thiazole-5-carboxylic acid benzylamide | 530.669 | 530.99 | 2.77 |
| 28-11 | 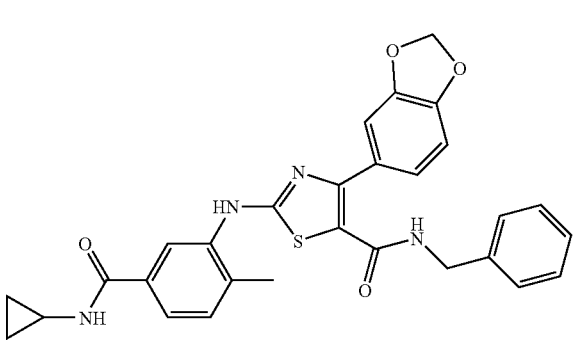 | 4-Benzo[1,3]dioxol-5-yl-2-(5-cyclopropylcarbamoyl-2-methylphenylamino)-thiazale-5-carboxylic acid benzylamide | 526.615 | 527.1 | 2.75 |

TABLE 1-continued

| Example | Name | MW | m/z | T$_r$ |
|---|---|---|---|---|
| 28-12 | 4-(5-Cyano-thiophen-2-yl)-2-(5-cyclopropylcarbamoyl-2-methylphenylamino)-thiazole-5-carboxylic acid benzylamide | 513.642 | 513.95 | 2.98 |
| 28-13 | 2-(5-Cyclopropylcarbamoyl-2-methyl-phenylamino)-4-(4-methoxy-phenyl)-thiazole-5-carboxylic acid benzylamide | 512.632 | 513.14 | 2.76 |
| 28-14 | 4-[5-Benzylcarbamoyl-2-(5-cyclopropyl-carbamoyl-2-methyl-phenylamino)thiazol-4-yl]benzoic acid ethyl ester | 554.669 | 555.13 | 2.97 |
| 28-15 | 3-[5-Benzylcarbamoyl-2-(5-cyclopropyl-carbamoyl-2-methyl-phenylamino)thiazol-4-yl]-benzoic acid methyl ester | 540.642 | 541.06 | 2.76 |
| 28-16 | 2-(5-Cyclopropyl-carbamoyl-2-methyl-phenylamino)-4-(4-fluoro-phenyl)-thiazole-5-carboxylic acid benzylamide | 500.596 | 501.1 | 2.87 |

TABLE 1-continued

| Example | Structure | Name | MW | m/z | T$_r$ |
|---|---|---|---|---|---|
| 28-17 | 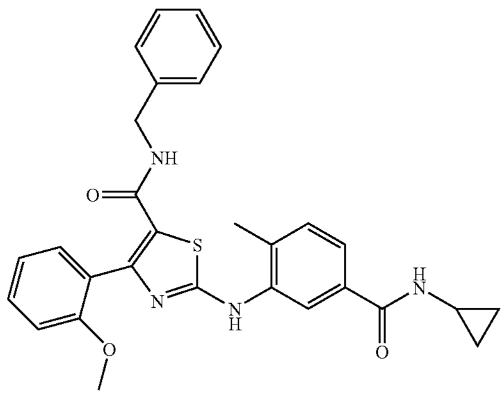 | 2-(5-Cyclopropyl-carbamoyl-2-methyl-phenylamino)-4-(2-methoxy-phenyl)-thiazole-5-carboxylic acid benzylamide | 512.632 | 512.12 | 2.69 |
| 28-18 | 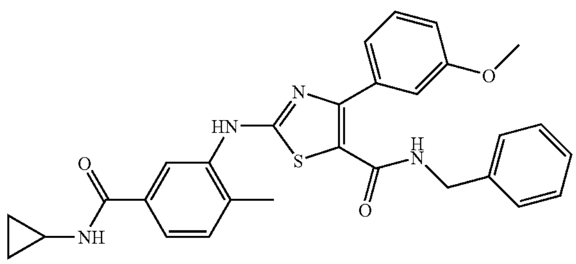 | 2-(5-Cyclopropylcar-bamoyl-2-methyl-phenylamino)-4-(3-methoxy-phenyl)-thiazole-5-carboxylic acid benzylamide | 512.632 | 513.13 | 2.84 |
| 28-19 | 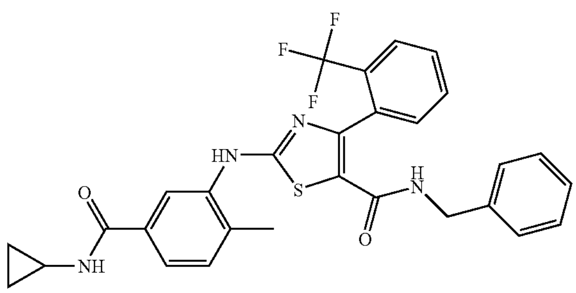 | 2-(5-Cyclopropylcar-bamoyl-2-methyl-phenylamino)-4-(2-trifluoromethyl-phenyl)-thiazole-5-carboxylic acid benzylamide | 550.603 | 551.1 | 2.92 |
| 28-20 | 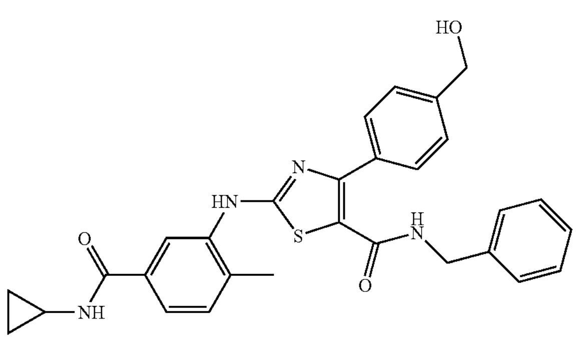 | 2-(5-Cyclopropylcar-bamoyl-2-methyl-phenylamino)-4-(4-hydroxymethyl-phenyl)-thiazole-5-carboxylic acid benzylamide | 512.632 | 513.12 | 2.32 |

TABLE 1-continued

| Example | Structure | Name | MW | m/z | T$_r$ |
|---|---|---|---|---|---|
| 28-21 | 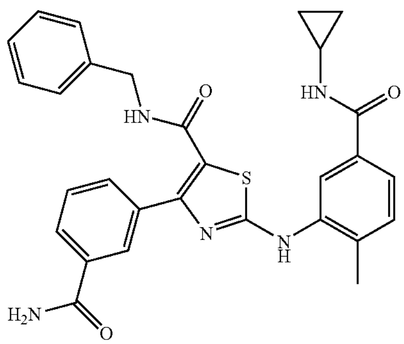 | 4-(3-Carbamoylphen-yl)-2-(5-cyclopropyl-carbamoyl-2-methyl-phenylamino)-thiazole-5-carboxylic acid benzylamide | 525.631 | 526.0 | 2.22 |
| 28-22 | 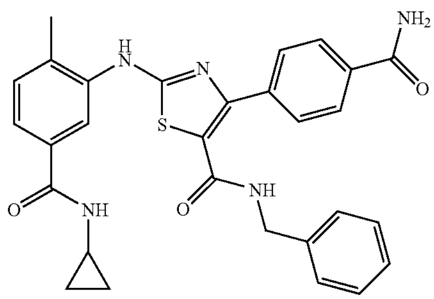 | 4-(4-Carbamoyl-propylcarbamoyl-2-methylphenylamino)-thiazole-5-carboxylic acid benzylamide | 525.631 | 256.1 | 2.17 |
| 28-23 | 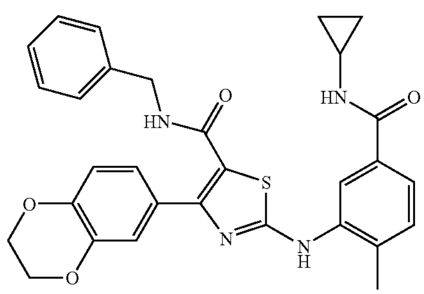 | 2-(5-Cyclopropylcar-bamoyl-2-methyl-phenylamino)-4-(2,3-dihydrobenzo[1,4]di-oxin-6-yl)-thiazole-5-carboxylic acid benzylamide | 540.642 | 541.1 | 2.73 |
| 28-24 | 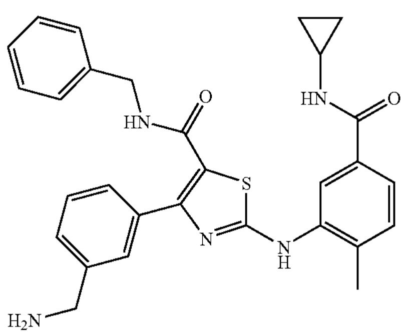 | 4-(3-Aminomethyl-phenyl)-2-(5-cyclo-propylcarbamoyl-2-methylphenylamino) thiazole-5-carboxylic acid benzylamide | 511.648 | 512.1 | 1.93 |

TABLE 1-continued

| Example | Structure | Name | MW | m/z | T$_r$ |
|---|---|---|---|---|---|
| 28-25 | 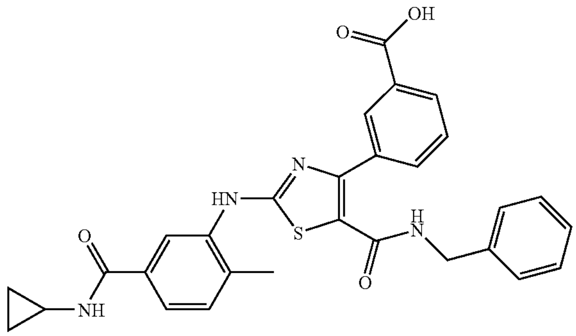 | 3-[5-Benzylcarbamoyl-2-(5-cyclopropylcarbamoyl-2-methyl-phenylamino)-thiazol-4-yl]-benzoic acid | 526.615 | 527 | 2.41 |
| 28-26 | 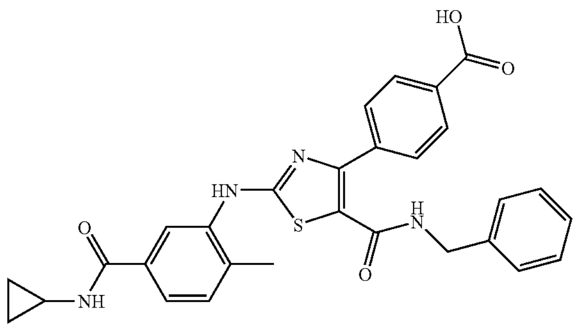 | 4-[5-Benzylcarbamoyl-2-(5-cyclopropylcarbamoyl-2-methyl-phenylamino)thiazol-4-yl]-benzoic acid | 526.615 | 257.32 | 1.53 |
| 28-27 | 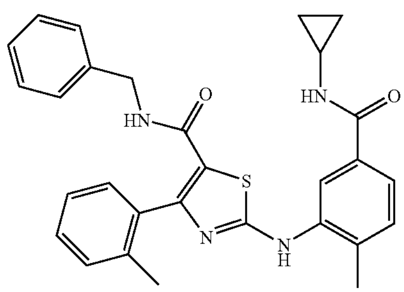 | 2-(5-Cyclopropylcarbamoyl-2-methyl-phenylamino)-4-o-tolyl-thiazole-5-carboxylic acid benzylamide | 496.633 | 497.22 | 2.41 |
| 28-28 | 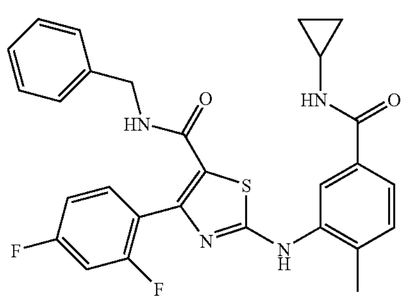 | 2-(5-Cyclopropylcarbamoyl-2-methyl-phenylamino)-4-(2,4-difluoro-phenyl)-thiazole-5-carboxylic acid benzylamide | 518.586 | 519.19 | 2.33 |
| 28-29 | 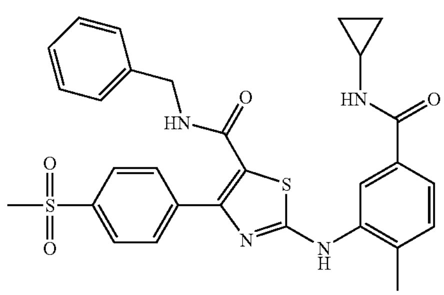 | 2-(5-Cyclopropylcarbamoyl-2-methyl-phenylamino)-4-(4-methanesulfonyl-phenyl)-thiazole-5-carboxylic acid benzylamide | 560.695 | 561.1 | 2.24 |

TABLE 1-continued

| Example | Structure | Name | MW | m/z | T$_r$ |
|---|---|---|---|---|---|
| 28-30 | 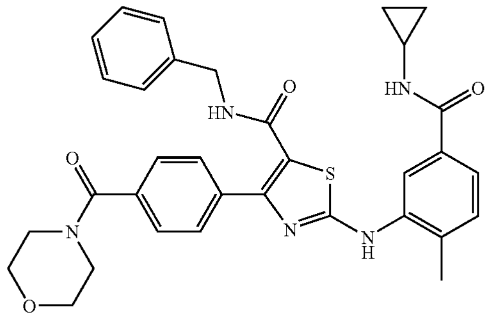 | 2-(5-Cyclopropylcarbamoyl-2-methylphenylamino)-4-[4-(morpholine-4-carbonyl)-phenyl]-thiazole-5-carboxylic acid benzylamide | 595.722 | 596.2 | 2.13 |
| 28-31 | 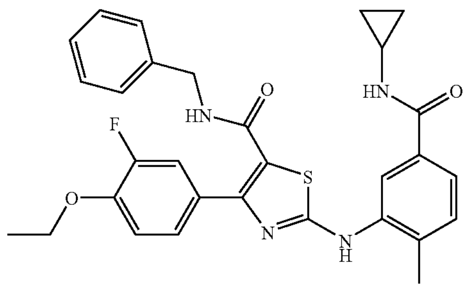 | 2-(5-Cyclopropylcarbamoyl-2-methylphenylamino)-4-(4-ethoxy-3-fluorophenyl)-thiazole-5-carboxylic acid benzylamide | 544.649 | 545.21 | 2.63 |
| 28-32 | 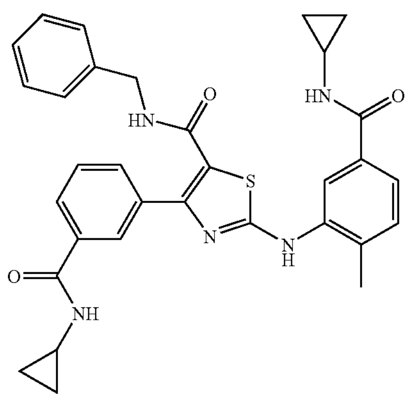 | 2-(5-Cyclopropylcarbamoyl-2-methylphenylamino)-4-(3-cyclopropylcarbamoyl-phenyl)-thiazole-5-carboxylic acid benzylamide | 565.696 | 477.12 | 2.19 |
| 28-33 | 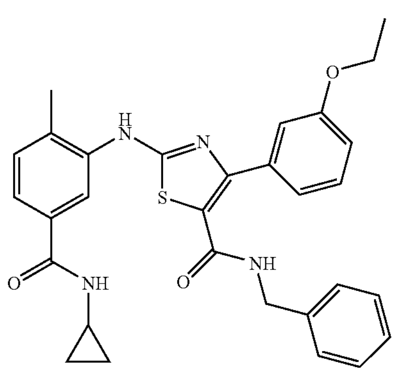 | 2-(5-Cyclopropylcarbamoyl-2-methylphenylamino)-4-(3-ethoxy-phenyl)-thiazole-5-carboxylic acid benzylamide | 526.659 | 527.1 | 2.6 |

TABLE 1-continued

| Example | Structure | Name | MW | m/z | T$_r$ |
|---|---|---|---|---|---|
| 28-34 | 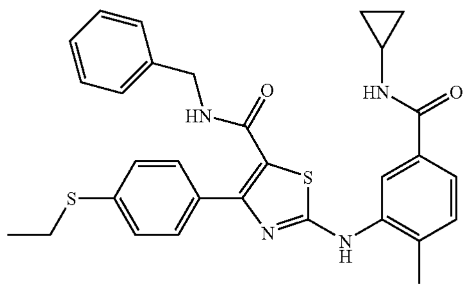 | 2-(5-Cyclopropylcar-bamoyl-2-methyl-phenylamino)-4-(4-ethylsulfanyl-phenyl)-thiazole-5-carboxylic acid benzylamide | 542.724 | 543.2 | 2.73 |
| 28-35 | 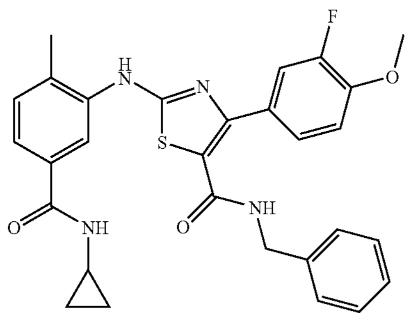 | 2-(5-Cyclopropylcar-bamoyl-2-methyl-phenylamino)-4-(3-fluoro-4-methoxy-phenyl)-thiazole-5-carboxylic acid benzylamide | 530.622 | 531.17 | 2.46 |
| 28-36 | 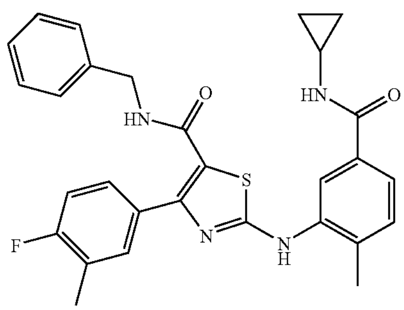 | 2-(5-Cyclopropylcar-bamoyl-2-methyl-phenylamino)-4-(4-fluoro-3-methyl-phenyl)-thiazole-5-carboxylic acid benzylamide | 514.623 | 515.24 | 2.61 |
| 28-37 | 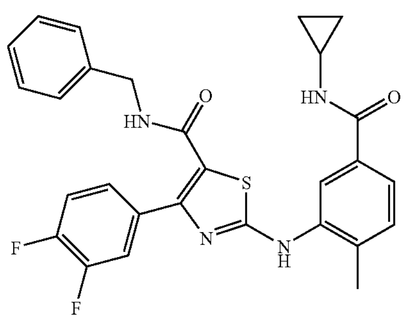 | 2-(5-Cyclopropylcar-bamoyl-2-methyl-phenylamino)-4-(3,4-difluoro-phenyl)-thiazole-5-carboxylic acid benzylamide | 518.586 | 519.08 | 2.52 |
| 28-38 | 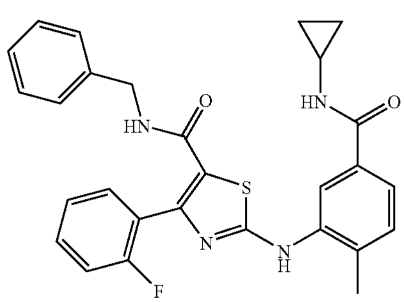 | 2-(5-Cyclopropylcar-bamoyl-2-methyl-phenylamino)-4-(2-fluoro-phenyl)-thiazole-5-carboxylic acid benzylamide | 500.596 | 501.14 | 2.39 |

TABLE 1-continued

| Example | Structure | Name | MW | m/z | T$_r$ |
|---|---|---|---|---|---|
| 28-39 | 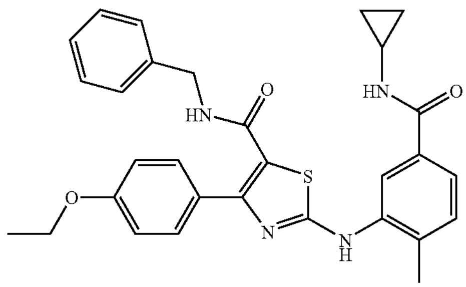 | 2-(5-Cyclopropylcarbamoyl-2-methylphenylamino)-4-(4-ethoxy-phenyl)-thiazole-5-carboxylic acid benzylamide | 526.659 | 527.27 | 2.57 |
| 28-40 | 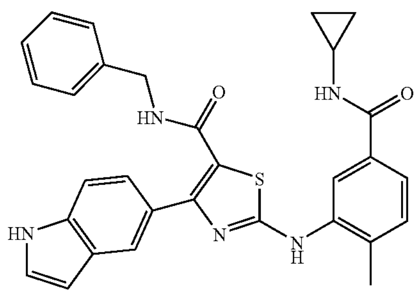 | 2-(5-Cyclopropylcarbamoyl-2-methylphenylamino)-4-(1H-indol-5-yl)-thiazole-5-carboxylic acid benzylamide | 521.643 | 522.24 | 2.32 |
| 28-41 | 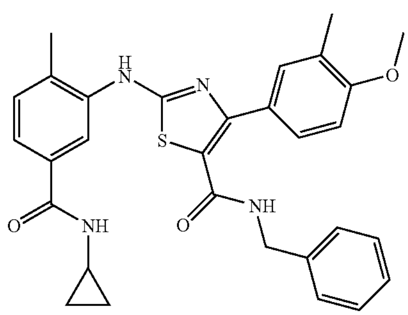 | 2-(5-Cyclopropylcarbamoyl-2-methylphenylamino)-4-(4-methoxy-3-methyl-phenyl)-thiazole-5-carboxylic acid benzylamide | 526.659 | 527.2 | 2.59 |
| 28-42 | 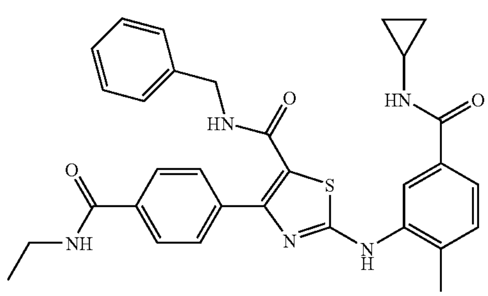 | 2-(5-Cyclopropylcarbamoyl-2-methylphenylamino)-4-(4-ethylcarbamoyl-phenyl)-thiazole-5-carboxylic acid benzylamide | 553.685 | 554.1 | 2.11 |
| 28-43 | 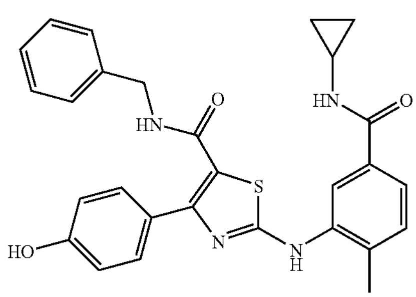 | 2-(5-Cyclopropylcarbamoyl-2-methylphenylamino)-4-(4-hydroxy-phenyl)thiazole-5-carboxylic acid benzylamide | 498.605 | 499.1 | 2.16 |

TABLE 1-continued

| Example | Structure | Name | MW | m/z | T_r |
|---|---|---|---|---|---|
| 28-44 | 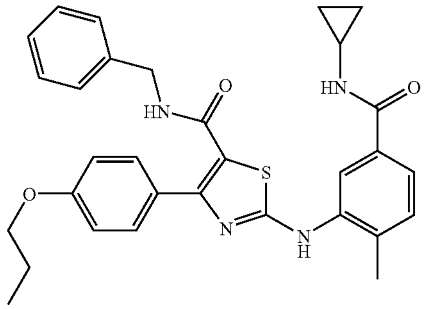 | 2-(5-Cyclopropylcarbamoyl-2-methyl-phenylamino)-4-(4-propoxy-phenyl)-thiazole-5-carboxylic acid benzylamide | 540.686 | 541.2 | 2.75 |
| 28-45 | 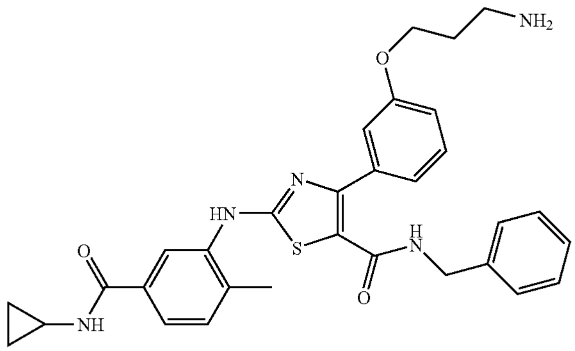 | 4-[3-(3-Amino-propoxy)-phenyl]-2-(5-cyclopropylcarbamoyl-2-methyl-phenylamino)-thiazole-5-carboxylic acid benzylamide | 555.701 | 361.22 | 1.61 |
| 28-46 | 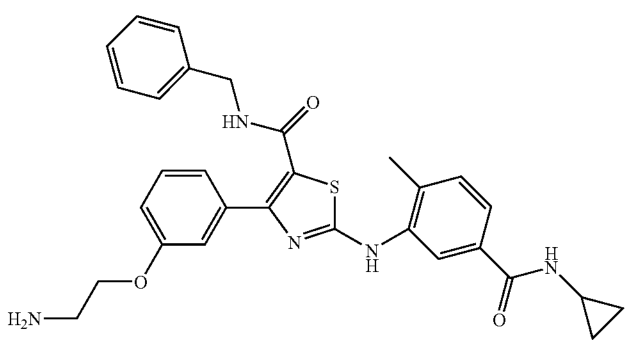 | 4-[3-(2-Amino-ethoxy)-phenyl]-2-(5-cyclopropylcarbamoyl-2-methylphenyl-amino)-thiazole-5-carboxylic acid benzylamide | 541.674 | 542.16 | 1.63 |
| 28-47 | 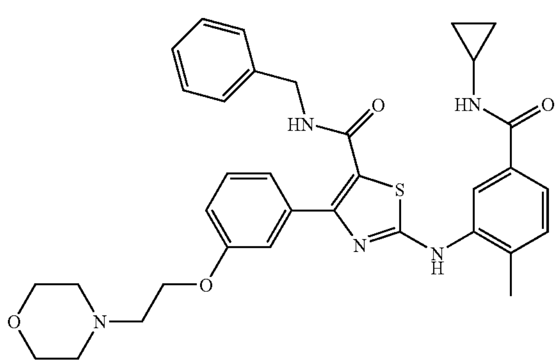 | 2-(5-Cyclopropylcarbamoyl-2-methyl-phenylamino)-4-[3-(2-morpholin-4-yl-ethoxy)-phenyl]-thiazole-5-carboxylic acid benzylamide | 611.765 | 612.2 | 2.32 |

EXAMPLE 29

2-(5-Cyclopropylcarbamoyl-2-methyl-phenylamino)-4-(3-methanesulfonylaminophenyl)-thiazole-5-carboxylic acid benzylamide

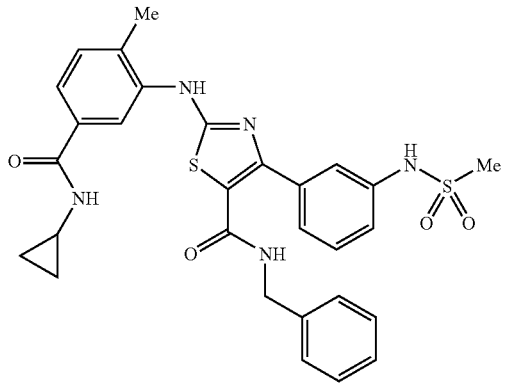

The title compound was prepared as in Example 28 from compound 27 and 3-(methanesulfonylamino)phenyl boronic acid. Purification by flash chromatography on SiO$_2$ (MeOH 1 to 5% in CH$_2$Cl$_2$) afforded the title compound as an off white solid (81% yield). HPLC (4 minutes gradient) t$_R$ 2.55 min; MS m/z 576.1 [M+H]$^+$; $^1$H NMR (DMSO-d$_6$, 300 MHz) δ 0.55 (m, 2H), 0.68 (m, 2H), 2.32 (s, 3H), 2.83 (m, 1H), 2.97 (s, 3H), 4.32 (d, J=5.5, 2H), 7.15-7.35 (m, 9H), 7.54 (m, 2H), 8.25 (s, 1H), 8.40 (m, 2H), 9.81 (s, 2H) ppm.

EXAMPLE 30

4-(4-Amino-phenyl)-2-(5-cyclopropylcarbamoyl-2-methyl-phenylamino)-thiazole-5-carboxylic acid benzylamide

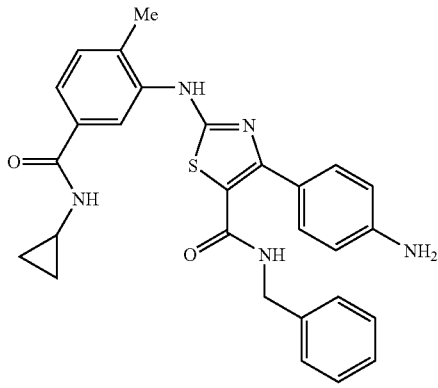

The title compound was prepared as in Example 28 from compound 27 and 4-(4,4,5,5-tetramethyl-1,3,2-dioxaborolan-2-yl)aniline. Purification by flash chromatography (SiO$_2$, MeOH 1 to 4% in CH$_2$Cl$_2$) provided the title compound as a brown solid (83% yield). HPLC (4 minutes gradient) t$_R$ 2.10 min; MS m/z 498.13 [M+H]$^+$; $^1$H NMR (DMSO-d$_6$, 300 MHz) δ 0.56 (m, 2H), 0.68 (m, 2H), 2.31 (s, 3H), 2.84 (m, 1H), 4.32 (d, J=5.7, 2H), 5.37 (s, 2H), 6.50 (d, J=8.3, 2H), 7.20-7.36 (m, 8H), 7.50 (d, J=7.5, 1H), 8.04 (br t, 1H), 8.35 (s, 1H), 8.39 (d, J=3.7, 1H), 9.62 (s, 1H) ppm.

EXAMPLE 31

4-(3-Amino-phenyl)-2-(5-cyclopropylcarbamoyl-2-methyl-phenylamino)-thiazole-5-carboxylic acid benzylamide

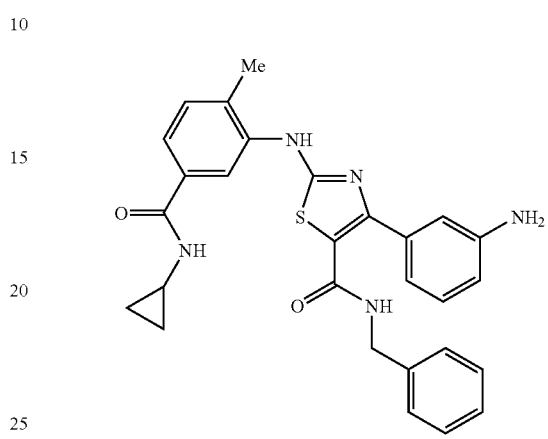

The title compound was prepared as in Example 28 from compound 27 and 3-aminophenylboronic acid hydrochloride. Flash chromatography (SiO$_2$, MeOH 1 to 6% in CH$_2$Cl$_2$) afforded the title compound as an off white solid (59% yield). HPLC (4 minutes gradient) t$_R$ 2.08 min; MS m/z 498.10 [M+H]$^+$; $^1$H NMR (DMSO-d$_6$, 300 MHz) δ 0.56 (m, 2H), 0.62 (m, 2H), 2.31 (s, 3H), 2.73 (m, 1H), 4.31 (d, J=5.5, 2H), 5.12 (s, 2H), 6.56 (d, J=7.6, 1H), 6.72 (d, J=7.4, 1H), 6.84 (s, 1H), 6.98 (t, J=7.7, 1H), 7.18-7.33 (m, 6H), 7.53 (d, J=7.6, 1H), 7.89 (br t, 1H), 8.21 (s, 1H), 8.38 (d, J=3.5, 1H), 9.71 (s, 1H) ppm.

EXAMPLE 32

({3-[5-Benzylcarbamoyl-2-(5-cyclopropylcarbamoyl-2-methyl-phenylamino)-thiazol-4-yl]-phenylcarbamoyl}-methyl)-carbamic acid tert-butyl ester

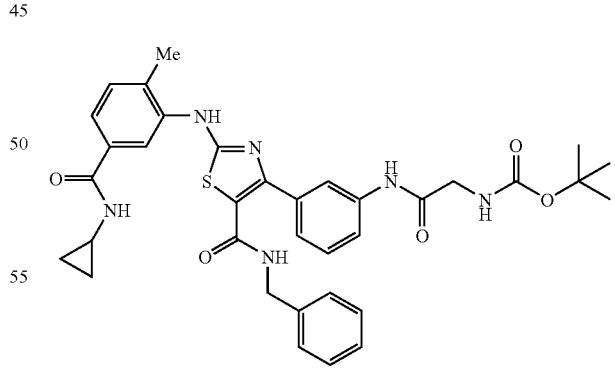

To a stirred solution of compound 31 (29 mg, 0.058 mmol) in anhydrous DMF (0.5 ml) was added N-Boc glycine (10 mg, 0.057 mmol), EDCI (13 mg, 0.069 mmol), HOBt.H$_2$O (11 mg, 0.072 mmol) and DMAP (1 crystal, catalytic). The reaction mixture was heated at 50° C. for 7 hr. After cooling to room temperature, the crude mixture was poured on a SiO$_2$ column and eluted with MeOH 1 to 5% in CH$_2$Cl$_2$. The compound was dissolved in CH$_2$Cl$_2$ and filtered through a pad of celite to afford the title compound as an off white solid (16 mg, 0.0244 mmol, 42%). HPLC (4 minutes gradient) t_R 2.78 min; MS m/z 654.88 [M+H]$^+$; $^1$H NMR (DMSO-d$_6$, 300 MHz) δ 0.56 (m, 2H), 0.67 (m, 2H), 1.39 (s, 9H), 2.31 (s, 3H), 2.83 (m, 1H), 3.72 (d, J=5.8, 2H), 4.30 (d, J=5.5, 2H), 7.07 (t, J=5.8, 1H), 7.18-7.35 (m, 8H), 7.55 (m, 2H), 7.91 (s, 1H), 8.22 (m, 2H), 8.39 (d, J=3.7, 1H), 9.80 (s, 1H), 10.00 (s, 1H) ppm.

EXAMPLE 33

(2-{3-[5-Benzylcarbamoyl-2-(5-cyclopropylcarbamoyl-2-methyl-phenylamino)-thiazol-4-yl]-phenylcarbamoyl}-ethyl)-carbamic acid tert-butyl ester

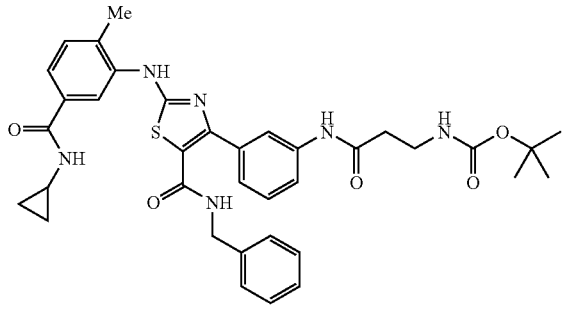

Prepared according to the procedure for Example 32 starting from N-Boc β-alanine. Flash chromatography (SiO$_2$, MeOH 1 to 6% in CH$_2$Cl$_2$) afforded the title compound as an off white solid (49% yield). HPLC (4 minutes gradient) t_R 2.81 min; MS m/z 668.71 [M+H]$^+$; $^1$H NMR (DMSO-d$_6$, 300 MHz) δ one signal overlapped by solvents signals 0.55 (m, 2H), 0.67 (m, 2H), 1.37 (s, 9H), 2.32 (s, 3H), 2.83 (m, 1H), 3.22 (m, 2H), 4.31 (d, J=5.5, 2H), 6.89 (br t, 1H), 7.18-7.35 (m, 8H), 7.55 (d, J=7.7, 1H), 7.61 (br s, 1H), 7.89 (s, 1H), 8.21 (s, 2H), 8.39 (d, J=3.6, 1H), 9.78 (s, 1H), 10.01 (s, 1H) ppm.

EXAMPLE 34

({4-[5-Benzylcarbamoyl-2-(5-cyclopropylcarbamoyl-2-methyl-phenylamino)-thiazol-4-yl]-phenylcarbamoyl}-methyl)-carbamic acid tert-butyl ester

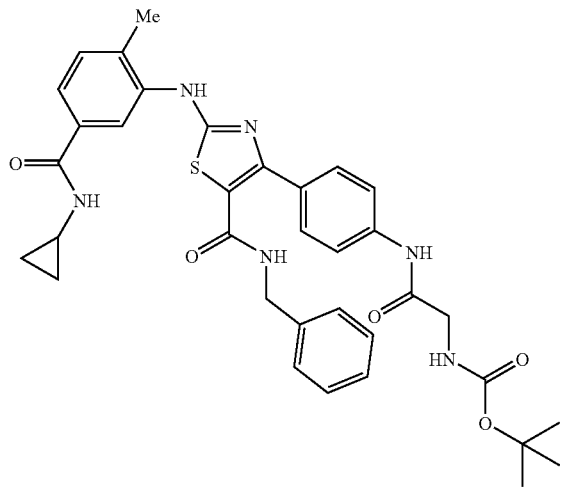

Prepared according to the procedure for Example 32 starting from compound 30. Flash chromatography (SiO$_2$, MeOH 1 to 6% in CH$_2$Cl$_2$) provided the title compound as a glassy solid (72% yield). HPLC (4 minutes gradient) t_R 2.49 min; MS m/z 655.01 [M+H]$^+$; $^1$H NMR (DMSO-d$_6$, 500 MHz) δ 0.55 (m, 2H), 0.67 (m, 2H), 1.39 (s, 9H), 2.30 (s, 3H), 2.83 (m, 1H), 3.72 (d, J=5.8, 2H), 4.31 (d, J=5.7, 2H), 7.06 (br t, 1H), 7.22 (d, J=7.5, 2H), 7.30 (d, J=7.8, 2H), 7.50-7.58 (m, 5H), 8.33-8.38 (m, 3H), 9.72 (s, 1H), 10.01 (s, 1H) ppm.

EXAMPLE 35

(2-{4-[5-Benzylcarbamoyl-2-(5-cyclopropylcarbamoyl-2-methyl-phenylamino)-thiazol-4-yl]-phenylcarbamoyl}-ethyl)-carbamic acid tert-butyl ester

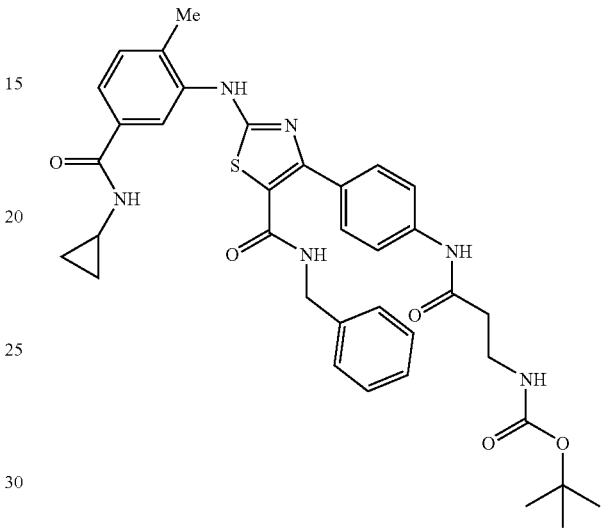

Prepared according to the procedure for Example 33 starting from compound 30. Purification by flash chromatography (SiO$_2$, MeOH 1 to 6% in CH$_2$Cl$_2$) afforded the title compound as an off white solid (64% yield). HPLC (4 minutes gradient) t_R 2.51 min; MS m/z 668.89 [M+H]$^+$; $^1$H NMR (DMSO-d$_6$, 500 MHz) δ one signal overlapped by solvent signals 0.55 (m, 2H), 0.67 (m, 2H), 1.36 (s, 9H), 2.30 (s, 3 H), 2.83 (m, 1H), 3.20 (m, 2H), 4.30 (d, J=5.8, 2H), 6.90 (br t, 1H), 7.23 (m, 3H), 7.31 (m, 3H), 7.50 (d, J=7.1, 1H), 7.56 (s, 3H), 8.32-8.37 (m, 3H), 9.69 (s, 1H), 10.02 (s, 1H) ppm.

EXAMPLE 36

4-[3-(2-Amino-acetylamino)-phenyl]-2-(5-cyclopropylcarbamoyl-2-methyl-phenylamino)-thiazole-5-carboxylic acid benzylamide ditrifluoroacetate

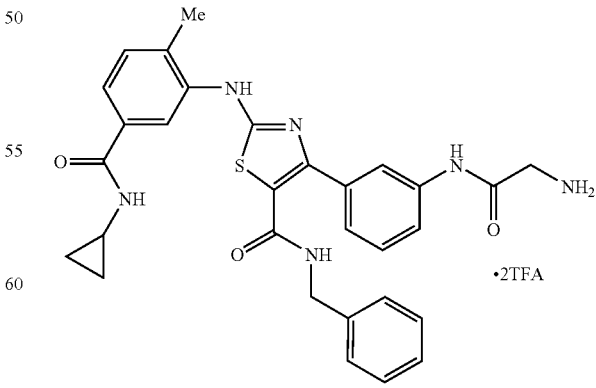

To a stirred solution of compound 32 (14 mg, 0.0214 mmol) in CH$_2$Cl$_2$ (1 ml) was added trifluoroacetic acid (0.3 ml). The mixture was stirred at room temperature for 2 hours. The volatiles were removed in vacuo to afford the title compound ditrifluoroacetamide salt as an off white glassy material (17 mg, 0.0217 mmol, 100%). HPLC (4 minutes gradient) $t_R$ 1.97 min; MS m/z 555.05 [M+H]$^+$; $^1$H NMR (DMSO-$d_6$, 300 MHz) δ 0.57 (m, 2H), 0.67 (m, 2H), 2.32 (s, 3H), 2.83 (m, 1H), 3.78 (d, J=5.3, 2H), 4.32 (d, J=5.4, 2H), 7.19-7.35 (m, 9H), 7.55 (d, J=7.7, 1H), 7.63 (d, J=7.1, 1H), 7.84 (s, 1H), 8.08 (br s, 3H), 8.23 (s, 1H), 8.40 (br s, 2H), 9.78 (s, 1H), 10.45 (s, 1H) ppm.

EXAMPLE 37

4-[3-(3-Amino-propionylamino)-phenyl]-2-(5-cyclopropylcarbamoyl-2-methyl-phenylamino)-thiazole-5-carboxylic acid benzylamide ditrifluoroacetate

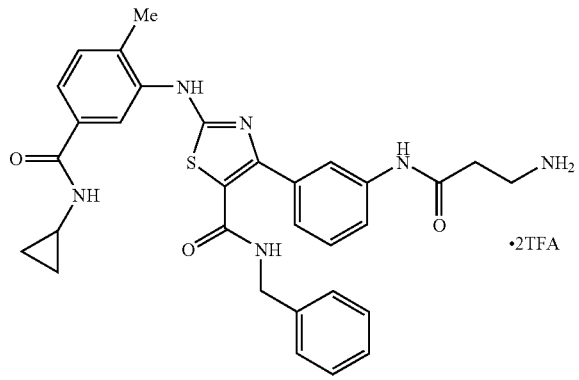

The title compound was prepared according to the procedure for Example 36 starting from compound 33 as a colorless glassy material (100%). HPLC (4 minutes gradient) $t_R$ 1.94 min; MS m/z 569.10 [M+H]$^+$; $^1$H NMR (DMSO-$d_6$, 300 MHz) δ some signals are overlapped by the solvents signals 0.55 (m, 2H), 0.67 (m, 2H), 2.32 (s, 3H), 2.82 (m, 1H), 3.09 (m, 2H), 4.32 (d, J=5.5, 2H), 7.19-7.35 (m, 9H), 7.54 (d, J=7.8, 1H), 7.63 (d, J=6.8, 1H), 7.72 (br s, 3H), 7.87 (s, 1H), 8.23 (s, 1H), 8.28 (t, J=5.7, 1H), 8.39 (d, J=3.8, 1H), 9.75 (s, 1H), 10.20 (s, 1H) ppm.

EXAMPLE 38

4-[4-(2-Amino-acetylamino)-phenyl]-2-(5-cyclopropylcarbamoyl-2-methyl-phenylamino)-thiazole-5-carboxylic acid benzylamide ditrifluoroacetate

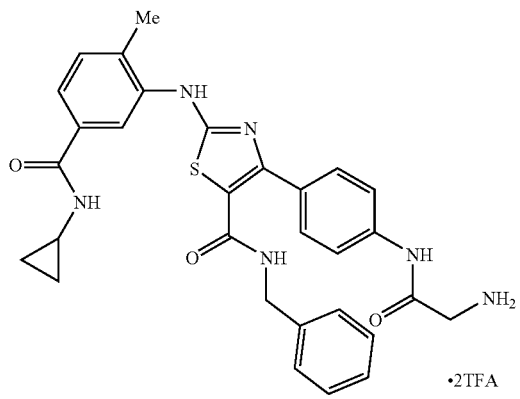

The title compound was prepared according to the procedure for Example 36 starting from compound 34 as an off white solid (100% yield). HPLC (4 minutes gradient) $t_R$ 1.90 min; MS m/z 555.20 [M+H]$^+$; $^1$H NMR (DMSO-$d_6$, 500 MHz) δ 0.55 (m, 2H), 0.68 (m, 2H), 2.30 (s, 3H), 2.83 (m, 1H), 3.79 (d, J=5.6, 2H), 4.32 (d, J=5.8, 2H), 7.24 (d, J=7.5, 2H), 7.30 (d, J=5.4, 2H), 7.50 (d, J=7.4, 1H), 7.54 (d, J=8.5, 2H), 7.62 (d, J=8.5, 2H), 8.08 (br s, 3H), 8.38 (d, J=3.9, 2H), 8.45 (d, J=5.9, 1H), 9.69 (s, 1H), 10.48 (s, 1H) ppm.

EXAMPLE 39

2-{4-[5-benzylcarbamoyl-2-(5-cyclopropylcarbamoyl-2-methyl-phenylamino)-thiazol-4-yl]-phenylcarbamoyl}-ethyl-ammonium ditrifluoroacetate

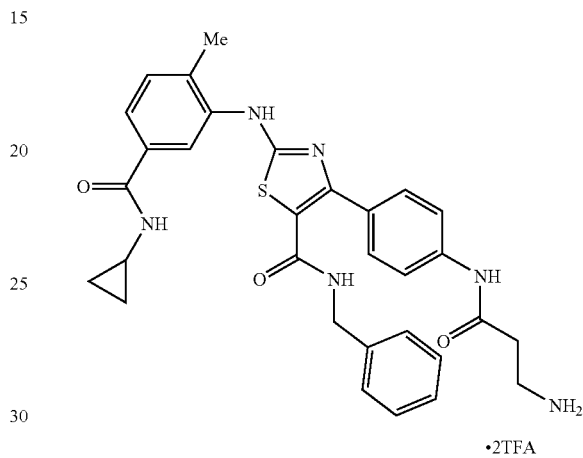

The title compound was prepared according to the procedure for Example 36 starting from compound 35 as an off white solid (100% yield). HPLC (4 minutes gradient) $t_R$ 1.89 min; MS m/z 569.13 [M+H]$^+$; $^1$H NMR (DMSO-$d_6$, 500 MHz) δ 0.55 (m, 2H), 0.68 (m, 2H), 2.30 (s, 3H), 4.51 (t, J=6.5, 2H), 2.83 (m, 1H), 3.09 (q, J=6.0, 2 H), 4.32 (d, J=5.7, 2H), 7.23 (d, J=7.5, 2H), 7.30 (d, J=5.9, 2H), 7.50 (d, J=7.6, 1H), 7.56 (d, J=8.7, 2H), 7.60 (d, J=8.6, 2H), 7.70 (brs, 3H), 8.37-8.43 (m, 3H), 9.68 (s, 1H), 10.23 (s, 1H) ppm.

EXAMPLE 40

4-(4-Cyanomethyl-phenyl)-2-(5-cyclopropylcarbamoyl-2-methyl-phenylamino)-thiazole-5-carboxylic acid benzylamide

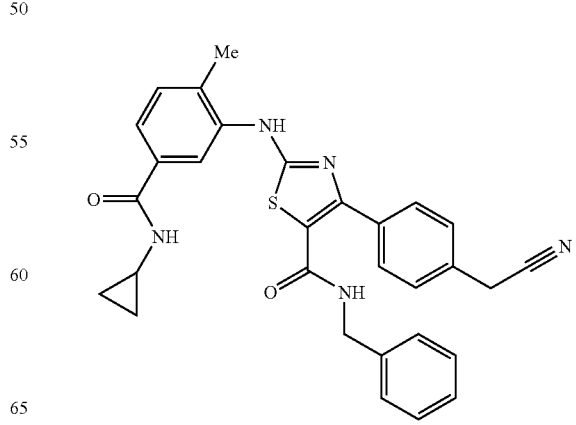

The title compound was prepared by the method of Example 28 from compound 27 and 4-cyanomethylphenyl-boronic acid. Purification by flash chromatography (SiO$_2$, MeOH 1 to 3% in CH$_2$Cl$_2$) provided the desired compound 40 as an off white solid (73% yield). HPLC (4 minutes gradient) $t_R$ 2.66 min; MS m/z 522.10 [M+H]$^+$; $^1$H NMR (DMSO-d$_6$, 300 MHz) δ 0.56 (m, 2H), 0.68 (m, 2H), 2.27 (s, 3H), 2.85 (m, 1H), 4.08 (s, 2H), 4.32 (d, J=5.5, 2H), 7.22-7.33 (m, 8H), 7.53 (d, J=7.7, 1H), 7.64 (d, J=7.8, 2H), 8.36 (s, 1H), 8.40 (d, J=3.4, 1H), 8.48 (br t, 1H), 9.77 (s, 1H) ppm.

EXAMPLE 41

4-[4-(2-Amino-ethyl)-phenyl]-2-(5-cyclopropylcar-bamoyl-2-methyl-phenylamino)-thiazole-5-carboxy-lic acid benzylamide

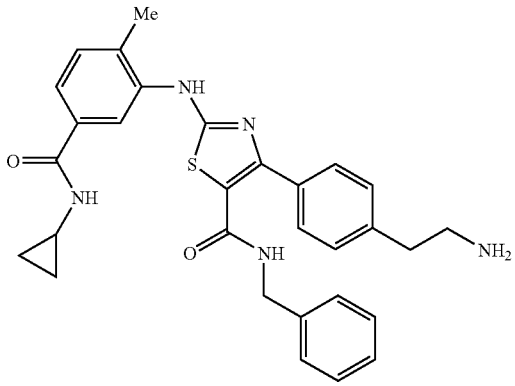

Prepared using chemistry described in J. Med. Chem., 2003, 46, 345-348. To a stirred suspension of compound 40 (45 mg, 0.0862 mmol) in MeOH (1.5 ml) was added cobalt chloride hexahydrate (0.172 mmol). Upon addition of NaBH$_4$ (33 mg, 0.872 mmol) the solution turned black instantly. After stirring at room temperature for 1 hour, 1N HCl was added (5 ml) and the mixture filtered through a pad of celite. The solution was alkalinized by adding concentrated NH$_4$OH and the compound extracted with CH$_2$Cl$_2$ (3×). After drying of the extracts over MgSO$_4$ and removal of the solvents, the crude product was purified by flash chromatography on silica gel eluted with 1 to 10% MeOH in CH$_2$Cl$_2$ to remove impurities, then 10:1:89 MeOH/NEt$_3$/CH$_2$Cl$_2$ to elute the title compound as an off white solid (34% yield). HPLC (4 minutes gradient) $t_R$ 1.93; MS m/z 526.13 [M+H]$^+$; $^1$H NMR (DMSO-d$_6$, 300 MHz) δ 0.56 (m 2H), 0.68 (m, 2H), 2.32 (s, 3H), 2.76 (m, 2H), 2.89 (m, 3H), 4.32 (d, J=5.6, 2H), 7.16-7.33 (m, 9H), 7.50-7.58 (m, 3H), 8.39 (m, 3H) ppm.

EXAMPLE 42

The ability of the compounds provided herein to inhibit the synthesis or the activity of cytokines can be demonstrated using the following in vitro assays.

Generation of p38 Kinases cDNAs of human p38α and β were cloned by PCR. The α and β cDNAs were subcloned into DEST2 plasmid (Gateway, InVitrogen). His$_6$-p38 fusion protein was expressed in *E. coli* and purified from bacterial lysates by affinity chromatography using Ni$^{+2}$-NTA-agarose. His$_6$-p38 protein was activated by incubating with constitutively active MKK6. Active p38 was separated from MKK6 by affinity chromatography. Con-stitutively active MKK6 was generated in a manner similar to Raingeaud et al. (Mol. Cell. Biol., 1247-1255 (1996)).

TNF-α Production by LPS-Stimulated PBMCs

Heparinized human whole blood was obtained from healthy volunteers. Peripheral blood mononuclear cells (PB-MCs) were purified from human whole blood by Accu-paque density gradient centrifugation and resuspended at a concentration of 5×10$^6$/ml in assay medium (RPMI medium containing 10% fetal bovine serum). 175 uL of cell suspension was incubated with 10 uL of test compound (in 4% DMSO) in 96-well tissue culture plates for 30 minutes at RT. 15 uL of LPS (13.33 ug/ml stock) was then added to the cell suspension and the plate was incubated for 18 hours at 37° C. in a humidified atmosphere containing 5% CO$_2$. Following incubation, the culture medium was collected and stored at −20° C.

THP-1 cells (TIB-202, ATCC) were washed and resuspended at a concentration of 1×10$^5$/ml in assay medium (RPMI medium containing 3% fetal bovine serum). 175 uL of cell suspension was incubated with 10 uL of test compound (in 4% DMSO) in 96-well tissue culture plates for 30 minutes at RT. 15 uL of LPS (13.33 ug/ml stock) was then added to the cell suspension and the plate was incubated for 18 hours at 37° C. in a humidified atmosphere containing 5% CO$_2$. Following incubation, the culture medium was collected and stored at −20° C.

TNF-α concentration in the medium was quantified using a standard ELISA kit (BioSource International, Camarillo, Calif.). Concentrations of TNF-α and IC$_{50}$ values for test compounds (concentration of compound that inhibited LPS-stimulated TNF-α production by 50%) were calculated by four parameter logistic curve (SigmaPlot, SPSS, Inc.).

p38α Assay

The p38α assay employed is based on measurement of ADP released in the reaction of interest through NADH oxidation obtained by coupling with pyruvate kinase and lactate dehydrogenase reactions. The assays were performed in 384-well UV-plates. The final volume was 25 uL prepared from the addition of 2.5 uL compound dissolved in 10% DMSO, 17.5 uL of assay buffer and 5 uL of ATP. Assay buffer contains the following reagents to give final concentration in the assay: 25 mM HEPES, 20 mM 2-glycerophosphate, pH 7.6, 10 mM MgCl$_2$, 0.1 mM sodium orthovanadate, 0.5 mM phospho-enolpyruvate, 0.12 mM NADH, 3.1 mg/ml LDH, 6.67 mg/ml pyruvate kinase, 0.25 mM peptide substrate, 2 mM DTT, 0.005% Tween 80 and 20 nM p38α kinase from Upstate. Test compounds are preincubated with p38α kinase for 60 min and the reaction started by addition of ATP to 0.15 mM final concentration. Reaction rates were measured at 340 nm using SpectraMax plate-reading spectrophotometer for 10 min at 37° C. Inhibition data were analyzed by non-linear least-squares regression using SigmaPlot.

TNF-α Production by LPS-Stimulated Mice

Mice (Balb/c female, 6-8 weeks of age, Taconic Labs; n=8/treatment group) were injected intraperitoneally with lipopolysaccharide (LPS) (50 ug/kg of *E. coli* strain 0111:B4, Sigma) suspended in sterile saline. Ninety minutes later, mice were sedated by CO$_2$:O$_2$ inhalation and a blood sample was obtained. Serum was separated and analyzed for TNF-α concentrations by commercial ELISA assay per the manufacturer's instructions (BioSource International). Test compounds were administered orally at various times before LPS injection. The compounds were dosed either as suspensions or as solutions in various vehicles or solubilizing agents.

Results

IC$_{50}$ data were obtained for the compounds provided herein. Most of the compounds exhibited p38α kinase IC$_{50}$ values of less than 10 μM, many less than 1 μM. Data for selected compounds is shown in the Table below.

| Compound | p38α kinase IC$_{50}$ (nM)* |
| --- | --- |
| 1 | +++ |
| 2 | +++ |
| 3 | + |
| 26 | +++ |
| 28-6 | ++ |
| 28-9 | ++ |
| 28-24 | +++ |
| 28-40 | + |

*+ refers to >100 nM
++ refers to 50-100 nM
+++ refers to <50 nM

Since modifications will be apparent to those of skill in this art, it is intended that the subject matter claimed herein be limited only by the scope of the appended claims.

What is claimed is:

1. A method of treating rheumatoid arthritis, comprising administering a compound of formula (I):

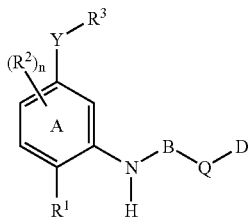

I or pharmaceutically acceptable derivatives thereof, wherein:
$R^1$ is hydrogen, methyl, halo, hydroxyl, lower alkyl, lower cycloalkyl, lower alkynyl, trifluoromethyl, methoxy, trifluoromethoxy, cyano, —NH$_2$, —NR$^4$R$^5$ or —OR$^4$;
$R^2$ is attached to any available carbon atom of the phenyl ring A and at each occurrence is independently selected from alkyl, substituted alkyl, lower cycloalkyl, halo, trifluoromethyl, trifluoromethoxy, —OR$^4$, —CN, —NR$^4$R$^5$; —S(=O)alkyl, —S(=O)aryl, —NHSO$_2$-arylene-R$^4$, —NHSO$_2$alkyl, —CO$_2$R$^4$, —CONH$_2$, —SO$_3$H, —S(O)alkyl, —S(O)aryl, —SO$_2$NHR$^4$, and —NHC(=O)NHR$^4$;
n is 0, 1 or 2;
$R^3$ is selected from hydrogen, alkyl, —OR$^4$, substituted alkyl, cycloalkyl, —CR$^4$cycloalkyl, heteroaryl, substituted heteroaryl, heterocycle and substituted heterocycle;
Y is —C(=O)NH—;
Z is NR$^4$, S or O;
B is 1,3-thiazole; 1,2,4-triazole; 1,2,4-thiadazole; 1,3-oxazole or 1,2,4-oxadiazole optionally substituted with up to two $R^{13}$;
Q is independently selected from a single bond, —O—, —S—, —NR$^4$—, —S(O)—, —SO$_2$—, —C(O)—, —CO(O)—, —C(O)NH—(C$_{0-4}$alkyl)- or —CH$_2$—;
D is a monocyclic or bicyclical ring system optionally containing up to four heteroatom's selected from N, O, and S, and wherein a CH$_2$ adjacent to any of the said N, O or S heteroatoms is optionally substituted with oxo (=O) or D is C$_1$-$_6$alkyl, and wherein D is optionally substituted by one to four (CR$^9$R$^{10}$)$_w$E groups;
w is an integer having a value from 0-4;

$R^{10}$ is selected from H, C$_1$-C$_4$ alkylhydroxy, C$_1$-C$_4$alkylaryl and C$_1$-C$_4$alkylheteroaryl, wherein said aryl or heteroaryl group is unsubstituted or substituted with 1-3 groups independently selected from halo, NO$_2$, C$_1$-C$_4$alkyl, C$_3$-C$_{10}$cycloalkyl, C$_2$-C$_6$alkenyl, C$_2$-C$_6$alkynyl, haloalkyl, haloalkoxy, OH, C$_1$-C$_4$alkoxy, C$_1$-C$_4$alkylcarbonyl, CN, NH$_2$, NR$^6$R$^7$, SR$^6$, S(O)R$^6$, SO$_2$R$^6$, SO$_3$R$^6$, SO$_2$NR$^6$, CO$_2$H, CO$_2$R$^6$, and CONR$^6$R$^7$;
E is selected from H, halogen, NO$_2$, C$_1$-C$_4$alkyl, C$_3$-C$_{10}$cycloalkyl, C$_2$-C$_6$alkenyl, C$_2$-C$_6$alkynyl, haloalkyl, haloaloxy, OH, OR$^6$, CN, CHO, CO$_2$R$^6$, CONR$^8$R$^7$, OCOR$_6$, OC(=O)OR$^6$, OC(=O)NR$^6$R$^7$, OCH$_2$CO$_2$R$^6$, C(=O)R$^6$, NH$_2$, NHR$^6$, NR$^6$R$^7$, NR$^7$C(=O)R$^6$, NR$^7$C(=O)OR$^6$, NR$^7$C(=O)C(=O)OR$^6$, NR$^7$C(=O)C(=O)NR$^6$R$^7$, NR$^7$C(=O)C(=O)(C$_1$-C$_6$alkyl), NR$^7$C(=NCN)OR$^6$, NR$^7$C(=O)NR$^6$R$^7$, NR$^7$C(=NCN)NR$^6$R$^7$, NR$^7$C(=NR$^6$)NR$^7$R$^8$, NR$^6$SO$_2$NR$^6$R$^7$, NR$^7$SO$_2$R$^6$, SR$^6$, S(=O)R$^6$, SO$_2$R$^6$, SO$_3$R$^7$, SO$_2$NR$^6$R$^7$, NHOH, NHOR$^6$, NR$^6$NR$^7$NR$^8$, N(COR$^6$)OH, N(CO$_2$R$^6$)OH, CONR$^7$(CR$^9$R$^{10}$)$_r$R$^6$, CO(CR$^9$R$^{10}$)$_p$O(CHR$^9$)$_q$CO$_2$R$^6$, CO(CR$^9$CR$^{10}$)$_r$R$^6$, CO(CR$^9$R$^{10}$)$_p$O(CR$^9$R$^{10}$)$_p$O(CHR$^9$)$_q$CO$_2$R$_6$, CO(CR$^9$CR$^{10}$)$_r$OR$^6$, CO(CR$^9$R$^{10}$)$_p$O(CR$^9$R$^{10}$)$_q$R$^6$, CO(CR$^6$CR$^{10}$)$_r$NR$^6$R$^7$, OC(O)O(CR$^9$R$^{10}$)$_m$NR$^6$R$^7$, O(CO)$_n$(CR$^9$R$^{10}$)$_r$R$^6$, O(CR$^9$R$^{10}$)$_m$NR$^6$R$^7$$_m$NR$^7$C(O) (CR$^9$R$^{10}$)$_r$OR$^6$, NR$^7$C(=NC)(CR$^9$R$^{10}$)$_r$R$^6$, NR$^7$CO(CR$^9$R$^{10}$)$_r$NR$^6$R$^7$, NR$^7$(CR$^9$R$^{10}$)$_m$OR$^6$, NR$^7$(CR$^9$R$^{10}$)$_r$CO$_2$R$^6$, NR$^7$(CR$^9$R$^{10}$)$_m$NR$^6$R$^7$, NR$^7$, NR$^3$(CR$^9$R$^{10}$)$_n$SO$_2$(CR$^9$R$^{10}$)$_r$CO$_2$R$^6$, NR$^7$(CR$^9$R$^{10}$)$_m$NR$^6$R$^7$, NR$^7$(CR$^9$R$^{10}$)$_n$SO$_2$(CR$^9$R$^{10}$)$_q$R$^6$, CONR$^7$ (CR$^9$R$^{10}$)$_n$SO$_2$(CR$^9$R$^{10}$)$_q$R$^6$, SO$_2$NR$^7$(CR$^9$R$^{10}$)$_q$R$^6$, SO$_2$NR$^6$(CR$^9$R$^{10}$)$_m$OR$^6$, C$_2$-C$_6$alkenyl, C$_3$-C$_{10}$cycloalkyl, C$_3$-C$_{10}$cycloalkylmethyl, aryl, heterocyclic optionally substituted with one or two alkyl groups, heteroaryl optionally substituted with one or two alkyl groups and alkylaryl, wherein said aryl groups are unsubstituted or substituted with 1 or 2 substituents each independently selected from R$^{12}$;
m is an integer having a value from 2-6;
p is an integer having a value from 1-3;
q is an integer having a value from 0-3;
r is an integer having a value from 0-6;
$R^{12}$ at each occurrence is independently selected from halo, NO$_2$, C$_1$-C$_4$alkyl, C$_3$-C$_{10}$cycloalkyl, C$_2$-C$_6$alkenyl, C$_2$-C$_6$alkynyl, haloalkyl, haloalkoxy, OH, oxo, C$_1$-C$_4$ alkoxy, OR$^6$, O(CR$^9$R$^{10}$)CO$_2$R$^6$, O(CR$^9$R$^{10}$)$_m$NR$^6$R$^7$, O(CR$^9$R$^{10}$)$_p$CN, O(CR$^9$R$^{10}$)$_r$C (=O)NR$^6$R$^7$, C$_1$-C$_4$alkylcarbonyl, CN, NH$_2$, NHR$^6$, NR$^6$R$^7$, NR$^7$(CR$^9$R$^{10}$)CO$_2$R$^6$, NR$^7$OR$^6$, NR$^7$(CR$^9$R$^{10}$)$_m$ OR$^6$, NR$^7$CH((CR$^9$R$^{10}$)$_p$OR$^6$)$_2$, NR$^7$C ((CR$^9$R$^{10}$)$_p$OR$^6$)$_3$, NR$^7$C(=O)R$^6$, NR$^7$(CR$^9$R$^{10}$)$_m$ NR$^6$R$^7$, NR$^7$(CR$^9$R$^{10}$)$_q$R$^6$, SR$^7$, S(O)R$^7$, SO$_2$R$^7$, SO$_2$NR$^6$, SO$_3$R$^7$, CO$_2$H, CO$_2$R$^6$, and CONR$^6$R$^7$;
$R^4$ is hydrogen, lower alkyl and lower cycloalkyl;
$R^5$ is hydrogen, lower alkyl and lower cycloalkyl;
$R^6$, $R^7$ and $R^8$ are independently selected as follows:
i) $R^6$, $R^7$ and $R^8$ are independently selected from H, C$_1$-C$_6$alkyl, C$_3$-C$_{10}$cycloalkyl, C$_2$-C$_6$alkenyl, C$_2$-C$_6$alkynyl, C$_1$-C$_6$alkylcarbonyl, C$_3$-C$_7$cycloalkyl (C$_O$-C$_5$alkyl)carbonyl, C$_1$-C$_6$ alkoxycarbonyl, aryl (C$_0$-C$_5$alkyl)carbonyl, aryl(C$_1$-C$_5$alkoxy)carbonyl, heterocyclic(C$_0$-C$_5$alkyl)carbonyl, heterocyclic(C$_1$-C$_5$alkoxy)carbonyl, C$_1$-C$_6$alkylsulfonyl, arylsulfonyl, heteroarylsulfonyl, C$_0$-C$_4$alkylaryl, C$_0$-C$_4$alkylheterocyclic, wherein said cycloalkyl, aryl, or heterocyclic groups are unsubstituted or substituted with 1 or 2 substituents each independently selected from the group consisting of $C_1$-$C_4$alkyl, hydroxyl, $C_1$-$C_4$alkoxy, F, Cl, Br, haloalkyl, $NO_2$ and CN; or, ii) $R^6$ and $R^7$, or $R^6$ and $R^8$, or $R^7$ and $R^8$ when both substituents are on the same nitrogen atom (as in (—$NR^6R^7$) or (—$NR^7R^8$)), can be taken together with the nitrogen atom to which they are attached to form a heterocycle selected from 1-aziridinyl, 1-azetidinyl, 1-piperidinyl, 1-morpholinyl, 1-pyrrolidinyl, thiamorpholinyl, thiazolidinyl, 1-piperazinyl, 1-imidazolyl, 3-azabicyclo(3,2,2)nonan-3yl, and 1-tetrazolyl, the said heterocycle being optionally substituted with 1-3 groups each independently selected from oxo, $C_0$-$C_4$alkylOH, $C_0$-$C_4$alkylOC$_1$-$C_4$alkyl, $C_0$-$C_4$alkylCONH$_2$, $C_0$-$C_4$alkylCO$_2$C$_0$-$C_4$alkyl, $C_1$-$C_4$alkyl, $C_1$-$C_4$alkoxy, $C_3$-$C_7$cycloalkyl, $C_0$-$C_6$alkylcarbonyl, $C_3$-$C_7$cycloalkylcarbonyl, $C_1$-$C_6$alkoxycarbonyl, $C_3$-$C_7$cycloalkoxycarbonyl, —NHCOalkyl, aryl, heteroaryl, arylalkoxycarbonyl, heteroarylalkoxycarbonyl, $C_1$-$C_6$alkylsulfonyl, arylsulfonyl and heteroarylsulfonyl;

$R^9$ is hydrogen or $C_1$-$C_4$alkyl; and $R^{13}$ is hydrogen, alkyl, haloalkyl, aminocarbonyl, hydroxycarbonyl, alkoxycarbonyl, cycloalkylalkylaminocarbonyl, substituted alkyl, aryl, substituted aryl, heteroaryl, heterocyclyl, alkylthio, alkylaminocarbonyl or lower cycloalkyl; where the substituents on alkyl group are selected from one to four substituents selected from halo, hydroxy, alkoxy, oxo (=O), alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkyithiono, arylthiono, aralkylthiono, alkylsulfonyl, arylsulfonyl, aralkylsulfonyl, sulfonamido, substituted sulfonamido, nitro, cyano, carboxy, carbamyl, substituted carbamyl, CONHaryl, CONHaralkyl or cases where there are two substituents on the nitrogen selected from alkyl, aryl or aralkyl; alkoxycarbonyl, aryl, substituted aryl, guanidino and substituted or unsubstituted heterocycles, indolyl, imidazolyl, furyl, thienyl, thiazolyl, pyrrolidyl, pyridyl, pyrimidyl and the substituents on aryl group are selected from one to four substituents selected from alkyl, substituted alkyl, haloalkyl, halo, trifluoromethoxy, trifluoromethyl, hydroxy, hydroxyalkyl, aminoalkyl, alkoxy, alkanoyl, alkanoyloxy, amino, arylamino, aralkylamino, dialkylamino, alkanoylamino, thiol, alkylthio, ureido, nitro, cyano, cyanoalkyl, heterocyclyl, carboxy, carboxyalkyl, carbamyl, alkoxycarbonyl, aminocarbonyl, alkylthiono, arylthiono, arylsulfonylamine, sulfonic acid, alkysulfonyl, sulfonamido, aryloxy and CONR$^a$R$^b$, where R$^a$ and R$^b$ are selected from hydrogen, alkyl, alkenyl, alkynyl, cycloalkyl, alkoxycarbonylaminoalkyl and alkylamino; or R$^a$ and R$^b$ together with the nitrogen on which they are substituted, form a 3-6 membered heterocyclic or heteroaryl ring; the substituent may be further substituted by hydroxy, alkyl, alkoxy, aryl, substituted aryl, substituted alkyl or aralkyl.

2. The method of claim 1, wherein $R^1$ is lower alkyl.

3. The method of claim 1, wherein $R^1$ is methyl.

4. The method of claim 1, wherein $R^2$ is hydrogen or alkyl.

5. The method of claim 1, wherein $R^2$ is hydrogen or lower alkyl.

6. The method of claim 1, wherein $R^2$ is hydrogen.

7. The method of claim 1, wherein $R^3$ is selected from alkyl, —$OR^4$, substituted alkyl, cydoalkyl, —$CR^4$cycloalkyl, heteroaryl, substituted heteroaryl, heterocycle and substituted heterocycle.

8. The method of claim 1, wherein $R^3$ is cycloalkyl, cycloalkylalkyl, alkoxyalkyl or heteroaryl.

9. The method of claim 1, wherein $R^3$ is methyl, isopropyl, ethyl, cyclopropyl, cyclopropylmethyl, methoxymethyl, oxazolyl or thiazolyl.

10. The method of claim 1, wherein B is a 1,3-thiazolyl ring optionally substituted with one or two $R^{13}$.

11. The method of claim 1, wherein B is a 1,3-thiazolyl ring optionally substituted with one $R^{13}$.

12. The method of claim 1, wherein Q is a single bond, —CO(O)—, —C(O)— or —C(O)NH—(C$_{0-4}$alkyl)-.

13. The method of any of claim 1, wherein Q is a single bond.

14. The method of claim 1, wherein Q is —C(O)—.

15. The method of claim 1, wherein Q is —CO(O)—.

16. The method of claim 1, wherein Q is —C(O)NH—(C$_{0-4}$alkyl)-.

17. The method of claim 1, wherein Q is —C(O)NH— or —C(O)NHCH$_2$CH$_2$—.

18. The method of claim 1, wherein Q is —C(O)NH—.

19. The method of claim 1, wherein D is a monocyclic or bicyclic ring system optionally containing up to four heteroatoms selected from N, O, and S or D is $C_{1-6}$ alkyl and wherein D is optionally substituted by one to four (CR$^9$R$^{10}$)$_w$E groups.

20. The method of claim 1, wherein D is $C_{1-6}$alkyl, alkoxy, cycloalkyl, aryl, arylalkyl, heterocyclyl or heteroaryl ring, wherein the heteroatoms are selected from O, N and S and D is optionally substituted with one to four (CR$^9$R$^{10}$)$_w$E groups.

21. The method of claim 1, wherein D is selected from methyl, ethyl, propyl, ethoxy cyclopropyl, phenyl, berizyl, berizimidazolyl, piperazinyl, pipendinyl, diazaoxazolyl or pyrimidinyl and D is optionally substituted with one to four (CR$^9$R$^{10}$)$_w$E groups.

22. The method of claim 1, wherein D is selected from 1-piperazinyl, 4-piperidinyl, 4-pyndinyl, 1,3,4-diazaoxazolyl or 3-pyndinyl, and D is optionally substituted with one or two (CR$^9$R$^{10}$)$_w$E groups.

23. The method of claim 1, wherein D is phenyl and D is optionally substituted with one or two (CR$^9$R$^{10}$)$_w$E groups.

24. The method of claim 1, wherein w is 1.

25. The method of claim 1, wherein w is 0.

26. The method of claim 1, wherein D is substituted with one to four substituents selected from halo, alkyl, nitro, alkoxy, alkoxycarbonylalkoxy, alkoxyamidoalkylamido, hydroxycarbonyl, alkoxycarbonyl, alkylaminocarbonyl, alkylcarbonylamino, aryl, heteroaryl containing 1 to 3 heteroatoms and optionally substituted with one or two alkyl groups, and heterocyclyl containing 1 to 3 heteroatoms and optionally substituted with two or more alkyl or alkoxycarbonyl groups.

27. The method of claim 1, wherein D is substituted with one to four substituents selected from chloro, fluoro, methyl, methoxy, ethoxy, methylaminocarbonyl, methoxycarbonylamino, tertbutyloxyamidoethylamido, methoxycarbonyl or phenyl.

28. The method of claim 1, wherein D is substituted with a heterocyclyl ring selected from morpholinyl or piperidinyl, where the heterocyclyl ring is further substituted with one or two methyl or methoxycarbonyl groups.

29. The method of claim 1, wherein D is substituted with heteroaryl ring selected from isoxazolyl, furyl, benzimidazolyl and thiazolyl, where the heteroaryl ring is further substituted with one or two methyl groups.

30. The method of claim 1, wherein D is substituted with N-morpholinyl, pipendin-4-yl or 1-methoxycarbonylpiperidin-4-yl.

31. The method of claim 1, wherein D is substituted with 2-benzimidazolyl, 3,5-dimethylisoxazol-4-yl, 5-methylisoxazol-3-yl or 2-methylthiazol-5-yl.

32. The method of claim 1, wherein D is selected from methyl, ethyl, propyl, isopropyl, hydroxycarbonylmethyl, methylaminocarbonylmethyl, ethoxycarbonylpropyl, ethoxycarbonylmethyl, phenyl, fluorophenyl, tolyl, methoxyphenyl, methoxycarbonylmethoxy, ethoxy, benzimidazolyl, methylpiperazinyl, piperidinyl, 1,3,4-diazaoxazolyl, morpholin-1-ylphenyl, piperidin-4-ylphenyl, 1methoxycarbonylpiperidin-4-ylphenyl, benzyl, chiorophenyl, methylcarbonylaminophenyl, bromophenyl, carboxymethyl, tertbutyloxyamidoethylamidophenyl, methylaminocarbonylmethyl, N-methoxycarbonylpiperidinyl, piperidinyl, pyridinyl, cyclopropyl, dimethylisoxazolylmethyl, methylisoxazolylmethyl and methylthiazolylmethyl.

33. The method of claim 1, wherein D is selected from methyl, ethyl, propyl, isopropyl, cydopropylmethyl, hydroxycarbonylmethyl, ethoxycarbonylpropyl, methylaminocarbonylmethyl, ethoxycarbonylmethyl, phenyl, 4-fluorophenyl, p-tolyl, 4-methoxyphenyl, 4-methoxycarbonylmethoxyphenyl, ethoxy, 2-benzimidazolylmethyl, 4-methylpiperazin-1-yl, 1,3,4-diazaoxazolyl, 4-piperidinyl, benzyl, 4-chlorophenyl, 4-morpholin-1-ylphenyl, 4-(piperidin-4-yl)phenyl. 4-(1-methoxycarbonylpiperidin-4-yl)phenyl, 4-ethoxycarbonylmethoxyphenyl, 4-methylamidophenyl, and 4-tertbutyloxyamidoethylamidophenyl.

34. The method of claim 1, wherein $R^{13}$ is selected from methyl, trifluoromethyl, tert-butyl, amido, methoxycarbonyl, carboxyl, ethoxycarbonyl, cyclopropyimethyiaminocarbonyl, thienyl, methylenedioxybenzyl, ethylenedioxybenzyl, pyridinyl, and phenyl; and $R^{13}$ is optionally substituted with one or more $R^{14}$, where $R^{14}$ is hydrogen, chloro, fluoro, hydroxy, methyl, cyano, amino, aminoethyl, N-morpholinyl, methylsulfonylamino, tertbutoxyamidomethylamido, tertbutoxyamidoethylamidophenyl, aminomethylamido, methoxycarbonylpiperazinyl, methylcarbonyl, methoxy, ethoxy, methoxycarbonyl, trifluoromethyl, hydroxymethyl, amido, aminomethyl, carboxy, tertbutoxyamidoethylamido, aminoethylamido, methylsulfonyl, N-morpholinocarbonyl, cyclopropylamido, ethylthio, carboxymethoxy, N-morpholinoethoxy, aminoethoxy, ethylamido, n-butoxy, aminopropyloxy or carboxymethoxy.

35. The method of claim 1, wherein $R^{13}$ is selected from methyl, trifluoromethyl, tert-butyl, amido, methoxycarbonyl, carboxyl, ethoxycarbonyl, cyclopropylmethylaminocarbonyl, thienyl, methylenedioxybenzyl, ethylenedioxybenzyl, 4-cyanomethylphenyl, 4-cyanophenyl, 2-chlorophenyl, 4-hydroxyphenyl, m-tolyl, 3-fluorophenyl, p-tolyl, 3-cyanophenyl, 5-methylcarbonylthien-2-yl, 5-cyanothien-2-yl, 4-methoxyphenyl, 4-methoxycarbonylphenyl, 4-fluorophenyl, 2-methoxyphenyl, 2-trifluoromethylphenyl, 4-hydroxymethylphenyl, 3-aminocarbonylphenyl, 4-aminocarbonylphenyl, 3-aminomethylphenyl, 3-carboxyphenyl, 4-carboxyphenyl, o-tolyl, 2,4-difluorophenyl, 3-aminoethylaminocarbonylphenyl, 4-aminoethylaminocarbonylphenyl, 3-aminomethylaminocarbonylphenyl, 4-aminomethylaminocarbonylphenyl, 4methylsulfonylphenyl, 4-(N-morpholino)carbonylphenyl, 4-ethoxy-3-fluorophenyl, 3-cyclopropylamidophenyl, 3-ethoxytienyl, 4-ethylthiophenyl, 4-methoxy-3-phenyl, 4-fluoro-3-methylphenyl, 3,4-difluorophenyl, 3-methyl-4-methoxyphenyl, 3-hydroxycarbonylmethoxyphenyl, 4-(N-morpholino)ethoxyphenyl, 4-hydroxyphenyl, phenyl, 3-aminoethoxyphenyl, 4-ethylaminocarbonylphenyl, 4-n-butoxyphenyl, 3-methyl4-methoxyphenyl, 3-aminopropyloxyphenyl 4-cyanomethylphenyl, 4-aminophenyl, 3-aminophenyl, 4-aminoethylphenyl, 4-morpholin-1-ylphenyl, 4-methylsulfonylaminophenyl, 3-tertbutoxyarnidomethylamidophenyl, 4-tertbutoxyamidomethylamidophenyl, 3-tert-butoxyamidoethylamidophenyl, 4-tertbutoxyamidoethylamidopheflyl, 3-aminomethylamidophenyl, 4-(methoxycarbonylpiperazin-1-yl)phenyl and 2-rnethoxypyrimidin-3-yl.

36. The method of claim 1, wherein the compound is of formula (I-1):

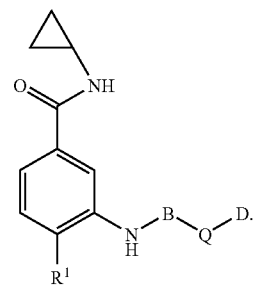

37. The method of claim 1, wherein the compound is of formula (I-2):

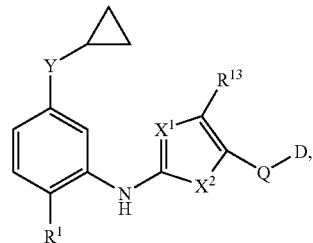

where $X^1$ is selected from O, S and optionally substituted N, where the substituent on the N when present is selected from hydrogen, alkyl, substitued alkyl, alkenyl or alkynyl and $X^2$ is S or O.

38. The method of claim 1, wherein the compound is of formula (I-3):

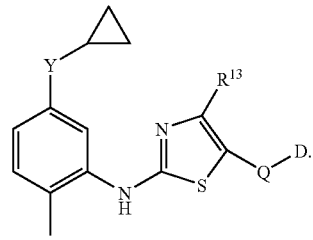

39. The method of claim 1, wherein the compound is of formula (I-4):

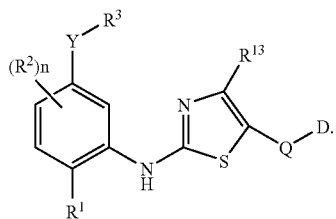

40. The method of claim 1, wherein the compound is of formula (I-5):

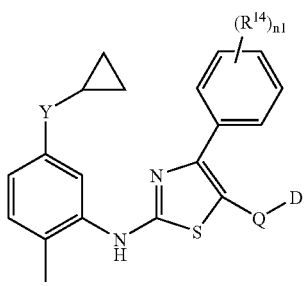

where n₁ is 0-5.

41. The method of claim 1, wherein the compound is of formula (I-6):

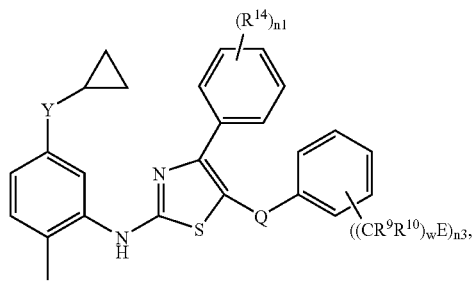

where n₃ is 1-4.

42. The method of claim 1, wherein the compound is of formula (I-7):

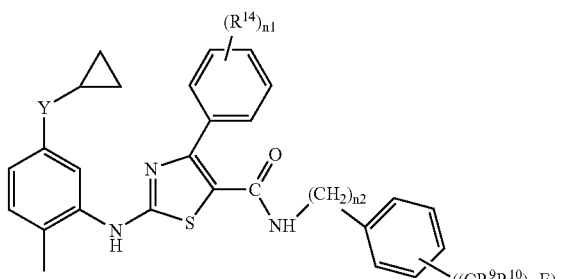

where n₂ is 0-4.

43. The method of claim 1, wherein the compound is of formula (I-8):

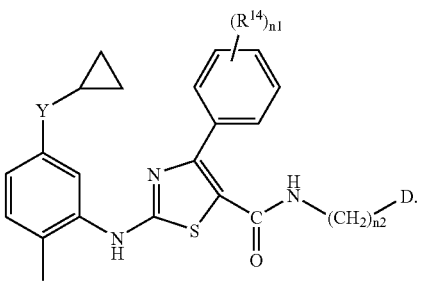

44. The method of claim 1, wherein the compound is of formula (I-9):

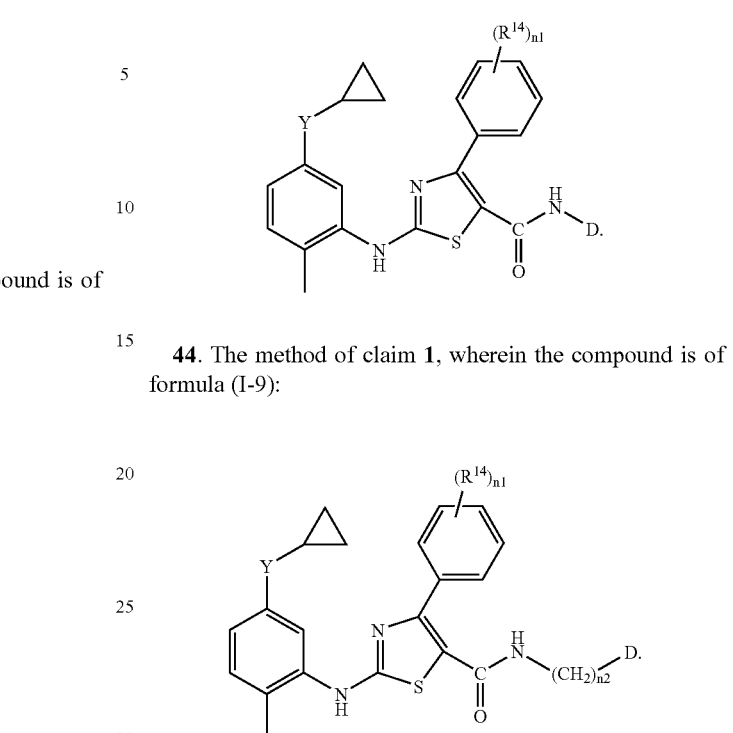

45. The method of claim 1, wherein the compound is of any of formulae (I-10):

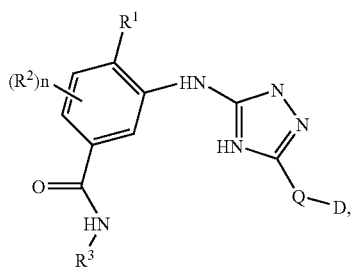

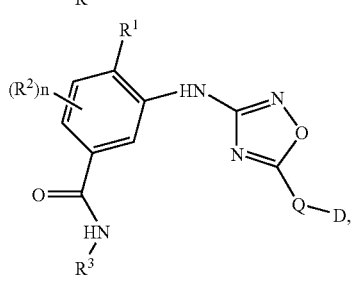

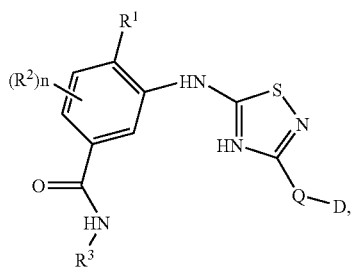

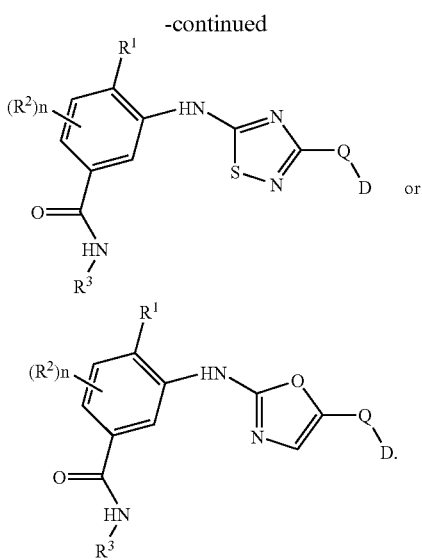

-continued

46. The method of claim 1, wherein the compound is selected from:
N-methoxy-4-methyl-3-(5-phenyl-4H-[1,2,4]triazol-3-ylamino)-benzamide;
N-methoxy-4-methyl-3-(5-phenyl-[1,2,4]oxadiazol-3-ylamino)-benzamide;
N-Cyclopropyl-4-methyl-3-(4-phenyl-thiazol-2-ylamino)-benzamide;
3-[4-(4-Cyano-phenyl)-thiazol-2-ylamino]-N-cyclopropyl-4-methyl-benzamide;
N-Cyclopropyl-3-[4-(4-fluoro-phenyl)-thiazol-2-ylamino]-4-methyl-benzamide;
N-Cyclopropyl-3-[4-(4-methoxy-phenyl)-thiazol-2-ylamino]-4-methyl-benzamide;
N-Cyclopropyl-3-[4-(3-methoxy-phenyl)-thiazol-2-ylamino]-4-methyl-benzamide;
N-Cyclopropyl-3-[4-(2-methoxy-phenyl)-thiazol-2-ylamino]-4-methyl-benzamide;
N-Cyclopropyl-4-methyl-3-(5-methyl-4-phenyl-thiazol-2-ylamino)-benzamide;
2-(5-Cyclopropylcarbamoyl-2-methyl-phenylamino)-thiazole-4-carboxylic acid phenylamide;
N-Isopropyl-4-methyl-3-(4-phenyl-thiazol-2-ylamino)-benzamide;
N-Ethyl-4-methyl-3-(4-phenyl-thiazol-2-ylamino)-benzamide;
N-(2-Methoxy-ethyl)-4-methyl-3-(4-phenyl-thiazol-2-ylamino)-benzamide;
4-Methyl-3-(4-phenyl-thiazol-2-ylamino)-I-thiazol-2-yl-benzamide;
4-Methyl-3-(4-phenyl-thiazol-2-ylamino)-N-[1,2,4]triazol-4-yl-benzamide;
4-Methyl-N-(5-methyl-[1,3,4]thiadiazol-2-yl)-3-(4-phenyl-thiazol-2-ylamino)-benzamide;
N-Cyclopropyl-4-methyl-3-(5-phenyl-oxazol-2-ylamino)-benzamide;
N-Cyclopropyl-4-methyl-3-(5-phenyl-4H-[1,2,4]triazol-3-ylamino)-benzamide;
N-Cyclopropyl-4-methyl-3-(5-phenyl-[1,2,4]oxadiazol-3-ylamino)-benzamide;
N-Cyclopropyl-4-methyl-3-(5-phenyl-[1,3,4]thiadiazol-2-ylamino)-benzamide;
N-Cyclopropyl-4-methyl-3-(3-phenyl-[1,2,4]thiadiazol-5-ylamino)-benzamide;
2-(5-Cyclopropylcarbamoyl-2-methyl-phenylamino)-4-methyl-thiazole-5-carboxylic acid benzyl ester;
2-(5-Cyclopropylcarbamoyl-2-methyl-phenylamino)-4-methyl-thiazole-5-carboxylic acid benzylamide;
2-(5-Cyclopropylcarbamoyl-2-methyl-phenylamino)-thiazole-4-carboxylic acid ethyl ester;
5-Bromo-2-(5-cyclopropylcarbamoyl-2-methyl-phenylamino)-thiazole-4-carboxylic acid ethyl ester;
2-(5-Cyclopropylcarbamoyl-2-methyl-phenylamino)-4-(4-nitro-phenyl)-thiazole-5-carboxylic acid ethyl ester;
N-Cyclopropyl-4-methyl-3-[4-(4-nitro-phenyl)-thiazol-2-ylamino]-benzamide;
3-[5-Bromo-4-(4-nitro-phenyl)-thiazol-2-yiamino]-N-cyclopropyl-4-methyl-benzamide;
2-(5-Cyclopropylcarbamoyl-2-methyl-phenylamino)-4-(4-morpholin-4-yl-phenyl)-thiazole-5-carboxylic acid benzylamide;
2-(5-Cyclopropylcarbamoyl-2-methyl-phenylamino)-thiazole-5-carboxylic acid methyl ester;
2-(5-Cyclopropylcarbamoyl-2-methyl-phenylamino)-4-phenyl-thiazole-5-carboxylic acid cyclopropylmethylamide;
4-{3-[2-(5-Cyclopropylcarbamoyl-2-methyl-phenylamino)-5-methoxycarbonyl-thiazol-4-yl]-phenyl}-piperidine-1-carboxylic acid methyl ester;
4-{3-[2-(5-Cyclopropylcarbamoyl-2-methyl-phenylamino)-5-(cyclopropylmethyl-carbamoyl)-thiazol-4-yl]-phenyl}-piperidine-1-carboxylic acid methyl ester;
4-{3-[2-(5-cyclopropylcarbamoyl-2-methyl-phenylamino)-5-[1,3,4]oxadiazol-2-yl-thiazol-4-yl]-phenyl}-piperidinium trifluoroacetate;
N-Cyclopropyl-4-methyl-3-[4-(4-nitro-phenyl)-5-[1,3,4]oxadiazol-2-yl-thiazol-2-ylamino]benzamide;
2-(5-Cyclopropylcarbamoyl-2-methyl-phenylamino)-thiazole-5-carboxylic acid benzylamide; 4-Bromo-2-(5-cyclopropylcarbamoyl-2-methyl-phenylamino)-thiazole-5-carboxylic acid benzylamide;
2-(5-Cycloproplcarbamoyl-2-methyl-phenylamino)-4-(4-fluoro-3-methyl-phenyl)-thiazole-5-carboxylic acid benzylamide;
4-(4-Cyanomethyl-phenyl)-2-(5-cyclo-propylcarbamoyl-2-methylphenylamino)-thiazole-5-carboxylic acid benzylamide;
4-(4-Cyano-phenyl)-2-(5cyclopropyl-carbamoyl-2-methyl-phenylamino)-4,5-dihydro-thiazole-5-carboxylic acid benzylamide;
4-(2-Chloro-phenyl)-2-(5-cyclopropyl-carbamoyl-2-methyl-phenylamino)-thiazole-5-carboxylic acid benzylamide;
2-(5-Cyclopropyl-carbamoyl-2-methyl-phenylamino)-4-(3-hydroxymethylphen-yl)-thiazole-5-carbox-ylic acid benzylamide;
2-(5-Cyclopropylcar-bamoyl-2-methyl-phenylamino)-4-m-tolyl-thiazole-5-carboxylic acid benzylamide;
2-(5-Cyclopropylcar-bamoyl-2-methyl-phenylamino)-4-(3-fluorophenyl)thia-zole-5-carboxylic acid benzylamide;
2-(5-Cyclopropylcar-bamoyl-2-methyl-phenylamino)-4-p-tolyl-thiazole-5-carboxylic acid benzylamide;
4-(3Cyano-phenyl)-2-(5-cyclopropyl-carbamoyl-2-methyl-phenylamino)thia-zole-5-carboxylic acid benzylamide;
4-(5-Acetyl-thiophen-2-yl)-2-(5-cyclo-propylcarbamoyl-2-methylphenylamino)-thiazole-5-carboxylic acid benzylamide;

4-Benzo[1,3]dioxol-5-yl-2-(5-cycloprop-ylcarbamoyl-2-methylphenylamino)-thiazole-5-carboxylic acid benzylamide;

4-(5-Cyano-thiophen-2-yl)-2-(5-cycloprop-ylcarbamoyl-2-methylphenylamino)-thiazole-5-carboxylic acid benzylamide;

2-(5-Cyclopropylcar-bamoyl-2-methyl-phenylamino)-4-(4-methoxy-phenyl)-thiazole-5-carboxylic acid benzylamide;

4-[5-Benzylcarbamo-yl-2-(5-cyclopropyl-carbamoyl-2-methyl-phenylamino)thiaz-ol-4-yl]benzoic acid ethyl ester;

3-[5-Benzylcarbamo-yl-2-(5-cyclopropyl-carbamoyl-2-methyl-phenylamino)thiaz-ol-4-yl]-benzoic acid methyl ester;

2-(5-Cyclopropyl-carbamoyl-2-methyl-phenyiamino)-4-(4-fluoro-phenyl)-thiazole-5-carboxylic acid benzylamide;

2-(5-Cyclopropyl-carbamoyl2-methyl-phenylamino)-4-(2-methoxy-phenyl)thiazole-5-carboxlic acid benzylamide;

2-(5-Cyclopropylcar-bamoyl-2-methyl-phenylamino-4-(3-methoxy-phenyl)thiazol-5-carboxlic acid benzylamide;

2-(5-Cyclopropylcar-bamoyl-2-methyl-phenylamino)-4-(2-trifluoromethyl-phenyl)-thiazole-5-carboxylic acid benzylamide;

2-(5-Cyclopropylcar-bamoyl-2-methyl-phenylamino)-4-(4-hydroxymethyl-phenyl)-thiazole-5-carboxylic acid benzylamide;

4-(3-Carbamoylphen-yl)-2-(5-cyclopropyl-carbamoyl-2-methyl-phenylamino)-thiazole-5-carboxylic acid benzylamide;

4-(4-Carbamoyl-phenyl)-2-(5-cyclo-propylcarbamoyl-2-methylphenylamino)-thiazole-5-carboxylic acid benzylamide;

2-(5-Cyclopropylcar-bamoyl-2-methyl-phenylamino)-4-(2,3-dihydrobenzo[1,4]di-oxin-6-yl)-thiazole-5-carboxylic acid benzylamide;

4-(3-Aminomethyl-phenyl)-2-(5-cyclo-propylcarbamoyl-2-methylphenylamino)-thiazole-5-carboxylic acid benzylamide;

3-[5-Benzylcarbamo-yl-2-(5-cyclopropyl-carbamoyl-2-methyl-phenylamino)-thiaz-ol-4-yl]-benzoic acid;

4-[5-Benzylcarbamo-yl-2-(5-cyclopropyl-carbamoyl-2-methyl-phenylamino)thiazol-4-yl]-benzoic acid;

2-(5-Cyclopropyl-bamoyl-2-methyl-phenylamino)-4-o-tolyl-thiazole-5-car-boxylic acid benzylamide;

2-(5-Cyclopropylcar-bamoyl-2-methyl-phenylamino)-4-(2,4-difluoro-phenyl)-thiazole-5-carboxylic acid benzylamide;

2-(5-Cyclopropylcar-bamoyl-2-methyl-phenylamino)-4-(4-methanesulfonyl-phenyl)-thiazole-5-carboxylic acid benzylamide;

2-(5-Cyclopropylcar-bamoyl-2-methyl-phenylamino)-4-[4-(morpholine-4-carbonyl)-phenyl]-thiazole-5-carboxylic acid benzylamide;

2-(5-Cyclopropylcar-bamoyl-2-methyl-phenylamino)-4-(4-ethoxy-3-fluoro-phenyl)-thiazole-5-carboxylic acid benzylamide;

2-(5-Cyclopropylcar-bamoyl-2-methyl-phenylamino)-4-(3-cyclopropylcarbamoyl-phenyl)-thiazole-5-carboxylic acid benzylamide;

2-(5-Cyclopropylcar-bamoyl-2-methyl-phenylamino)-4-(3-ethoxy-phenyl)-thiazole-5-carboxylic acid benzylamide;

2-(5-Cyclopropylcar-bamoyl-2-methyl-phenylamino)-4-(4-ethylsulfanyl-phenyl)-thiazole-5-carboxylic acid benzylamide;

2-(5-Cyclopropylcar-bamoyl-2-methyl-phenylamino)-4-(3-fluoro-4-methoxy-phenyl)-thiazole-5-carboxylic acid benzylamide;

2-(5-Cyclopropylcar-bamoyl-2-methyl-phenylamino)-4-(4-fluoro-3-methoxy-phenyl)-thiazole-5-carboxylic acid benzylamide;

2-(5-Cyclopropylcar-bamoyl-2-methyl-phenylamino)-4-(3,4-difluoro-phenyl)-thiazole-5-carboxylic acid benzylamide;

2-(5-Cyclopropylcar-bamoyl-2-methyl-phenylamino)-4-(2-fluoro-phenyl)-thiazole-5-carboxylic acid benzylamide;

2-(5-Cyclopropylcar-bamoyl-2-methyl-phenylamino)-4-(4-ethoxy-phenyl)-thiazole-5-carboxylic acid benzylamide;

2-(5-Cyclopropylcar-bamoyl-2-methyl-phenylamino)-4-(1H-indol-5-yl)-thiazole-5-carboxylic acid benzylamide;

2-(5-Cyclopropylcar-bamoyl-2-methyl-phenylamino)-4-(4-methoxy-3-methyl-phenyl)-thiazole-5-carboxylic acid benzylamide;

2-(5-Cyclopropylcar-bamoyl-2-methyl-phenylamino)-4-(4-ethylcarbamoyl-phenyl)-thiazole-5-carboxylic acid benzylamide;

2-(5-Cyclopropylcar-bamoyl-2-methyl-phenylamino)-4-(4-hydroxy-phenyl)-thiazole-5-carboxylic acid benzylamide, 2-(5-Cyclopropylcar-bamoyl-2-methyl-phenylamino)-4-(4-propoxy-phenyl)-thiazole-5-carboxylic acid benzylamide;

4-(4-Amino-phenyl)-2-(5-cyclopropylcarbamoyl-2-methyl-phenylamino)-thiazole-5-carboxylic acid benzylamide;

4-(3-Amino-phenyl)-2-(5-cyclopropylcarbamoyl-2-methyl-phenylamino)-thiazole-5-carboxylic acid benzylamide;

4-[3-(3-Amino-propionylamino)-phenyl]-2-(5-cyclopropylcarbamoyl-2-methyl-phenylamino)-thiazole-5-carboxylic acid benzylamide ditrifluoroacetate;

4-[4-(2-Amino-acetylamino)-phenyl]2-(5-cyclopropylcarbamoyl-2-methyl-phenylamino)-thiazole-5-carboxylic acid benzylamide ditrifluoroacetate;

2-{4-[5-benzylcarbamoyl-2-(5-cyclopropylcarbamoyl-2-methyl-phenylamino)-thiazo-4-yl]-phenylcarbamoyl}-ethyl-ammonium ditrifluoroacetate;

4-(4-Cyanomethyl-phenyl)-2-(5-cyclopropytcarbamoyl-2-methyl-phenylamino)-thiazole-5-carboxylic acid benzylamide; and 4-[4-(2-Amino-ethyl)-phenyl]-2-(5-cyclopropylcarbamoyl-2-methyl-phenylamino)-thiaxzole-5-carboxytic acid benzylamide.

* * * * *

UNITED STATES PATENT AND TRADEMARK OFFICE
CERTIFICATE OF CORRECTION

| | | |
|---|---|---|
| PATENT NO. | : 7,652,044 B2 | Page 1 of 1 |
| APPLICATION NO. | : 10/860768 | |
| DATED | : January 26, 2009 | |
| INVENTOR(S) | : Dong et al. | |

It is certified that error appears in the above-identified patent and that said Letters Patent is hereby corrected as shown below:

On the cover page,

Item [*] Notice: Subject to any disclaimer, the term of this patent is extended or adjusted under 35 USC 154(b) by 663 days Delete the phrase "by 663 days" and insert -- by 1,167 days --

Signed and Sealed this

Twentieth Day of April, 2010

David J. Kappos
*Director of the United States Patent and Trademark Office*